US008022076B2

(12) United States Patent
Ford et al.

(10) Patent No.: US 8,022,076 B2
(45) Date of Patent: Sep. 20, 2011

(54) SUBSTITUTED THIENO[2,3-D]PYRIMIDINES AS POTASSIUM CHANNEL INHIBITORS

(75) Inventors: John Ford, Huntingdon (GB); Nicholas John Palmer, Cambridge (GB); John Frederick Atherall, Essex (GB); David John Madge, West Sussex (GB); Brad Sherborne, Stirling (GB); Mark Bushfield, Balsham (GB); Edward Benedict Stevens, Suffolk (GB)

(73) Assignee: Xention Limited, Pampisford, Cambridge (GB)

( * ) Notice: Subject to any disclaimer, the term of this patent is extended or adjusted under 35 U.S.C. 154(b) by 568 days.

(21) Appl. No.: 10/864,771

(22) Filed: Jun. 10, 2004

(65) Prior Publication Data

US 2005/0026935 A1 Feb. 3, 2005

Related U.S. Application Data

(60) Provisional application No. 60/477,518, filed on Jun. 11, 2003.

(30) Foreign Application Priority Data

Jun. 11, 2003 (GB) .................................. 0315950.6

(51) Int. Cl.
C07D 495/04 (2006.01)
A61K 31/519 (2006.01)
A61P 9/06 (2006.01)

(52) U.S. Cl. ..................................... 514/260.1; 544/278
(58) Field of Classification Search .................. 544/278; 514/260.1
See application file for complete search history.

(56) References Cited

U.S. PATENT DOCUMENTS

| | | | |
|---|---|---|---|
| 3,845,065 A | 10/1974 | Shen et al. | |
| 3,903,095 A | 9/1975 | Shen et al. | |
| 4,146,716 A * | 3/1979 | Cox et al. ..................... | 544/278 |
| 4,165,374 A | 8/1979 | Troxler et al. | |
| 6,184,221 B1 | 2/2001 | Gerlach et al. | |
| 6,521,618 B2 | 2/2003 | Boschelli et al. | |
| 6,531,495 B1 | 3/2003 | Brendel et al. | |
| 7,199,119 B2 | 4/2007 | Burkitt et al. | |
| 7,456,187 B2 | 11/2008 | Ford et al. | |
| 2002/0161011 A1 | 10/2002 | Beaudoin et al. | |
| 2003/0027829 A1 | 2/2003 | Reed et al. | |
| 2004/0097485 A1 | 5/2004 | Burkitt et al. | |
| 2004/0180873 A1* | 9/2004 | Hanssen et al. .......... | 514/210.21 |
| 2005/0282829 A1 | 12/2005 | Ford et al. | |
| 2006/0183768 A1 | 8/2006 | Ford et al. | |
| 2007/0161672 A1 | 7/2007 | Ford et al. | |

FOREIGN PATENT DOCUMENTS

| | | |
|---|---|---|
| AU | 521790 | 11/1979 |
| DE | 19 65 710 | 7/1970 |
| DE | 28 31 677 A1 | 2/1979 |
| DE | 226 893 A1 | 9/1985 |
| DE | 248 593 A1 | 8/1987 |
| DE | 248593 A1 * | 8/1987 |
| DE | 101 04 802 A1 | 8/2002 |
| EP | 0 126 970 A2 | 12/1984 |
| GB | 1284930 | 8/1972 |
| GB | 1 570 494 | 7/1980 |
| JP | 48-81892 | 11/1973 |
| JP | 48-81893 | 11/1973 |
| JP | 3254843 | 2/1995 |
| JP | 07-076586 | 3/1995 |
| RU | 2 116 309 C1 | 7/1998 |
| WO | WO 98/04521 A1 | 2/1998 |
| WO | WO 98/04542 A1 | 2/1998 |
| WO | WO 98/18475 A1 | 5/1998 |
| WO | WO 98/18476 A1 | 5/1998 |
| WO | WO 99/37607 A1 | 7/1999 |
| WO | WO 99/62891 A1 | 12/1999 |
| WO | WO 00/12492 A1 | 3/2000 |
| WO | WO 00/25774 A1 | 5/2000 |
| WO | WO 01/00573 A1 | 1/2001 |
| WO | WO 01/21609 A1 | 3/2001 |
| WO | WO 01/21610 A1 | 3/2001 |
| WO | WO 01/25189 A1 | 4/2001 |
| WO | WO 01/25224 A1 | 4/2001 |
| WO | WO 01/40231 A1 | 6/2001 |
| WO | WO 01/46155 A1 | 6/2001 |
| WO | WO 02/24655 A1 | 3/2002 |

(Continued)

OTHER PUBLICATIONS

Katada et.a l. (Bioorg. & Med. Chem. Letts., 1999, 9, 797-802).*
Hosni et. al. (Acta Poloniae Pharmaceutica, 1999, 56(1), 49-56).*
Jordis et. al. (Vestn. Slov. Kem. Drus. 1986, 33, 217-238).*
Hozien et. al. (Synth. Comm. 1996, 26, 3733-3755).*
Boehmi et. al. (DD 248593 A1); See compound with registry No. 113417-61-1, CAS printout 76 of 90.*
Amos, G.J., et al., "Differences between outward currents of human atrial and subepicardial ventricular myocytes," *J. Physiol. 491*:31-50, Cambridge Univ. Press. (1996).

(Continued)

*Primary Examiner* — Susanna Moore
(74) *Attorney, Agent, or Firm* — Sterne, Kessler, Goldstein & Fox P.L.L.C.

(57) ABSTRACT

This invention relates to novel compound of formula (I)

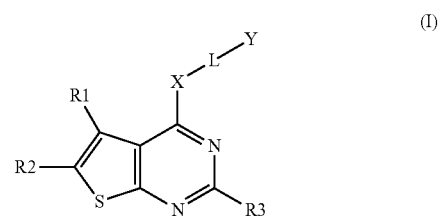

(I)

or pharmaceutically acceptable salts thereof. The invention is also directed to the uses of compounds having formula (I) in the treatment or prevention of diseases or disorders which requires potassium channel inhibition to an animal, mammal or human in need thereof. The invention is also directed to the use of compounds having formula (I) in the treatment or prevention of arrhythmia to an animal, mammal or human in need thereof.

20 Claims, No Drawings

FOREIGN PATENT DOCUMENTS

| | | |
|---|---|---|
| WO | WO 01/27107 A2 | 4/2002 |
| WO | WO 02/36556 A2 | 5/2002 |
| WO | WO 02/44137 A1 | 6/2002 |
| WO | WO 02/46162 A1 | 6/2002 |
| WO | WO 02/48131 A1 | 6/2002 |
| WO | WO 02/060874 A1 | 8/2002 |
| WO | WO 02/064581 A1 | 8/2002 |
| WO | WO 02/087568 A1 | 11/2002 |
| WO | WO 02/088073 A1 | 11/2002 |
| WO | WO 02/100825 A2 | 12/2002 |
| WO | WO 03/000675 A1 | 1/2003 |
| WO | WO 03/063797 A2 | 8/2003 |
| WO | WO 2004/092123 A2 | 10/2004 |
| WO | WO 2004092123 A2 * | 10/2004 |
| WO | WO 2004/111057 A1 | 12/2004 |
| WO | WO 2005/105809 A1 | 11/2005 |
| WO | WO 2006/061642 A1 | 6/2006 |
| WO | WO 2006/106326 A1 | 10/2006 |
| WO | WO 2007/005534 A2 | 1/2007 |
| WO | WO 2007/066127 A2 | 6/2007 |

OTHER PUBLICATIONS

Armstrong, C.M. and Hille, B., "Voltage-Gated Ion Channels and Electrical Excitability," *Neuron* 20:371-380, Cell Press (1998).

Bachmann, A., et al., "Characterization of a novel Kv1.5 channel blocker in *Xenopus oocytes*, CHO cells, human and rat cardiomyocytes," *Naunyn-Schmiedeberg's Arch. Pharmacol.* 364:472-478, Springer-Verlag (2001).

Belen'kii, L.I., et al., "Synthesis of Heterocyclic Compounds from the Products of Addition of Polyhaloalkanes to Unsaturated Systems. 4. Synthesis of Substituted Furo[2,3-D]Pyrimidines," *Chemistry of Heterocyclic Compounds* 29:109-114, Plenum Publishing Corporation (1993).

Brendel, J. and Peukert, S., "Blockers of the Kv1.5 channel for the treatment of atrial arrhythmias," *Expert Opin. Ther. Patents* 12:1589-1598, Ashley Publications Ltd. (2002).

Campaigne, E., "Thiophenes and their Benzo Derivatives: (iii) Synthesis and Applications," in *Comprehensive Heterocyclic Chemistry: The Structure, Reactions, Synthesis and Uses of Heterocyclic Compounds 4*, Bird, C.W., et al., eds., Pergamon Press, New York, NY, pp. 863-934 (1984).

Colatsky, T.J., et al., "Channel Specificity in Antiarrhythmic Drug Action: Mechanism of Potassium Channel Block and Its Role in Suppressing and Aggravating Cardiac Arrhythmias," *Circulation* 82:2235-2242, American Heart Association (1990).

Courtemanche, M., et al., "Ionic targets for drug therapy and atrial fibrillation-induced electrical remodeling: insights from a mathematical model," *Cardiovasc. Res.* 42:477-489, Elsevier Science B.V. (1999).

Fedida, D., et al., "Identity of a Novel Delayed Rectifier Current From Human Heart With a Cloned K$^+$ Channel Current," *Circ. Res.* 73:210-216, Lippincott Williams & Wilkins (1993).

Feng, J., et al., "Antisense Oligodeoxynucleotides Directed Against Kv1.5 mRNA Specifically Inhibit Ultrarapid Delayed Rectifier K$^+$ Current in Cultured Adult Human Atrial Myocytes," *Circ. Res.* 80:572-579, American Heart Association, Inc. (1997).

Feng, J., et al., "Effects of Class III Antiarrhythmic Drugs on Transient Outward and Ultra-rapid Delayed Rectifier Currents in Human Atrial Myocytes," *J. Pharmacol. Exp. Ther.* 281:384-392, American Society for Pharmacology and Experimental Therapeutics (1997).

Ford, J.W., et al., "Potassium Channels: Gene Family, Therapeutic Relevance, High-Throughput Screening Technologies and Drug Discovery," in *Progress in Drug Research*, vol. 58, Jucker, E., ed., Birkhäuser Verlag, Boston, MA, pp. 133-168 (2002).

Godreau, D., et al., "Mechanisms of Action of Antiarrhythmic Agent Bertosamil on hKv1.5 Channels and Outward Potassium Current in Human Atrial Myocytes," *J. Pharmacol. Exp. Ther.* 300:612-620, American Society for Pharmacology and Experimental Therapeutics (2002).

Gutman, G.A., et al., "International Union of Pharmacology. XLI. Compendium of Voltage-Gated Ion Channels: Potassium Channels," *Pharmacol. Rev.* 55:583-586, American Society for Pharmacology and Experimental Therapeutics (Dec. 2003).

Hebert, S.C., "General Principles of the Structure of Ion Channels," *Am. J. Med.* 104:87-98, Excerpta Medica, Inc. (1998).

Hosni, H.M., et al., "Thienopyrimidines II: Synthesis of Newer Thieno[2,3-d]-Pyrimidines and Their Quaternized Derivatives with Molluscicidal Activity," *Acta Pol. Pharm.—Drug Res.* 56:49-56, Polish Pharmaceutical Society (1999).

Hozien, Z.A., et al., "Synthesis and Application of Some New Thienopyrimidine Dervatives as Antimicrobial Agents," *Synthetic Communications* 26:3733-3755, Marcel Dekker, Inc. (1996).

Ismail, K.A., et al., "Synthesis and Antimicrobial Activity of Some Tetramethylenethieno [2,3-d]pyrimidine derivatives," *Il Farmaco* 50:611-616, Elsevier (1995).

Jordis, U., et al., "7,9-Dideaza-9-Thiaadenines (4-Arninothieno/2,3-d/pyrimidines) as Potential Anticytokinines," *Vestn. Slov. Kem. Drus.* 33:217 -238, Drustvo (1986).

Katada, J., et al., "Cytotoxic effects of NSL-1406, a new thienopyrimidine derivative, on leukocytes and osteoclasts," *Bioorg. Med. Chem. Lett.* 9:797-802, Elsevier Science Ltd. (1999).

Knobloch, K., et al., "Electrophysiological and antiarrhythmic effects of the novel $I_{Kur}$ channel blockers, S9947 and S20951, on left vs. right pig atrium in vivo in comparison with the $I_{Kr}$ blockers dofetilide, azimilide, d,l-sotalol and ibutilide," *Naunyn-Schmiedeberg's Arch. Pharmacol.* 366:482-487, Springer-Verlag (2002).

Konno, S., et al., "Synthesis of Thienopyrimidine Derivatives and Their Antifungal Activities," *Yakugaku Zasshi 109*: Pharmaceutical Society of Japan (1989).

Li, G.-R., et al., "Evidence for Two Components of Delayed Rectifier K$^+$ Current in Human Ventricular Myocytes," *Circ. Res.* 78:689-696, American Heart Association, Inc. (1996).

Malayev, A.A., et al., "Mechanism of Clofilium Block of the Human Kv1.5 Delayed Rectifier Potassium Channel," *Mol. Pharmacol.* 47:198-205, American Society for Pharmacology and Experimental Therapeutics (1995).

Marbán, E., "Cardiac channelopathies," *Nature* 415:213-218, Macmillan Magazines Ltd. (2002).

Matsuda, T., et al., "Inhibition by a novel anti-arrhythmic agent, NIP-142, of cloned human cardiac K$^+$ channel Kv1.5 current," *Life Sci.* 68:2017-2024, Elsevier Science, Inc. (2001).

Moneer, A.A., et al., "Reaction of 3-Amino and 4-hydrazino-5,6-Tetramethylenethieno[2,3-d]Pyrimidine Derivatives with Azlactones," *Egypt. J. Pharm. Sci.* 34:599-609, National Information & Documentation Centre (1993).

Munchhof, M.J., et al., "Design and SAR of thienopyrimidine and thienopyridine inhibitors of VEGFR-2 kinase activity," *Bioorg. Med. Chem. Lett.* 14:21-24, Elsevier Ltd. (Jan. 2004).

Nakayama, J., "Thiophenes and their Benzo Derivatives: Synthesis," in *Comprehensive Heterocyclic Chemistry II*, vol. 2: Katritzky, A.R., et al., eds., pp. 607-677, Pergamon Press, New York, NY (1996).

Nattel, S., et al., "Cardiac Ultrarapid Delayed Rectifiers: A Novel Potassium Current Family of Functional Similarity and Molecular Diversity," *Cell Physiol. Biochem.* 9:217-226, S. Karger AG (1999).

Nattel, S., "Therapeutic implications of atrial fibrillation mechanisms: can mechanistic insights be used to improve AF management?," *Cardiovasc. Res.* 54:347-360, Elsevier Science B.V. (2002).

Noravyan, A.S., et al., "Synthesis and anticonvulsive activity of 4-alkyl (or aryl)amino-6,6-dimethyl-5,6-dihydro-8H-pyrano (or thiopyrano)[3,4-b]thieno[5,4-d] pyrimidines," *Khimiko-Farmatsevticheskii Zhurnal* 11:38-42, Folium Publishing Company (1977).

Peukert, S., et al., "Identification, Synthesis, and Activity of Novel Blockers of the Voltage-Gated Potassium Channel Kv1.5," *J. Med. Chem.* 46:486-498, American Chemical Society (Feb. 2003).

Ram, V.J., "Thieno[2,3-*d*]pyrimidines as Potential Chemotherapeutic Agents," *Arch. Pharm. (Weinheim)* 312:19-25, Verlag Chemie, GmbH (1979).

Ram, V.J., et al., "Thieno[2,3-*d*]pyrimidines as Potential Chemotherapeutic Agents. II," *J. Heterocylic Chem.* 18:1277-1280, HeteroCorporation (1981).

Shehata, I.A., et al., "Synthesis, Antitumor and Anti-HIV-1 Testing of Certain Thieno[2,3-*d*]pyrimidine, Thieno[2,3-*d*]imidazo[1,2-

*c*]pyrimidine and Thieno[2,3-*d*] [1,3]thiazine Derivatives," *Med. Chem. Res.* 6:148-163, Birkhäuser Boston (1996).

Stewart, A.O., et al., "Discovery of Inhibitors of Cell Adhesion Molecule Expression in Human Endothelial Cells. 1. Selective Inhibition of ICAM-1 and E-Selectin Expression," *J. Med. Chem.* 44:988-1002, American Chemical Society (2001).

Tyle, P. "Iontophoretic Devices for Drug Delivery," *Pharm. Res.* 3:318-326, Plenum Publishing Corporation (1986).

Wang, Z., et al., "Sustained Depolarization-Induced Outward Current in Human Atrial Myocytes: Evidence for a Novel Delayed Rectifier $K^+$ Current Similar to Kv1.5 Cloned Channel Currents," *Circ. Res.* 73:1061-1076, American Heart Association (1993).

Wang, Z., et al., "Effects of Flecainide, Quinidine, and 4-Aminopyridine on Transient Outward and Ultrarapid Delayed Rectifier Currents in Human Atrial Myocytes," *J. Pharmacol. Exp. Ther.* 272:184-196 (1995).

Wirth, K.J., et al., "Atrial effects of the novel $K^+$-channel-blockers AVE0118 in anesthetized pigs," *Cardiovasc. Res.* 60:298-306, Elsevier B.V. (Nov. 2003).

Xu, D.H. And Xu, S.B., "The Expression of Arrhythmic Related Genes on *Xenopus* Oocytes for Evaluation of Class III Antiarrhythmic Drugs from Ocean Active Material," *Acta Genetica Sinica* 27:195-201, Science Press and Elsevier Press (2000).

Dialog File 351, Accession No. 607592, Derwent WPI English language abstract for JP 48-81893 (listed on accompanying PTO/SB/08A as document FP2), Downloaded Mar. 14, 2007.

Dialog File 351, Accession No. 3566123, Derwent WPI English language abstract for DD 226 893 A1 (listed on accompanying PTO/SB/08A as document FP10), Downloaded Mar. 14, 2007.

Dialog File 351, Accession No. 12964595, Derwent WPI English language abstract for DE 101 04 802 A1 (listed on accompanying PTO/SB/08A as document FP23), Downloaded Mar. 14, 2007.

STNEasy Database, Accession No. 1978:37739, English language abstract for Noravyan, A.S., et al., "Synthesis and anticonvulsive activity of 4-alkyl (or aryl)amino-6,6-dimethy1-5,6-dihydro-8H-pyrano (or thiopyrano)[3,4-b]thieno[5,4-d] pyrimidines," *Khimiko-Farmatsevticheskii Zhurnal* 11:38-42, Folium Publishing Company (1977).

Abdelrazek, F.M., et al., "Synthesis of Novel Thieno[2,3-*d*]pyrimidine, Thieno[2,3-*b*]pyridine and Thiazolo[3,2-*a*]thieno[2,3-*d*]pyrimidine Derivatives and their effect on the production of Mycotoxins," *Arch. Pharm.* (*Weinheim*) 325:301-306, VCH Verlagsgesellschaft mbH (1992).

Baell, J.B., et al., "Khellinone Derivatives as Blockers of the Voltage-Gated Potassium Channel Kv1.3: Synthesis and Immunosuppressive Activity," *J. Med. Chem.* 47:2326-2336, American Chemical Society (Apr. 2004).

Barker, J.M., et al., "Thienopyridines. Part 6. Synthesis and Nucleophilic Substitution of Some Chlorothieno[2,3-b]pyridine Derivatives, and Comparisons with the Analogous Quinoline Compounds," *J. Chem. Research* (*M*):2501-2523, Science Reviews, Ltd. (1985).

Beeton, C., et al., "Selective blockade of T lymphocyte $K^+$ channels ameliorates experimental autoimmune encephalomyelitis, a model for multiple sclerosis," *Proc. Natl. Acad. Sci. USA* 98:13942-13947, National Academy of Sciences (2001).

Beeton, C., et al., "A Novel Fluorescent Toxin to Detect and Investigate Kv1.3 Channel Up-regulation in Chronically Activated T Lymphocytes," *J. Biol. Chem.* 278:9928-9937, American Society for Biochemistry and Molecular Biology, Inc. (Mar. 2003).

Boschelli, D.H., et al., "Identification of 7-Phenylaminothieno-[3,2-*b*]pyridiale-6-carbonitriles as a New Class of Src Kinase Inhibitors," *J. Med. Chem.* 47:6666-6668, American Chemical Society (Dec. 2004).

Charvát, T., et al., "Diethyl Acetonedicarboxylate—a Precursor for the Synthesis of New Substituted 4-Aminoquinolines and Fused 4-Aminopyridines," *Monatshefte für Chemie* 126:333-340, Springer-Verlag (1995).

Desir, G.V., "Kv1.3 potassium channel blockade as an approach to insulin resistance," *Expert Opin. Ther. Targets* 9:571-579, Ashley Publications Ltd. (Jun. 2005).

Felix, J.P., et al., "Identification and Biochemical Characterization of a Novel Nortriterpene Inhibitor of the Human Lymphocyte Voltage-Gated Potassium Channel, Kv1.3," *Biochemistry* 38:4922-4930, American Chemical Society (1999).

Friedrich, M., et al., "Flow cytometric characterization of lesional T cells in psoriasis: intracellular cytokine and surface antigen expression indicates an activated, memory/effector type 1 immunophenotype," *Arch. Dermatol. Res.* 292:519-521, Springer-Verlag (2000).

Gewald, K., et al., "Synthesen von 4-Amino-thieno[2,3-*b*]pyridinen," *Monatshefte für Chemie* 110:1189-1196, Springer-Verlag (1979).

Gilis, P.M., et al., "Synthesis and antibacterial evaluation of 4,7-dihydro-4-oxothieno[2,3-b] pyridine-5-carboxylic acids," *Eur. J. Med. Chem. Chim. Ther.* 13:265-269, Editions Scientifiques Elsevier (1978).

Hanson, D.C., et al., "UK-78,282, a novel piperidine compound that potently blocks the Kv1.3 voltage-gated potassium channel and inhibits human T cell activation," *Br. J. Pharmacol.* 126:1707-1716, Stockton Press (1999).

Leonard, R.J., et al., "Selective blockers of voltage gated $K^+$ channels depolarize human T lymphocytes: Mechanism of the antiproliferative effect of charybdotoxin," *Proc. Natl. Acad. Sci. USA* 89:10094-10098, National Academy of Sciences (1992).

Marco, J.L., et al., "Synthesis and Acetylcholinesterase/Butyrylcholinesterase Inhibition Activity of 4-Amino-2,3-diaryl-5,6,7,8-tetrahydrofuro(and thieno)[2,3-*b*]-quinolines, and 4-Amino-5,6,7,8,9-pentahydro-2,3-diphenylcyclohepta[*e*]furo(and thieno)-[2,3-*b*] pyridines," *Arch. Pharm. Pharm. Med. Chem.* 335:347-353, Wiley-VCH GmbH & Co. (2002).

Meadows, H.J., et al., "Effect of SB-205384 on the decay of GABA-activated chloride currents in granule cells cultured from rat cerebellum," *Br. J. Pharmacol.* 121:1334-1338, Stockton Press (1997).

Nguyen, A., et al., "Novel Nonpeptide Agents Potently Block the C-Type Inactivated Conformation of Kv1.3 and Suppress T Cell Activation," *Mol. Pharmacol.* 50:1672-1679, American Society for Pharmacology and Experimental Therapeutics (1996).

O'Connor, K.C., et al., "The Neuroimmunology of Multiple Sclerosis: Possible Roles of T and B Lymphocytes in Immunopathogenesis," *J. Clin. Immunol.* 21:81-92, Plenum Publishing Corporation (2001).

Page, R.L. and Roden, D.M., "Drug Therapy for Atrial Fibrillation: Where Do We Go from Here?," *Nat. Rev. Drug Discov.* 4:899-910, Nature Publishing Group (Nov. 2005).

Schmitz, A., et al, "Design of PAP-1, a Selective Small Molecule Kv1.3 Blocker, for the Suppression of Effector Memory T Cells in Autoimmune Diseases," *Mol. Pharmacol.* 68:1254-1270, American Society for Pharmacology and Experimental Therapeutics (Nov. 2005).

Shah, K., et al., "Immunosuppressive effects of a Kv1.3 inhibitor," *Cell. Immunol.* 221:100-106, Elsevier Science (Feb. 2003).

Suzuki, M., et al., "Synthesis and Biological Evaluations of Condensed Pyridine and Condensed Pyrimidine-Based HMG-CoA Reductase Inhibitors," *Bioorg. Med. Chem. Lett.* 11:1285-1288, Elsevier Science Ltd (2001).

Valverde, P., et al., "Potassium Channel-blockers as Therapeutic Agents to Interfere with Bone Resorption of Periodontal Disease," *J. Dent. Res.* 84:488-499, International & American Associations for Dental Research (Jun. 2005).

Vennekamp, J., et al., "Kv1.3-Blocking 5-Phenylalkoxypsoralens: A New Class for Immunomodulators," *Mol. Pharmacol.* 65:1364-1374, American Society for Pharmacology and Experimental Therapeutics (Jun. 2004).

Viglietta, V., et al., "GAD65-reactive T cells are activated in patients with autoimmune type la diabetes," *J. Clin. Invest.* 109:895-903, American Society for Clinical Investigation (2002).

Wulff, H., et al., "Alkoxypsoralens, Novel Nonpeptide Blockers of *Shaker*-Type $K^+$ Channels: Synthesis and Photoreactivity," *J. Med. Chem.* 41:4542-4549, American Chemical Society (1998).

Wulff, H., et al., "Potassium channels as therapeutic targets for autoimmune disorders," *Curr. Opin. Drug Discov. Devel.* 6:640-647, Thomson Scientific (Sep. 2003).

Wulff, H., et al., "The voltage-gated Kv1.3 $K^+$ Channel in effector memory T cells as new targets for MS," *J. Clin. Invest.* 111:1703-1713, American Society for Clinical Investigation (Jun. 2003).

Wulff, H., et al., "K+ Channel Expression during B Cell Differentiation: Implications for Immunomodulation and Autoimmunity," *J. Immunol. 173*:776-786, American Association of Immunologists, Inc. (Jul. 2004).

Xu, J., et al., "The voltage-gated potassium channel Kv1.3 regulates peripheral insulin sensitivity," *Proc. Natl. Acad. Sci. USA 101*:3112-3117, National Academy of Sciences (Mar. 2004).

Yamashita, K., et al., "Severe chronic graft-versus host disease is characterized by a preponderance of CD4+ effector memory cells relative to central memory cells," *Blood 103*:3986-3988, American Society of Hematology (May 2004).

Yoon, J.-W. and Jun, H.-S., "Cellular and Molecular Pathogenic Mechanisms of Insulin-Dependent Diabetes Mellitus," *Ann. NY Acad. Sci. 928*:200-211, New York Academy of Sciences (2001).

International Search Report for International Application No. PCT/GB2004/002454, European Patent Office, Netherlands, mailed on Nov. 2, 2004.

Shieh, C.-C., et al., "Potassium Channels: Molecular Defects, Diseases, and Therapeutic Opportunities," *Pharmacol. Rev. 52*:557-593, American Society for Pharmacology and Experimental Therapeutics (2000).

Klemm, L.H., et al., "Chemistry of Thienopyridines. VIII. Substitution Products Derived from Thieno [2,3-*b*] pyridine 7-Oxide," *J. Heterocycl. Chem. 7*:81-89, Journal of Heterocyclic Chemistry (1970).

Klemm, L.H., and Merrill, R.E., "Chemistry of Thienopyridines. XIII. Selective Formation of Sulfones in Bi- and Tricyclic Systems. Thieno [2,3-*b*] pyridine 1,1-Dioxide as a Dienophile," *J Heterocycl. Chem. 9*:293-298, Journal of Heterocyclic Chemistry (1972).

Klemm, L.H., and Merrill, R.E., "Chemistry of Thienopyridines. XVIII. Lithiation as a Route to 2- and 3-Substituted Thieno [2,3-*b*]pyridines," *J. Heterocycl. Chem. 7*:355-361, Journal of Heterocyclic Chemistry (1974).

Klemm, L.H., and Harding, R., "Chemistry of Thienopyridines. XXIV. Two Transformations of Thieno [2,3-*b*] pyridine 7-Oxide," *J. Heterocyclic Chem. 13*:1197-1200, Journal of Heterocyclic Chemistry (1976).

Pedersen, E.B., and Carlsen, D., "Phosphoramides-V. Synthesis of 4,6-Bis(Dimethylamino)Thieno[2,3-b]Pyridines by an HMPT Induced Ring Closure Reaction," *Tetrahedron 33*:2089-2092, Pergamon Press (1977).

Sabnis, R.W., "The Gewald Synthesis," *Sulfur Reports 16*:1-17, Hardwood Academic Publishers GmbH (1994).

Schäfer, H., et al., "2-Arylamino-thiophen-3-carbonsäurederivate," *J. F. Prakt. Chemie 326*:917-928, Johann Ambrosius Barth Leipzig (1984).

English-language translation of JP 48-81893, published Nov. 1, 1973, Hisamitsu Pharmaceutical Co., Ltd.

Chandrakumar, N. S., Notice of Allowance and Fee(s) Due for U.S. Appl. No. 11/297,330, filed Dec. 9, 2005, U.S. Patent and Trademark Office, Alexandria, Virginia, mailed Apr. 9, 2009.

Chandrakumar, N. S., Office Action for U.S. Appl. No. 11/297,330, filed Dec. 9, 2005, U.S. Patent and Trademark Office, Alexandria, Virginia, mailed Nov. 21, 2008.

Chandrakumar, N. S., Office Action for U.S. Appl. No. 11/297,330, filed Dec. 9, 2005, U.S. Patent and Trademark Office, Alexandria, Virginia, mailed May 1, 2008.

Chandrakumar, N. S., Requirement for Restriction/Election for U.S. Appl. No. 11/297,330, filed Dec. 9, 2005, U.S. Patent and Trademark Office, Alexandria, Virginia, mailed Feb. 22, 2008.

Dialog File No. 351, Accession No. 1689342, Derwent WPI English language abstract for DE 28 31 677 A1 (Listed on accompanying PTO/SB/08A form as document FP38), Apr. 22, 2008.

Dialog File No. 351, Accession No. 197029, Derwent WPI English language abstract for DE 19 65 200 710 (Listed on accompanying PTO/SB/08A form as document FP37), Apr. 23, 2008.

English language abstract for Japanese Application Publication JP 3254843 (on attached form PTO/SB/08A as document FP42) STN Accession No. 1995:846501 Document No. 123:256681, Feb. 28, 1995.

English language abstract for Japanese Application Publication JP 07-076586 (on attached form PTO/SB/08A as document FP41) STN Accession No. 1995:662485 Document No. 123:55855 Mar. 20, 1995.

Feit, P.W. and Nielsen, O.B.T., "Aminobenzoic Acid Diureteics. 3,4-Disubstituted 5-Methylsulfonylbenzoic Acids and Related Compounds," *J. Med. Chem. 19*:402-406, American Chemical Society (1976).

Gewald reaction, Wikipedia, http://en.wikipeida.org/wiki/Gewald_reaction, 2 pages, accessed on Aug. 22, 2008.

Harb et al. STN Accession No. 1992:255564 Document No. 116:255564 Abstract of Bulletin of the Faculty of Science, Assiut University (1991), 20(2), 55-63.

International Search Report and Written Opinion for International Application No. PCT/GB2006/004594, European Patent Office, Netherlands, mailed on Jun. 19, 2007.

International Search Report and Written Opinion for International Patent Application No. PCT/GB2005/004753, European Patent Office, Netherlands, mailed Mar. 22, 2006.

Molina, P., et al., "An Efficient Iminophosphorane-Mediated Synthesis of Thieno[3,2-*c*]pyridine, Thieno[2,3-*c*]pyridine and Furo[3,2-*c*]-pyridine Derivatives," *Synthesis 1*:45-48, Thieme Chemistry (1987).

O'Dell, D.K., Office Action for U.S. Appl. No. 11/635,786, filed Dec. 8, 2008, U.S. Patent and Trademark Office Alexandria, Virginia, mailed Dec. 22, 2008.

O'Dell, D.K., Requirement for Restriction/Election for U.S. Appl. No. 11/635,786, filed Dec. 8, 2008, U.S. Patent and Trademark Office, Alexandria, Virginia, mailed Mar. 21, 2008.

Patani, G.A., et al., "Bioisosterism: A Rational Approach in Drug Design," *Chem. Rev. 96*:31-47-3176, (1996).

Shvedov et al. STN Original Reference No. 80:15419a, 15422a, Abstract of *Khimiya Geterotsiklicheskikh Soedinenii* (1974), (1), 58-60.

O'Dell, D.K., Office Action for U.S. Appl. No. 11/635,786, filed Dec. 8, 2006, U.S. Patent and Trademark Office, Alexandria, Virginia, mailed Oct. 13, 2009.

Chandrakumar, N.S. Office Action for U.S. Appl. No. 12/543,151, filed Aug. 18, 2009, U.S. Patent and Trademark Office, Alexandria, Virginia, mailed Jun. 28, 2010.

* cited by examiner

SUBSTITUTED THIENO[2,3-D]PYRIMIDINES AS POTASSIUM CHANNEL INHIBITORS

CROSS-REFERENCE TO RELATED APPLICATIONS

This application claims the benefit under 35 U.S.C. 119(e) of U.S. Provisional Application No. 60/477,518, filed on Jun. 11, 2003, herein incorporated by reference in its entirety.

The present invention relates to thienopyrimidine compounds which are potassium channel inhibitors. Pharmaceutical compositions comprising the compounds and their use in the treatment of arrhythmia are also provided.

Ion channels are proteins that span the lipid bilayer of the cell membrane and provide an aqueous pathway through which specific ions such as $Na^+$, $K^+$, $Ca^{2+}$ and $Cl^-$ can pass (Herbert, 1998). Potassium channels represent the largest and most diverse sub-group of ion channels and they play a central role in regulating the membrane potential and controlling cellular excitability (Armstrong & Hille, 1998). Potassium channels have been categorized into gene families based on their amino acid sequence and their biophysical properties (for nomenclature see Gutman et al., 2003).

Compounds which modulate potassium channels have multiple therapeutic applications in several disease areas including cardiovascular, neuronal, auditory, renal, metabolic and cell proliferation (Shieh et al., 2000; Ford et al., 2002). More specifically potassium channels such as Kv4.3, Kir2.1, hERG, KCNQ1/minK, and Kv1.5 are involved in the repolarisation phase of the action potential in cardiac myocytes. These potassium channels subtypes have been associated with cardiovascular diseases and disorders including long QT syndrome, hypertrophy, ventricular fibrillation, and atrial fibrillation, all of which can cause cardiac failure and fatality (Marban, 2002).

The human delayed rectifier voltage gated potassium channel subunit, Kv1.5, is exclusively expressed in atrial myocytes and is believed to offer therapeutic opportunities for the management of atrial fibrillation for several different reasons (see review of Brendel and Peukert, 2002): (i) There is evidence that Kv1.5 underlies the cardiac ultrarapid delayed rectifier ($Kv_{(ur)}$) physiological current in humans due to similar biophysical and pharmacological properties (Wang et al., 1993; and Fedida et al., 1993). This has been supported with antisense oligonucleotides to Kv1.5 which have been shown to reduce $Kv_{(ur)}$ amplitude in human atrial myocytes (Feng et al., 1997). (ii) electrophysiological recordings have demonstrated that $Kv_{(ur)}$ is selectively expressed in atrial myocytes, and therefore avoids inducing potentially fatal ventricular arrhythmia through interfering with ventricular repolarisation (Amos et al., 1996; Li et al., 1996; and Nattel, 2002). (iii) Inhibiting $Kv_{(ur)}$ in atrial fibrillation-type human atrial myocytes prolonged the action potential duration compared to normal healthy human atrial myocytes (Courtemanche et al., 1999). (iv) Prolonging the action potential duration by selectively inhibiting Kv1.5 could present safer pharmacological interventions for protecting against atrial re-entrant arrhythmias such as atrial fibrillation and atrial flutter compared to traditional class III antiarrythmics, by prolonging the atrial refractory period while leaving ventricular refractoriness unaltered (Nattel et al., 1999, Knobloch et al., 2002; and Wirth et al., 2003). Class III antiarrythmics have been widely reported as a preferred method for treating cardiac arrhythmias (Colatsky et al., 1990).

Traditional and novel class III antiarrythmic potassium channel blockers have been reported to have a mechanism of action by directly modulating Kv1.5 or $Kv_{(ur)}$. The known class III antiarrythmics ambasilide (Feng et al., 1997), quinidine (Wang et al., 1995), clofilium (Malayev et al., 1995) and bertosamil (Godreau et al., 2002) have all been reported as potassium channel blockers of $Kv_{(ur)}$ in human atrial myocytes. The novel benzopyran derivative, NIP-142, blocks Kv1.5 channels, prolongs the atrial refractory period and terminates atrial fibrillation and flutter in in vivo canine models (Matsuda et al., 2001), and 59947 inhibited Kv1.5 stably expressed in both *Xenopus oocytes* and Chinese hamster ovary (CHO) cells and $Kv_{(ur)}$ in native rat and human cardiac myocytes (Bachmann et al., 2001). Elsewhere, other novel potassium channel modulators which target Kv1.5 or $Kv_{(ur)}$ have been described for the treatment of cardiac arrhythmias, these include biphenyls (Peukert et al 2003), thiophene carboxylic acid amides (WO0248131), bisaryl derivatives (WO0244137, WO0246162), carbonamide derivatives (WO0100573, WO0125189) anthranillic acid amides (WO2002100825, WO02088073, WO02087568), dihydropyrimidines (WO0140231), cycloakyl derivatives (WO03063797), indane derivatives (WO0146155 WO9804521), tetralin benzocycloheptane derivatives (WO9937607), thiazolidone and metathiazanone derivatives (WO9962891), benzamide derivatives (WO0025774), isoquinoline derivatives (WO0224655), pyridazinone derivatives (WO9818475 WO9818476), chroman derivatives (WO9804542), benzopyran derivatives (WO0121610, WO03000675, WO0121609, WO0125224, WO02064581), benzoxazine derivatives (WO0012492), and the novel compound A1998 purified from Ocean material (Xu & Xu, 2000).

Thienopyrimidines have been reported to be useful as anti-inflammatory, anti-fungal, anti-osteoporosis and anti-microbial agents amongst others. Although also reported as cardiovascular agents (acting through modulation of the phosphodiesterase group of enzymes or through modulation of the sodium/proton exchange system), thienopyrimidines have not previously been reported as useful agents for modulating: ion channels.

Thieno[2,3-d]pyrimidines substituted in the 4-position with an optionally substituted benzylamine or phenethylamine moiety and in the 5-position with a methyl group may serve as anti-inflammatory or anti-osteoporosis agents (Katada et al., 1999). Such compounds were shown to modulate the activity of several cell types including leukocytes, which originate from hematopoietic precursor cells in the bone marrow. Increased activity in leukocytes can lead to various inflammatory diseases; therefore compounds cytotoxic to leukocytes could function as anti-inflammatory drugs. Such compounds are thought to suppress cellular activity by binding to integrins on the surface of leukocytes and preventing downstream cellular signalling events. Thieno[2,3-d]pyrimidines substituted in the 4-position with heteroarylthiols, aryl thiols, arylmethyl thiols, heteroarylamines, benzylamine, hydroxyl and chloro groups may also be useful anti-inflammatory agents (Stewart et al., 2001). This series of compounds were shown to inhibit induced expression of cell adhesion molecules on the luminal surface of vascular endothelial thus preventing the adhesion of leukocytes at the site of inflammation. Thieno[2,3-d]pyrimidines with a substituted hydrazine in the 4-position and a phenyl group in the 5 position (Hozien et al., 1996), tetrahydrobenzo[b]thieno[2,3-d]pyrimidines (Ismail et al., 1995), thieno[2,3-d]pyrimidines which have a hydrogen, chloro, hydrazine, heterocyclyl, amino, methyl, ethyl or phenyl group in the 2-position, an alkylamino, alkylarylamino, amino, dialkylamino or hydrazino substituent in the 4-position, a hydrogen or methyl group in the 5-position, a hydrogen, methyl acetamide or phenyl group in the 6-position or a tetramethylene in the 5,6-position (GB7549025), and the lead series of 5-phenyl- and 5,6-tetramethylenethieno[2,3-d]pyrimidines with methyl or phenyl in the 2-position and alkylamino or arylamino in the 4-position (Konno et al., 1989) have all been shown to have anti-microbial activity. Tetrahydrobenzothieno[2,3-d]pyrimidine with the 2-oxo-3-pyrrolidinylmethylene-hydrazino moiety in the 4-position showed some herbicidal activity against velvet leaf (Ram et al., 1981). It has also been reported that 4-chlorotetrahydrobenzothieno[2,3-d]pyrimidine is herbicidal, tetrahydrobenzothieno-[2,3-d]pyrimidines with a thiol, hydrazine, 2-fluoroanilino, 3-fluoroanilino or 4-diethylanilino substituent in the 4-position are bactericidal against *Streptococcus fecales* and tetrahyrobenzothieno[2,3-d]pyrimidines with a 2,4-dichlorobenzylamino or 2-fluoroanilino substituent in the 4-position are fungicidal against Pythium (Ram, 1979). Thieno[2,3-d]pyrimidines with a hydrogen, hydroxyl, thiol, halogen or cyano group in the 2-position, alkylamino, arylalkylamino or hydroxyalkyl amino groups in the 4-position, a hydrogen, alkyl or halogen in the 5- and/or 6-position or alkylene in the 5,6-position have been reported as tick-control agents (AU 521790).

Elsewhere, tetrahydrobenzo[b]thieno[2,3d]pyrimidines exhibited anti-tumour activity (Shehata et al., 1996) and analgesic activity half that of aspirin (Moneer et al., 1994), a series of thieno[2,3-d]pyrimidines with 4-alkylamino or arylamino, 5-H or 5-methyl, 6-methyl or 5,6-tetramethylene were shown to have potential as anticytokinins (Jordis et al., 1986), a series of 5,6-dimethyl-thieno[2,3-d]pyrimidines and 5,6-tetramethylenethieno[2,3-d]pyrimidines, both substituted in the 2-position with arylamines or heterocyclic amines and in the 4-position with arylamines displayed blood platelet aggregation inhibiting properties (DD 226893), pyrano- and thiopyrano[3,4-b]thieno[5,4-d]pyrimidines with the 4-position substituted with amino, butylamine, aniline, cyclohexylamine, benzylamine, phenethylamine and 2-hydroxyethylamine have been reported to exhibit anticonvulsive activity (Noravyan et al., 1977), and 4-[(Benzo-2,1,3-thiadiazolyl-4)amino]-5,6,7,8-tetrahydrobenzothieno-(2,3-d)-pyrimidine has been reported to possess anthelmintic activity in larval alveolar echinococcosis (RU 2116309).

Thieno[2,3-d]pyrimidines with a substituted amino group at the 4-position, hydrogen, alkyl or halo substitution at the 5 and 6-positions and an alkyl chain at the 2-position are claimed to be inhibitors of phosphodiesterase V and useful in the treatment of cardiovascular diseases and for disturbances in potency (DE10104802).

Elsewhere, 5-alkyl thieno[2,3-d]pyrimidines with a piperazinyl substituent at the 4-position were found to be inhibitors of the sodium/proton exchanger and useful in the treatment of various cardiovascular disorders, including angina pectoris and arrhythmia (WO 01/27107).

4-[(Phenyl)amino]-thieno[2,3-d]pyrimidines bearing a 5-thiophenyl substituent and a 2-methyl substituent were found to have molluscicidal activity (Hosni et al, Acta Poloniae Pharmaceutica, 1999, 56(1), 49-56).

Recently thienopyrimidines have also been reported as potent VEGFR inhibitors (Munchhof, 2004).

Several publications disclose compounds which are indicated as acting on potassium channels. Thus, U.S. Pat. No. 6,531,495 discloses 2'-aminomethylbiphenyl-2-carboxamides, WO2002/100825 discloses anthranillic acid amides as antiarrhythmics and WO2002/036556 discloses acylaminoalkylbenzenesulfonamides as cardiovascular agents.

This invention provides compounds that are potassium channel inhibitors. These compounds are particularly useful for inhibiting potassium channels Kv1.5 or Kv$_{(ur)}$, which are known targets for the treatment of cardiac arrhythmia in the atria such as atrial fibrillation (Nattel et al., 1999; Wang et al., 1993). This invention is not limited to treating cardiac arrhythmias, the compounds also being useful to treat diseases which require potassium channel inhibition (e.g. Shieh et al., 2000; Ford et al., 2002). Thus, in a first aspect, the present invention provides a compound of formula (I)

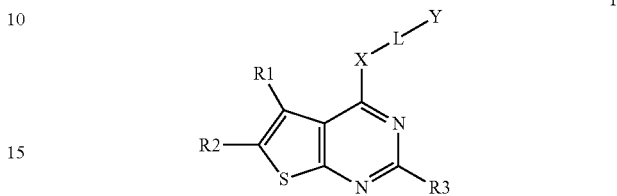

Wherein
R1 is aryl, heteroaryl, cycloalkyl or alkyl;
R2 is H, alkyl, nitro, $CO_2R7$, C(O)NR4R5 or halo;
R3 is H, NR4R5, NC(O)R8, halo, trifluoromethyl, alkyl, nitrile or alkoxy;
R4 and R5 may be the same or different, and may be H, alkyl, aryl, heteroaryl or cycloalkyl; or R4 and R5 may together form a saturated, unsaturated or partially saturated 4 to 7 member ring, wherein said ring may optionally comprise one or more further heteroatoms selected from N, O or S;
X is O, S or NR6;
R6 is H or alkyl;
R7 is hydrogen, methyl or ethyl;
R8 is methyl or ethyl;
L is $(CH_2)_n$, where n is 1, 2 or 3; and
Y is aryl, a heterocyclic group, alkyl, alkenyl or cycloalkyl;
or pharmaceutically acceptable salts thereof;
with the proviso that when Y is phenyl, phenyl monosubstituted by Cl or methoxy, furanyl, tetrahydrofurayl, pyrimidinyl, pyrrolidinyl or 1,3-benzodioxolyl, then R1 is not phenyl, phenyl monosubstituted by halogen or phenyl substituted by methyl;
and wherein the compound is not:
N-Butyl-5-phenylthieno[2,3-d]pyrimidin-4-amine;
5-Phenyl-N-(pyridin-2-ylmethyl)thieno[2,3-d]pyrimidin-4-amine;
5-(4-Chlorophenyl)-N-[3-(1H-imidazol-1-yl)propyl]thieno[2,3-d]pyrimidin-4-amine;
5-(4-Chlorophenyl)-N-(pyridin-2-ylmethyl)thieno[2,3-d]pyrimidin-4-amine;
5-(4-Chlorophenyl)-N-(2-cyclohex-1-en-1-ylethyl)thieno[2,3-d]pyrimidin-4-amine;
5-(4-Chlorophenyl)-N-(pyridin-3-ylmethyl)thieno[2,3-d]pyrimidin-4-amine;
5-(4-Chlorophenyl)-N-(2-furylmethyl)thieno[2,3-d]pyrimidin-4-amine;
5-(4-Fluorophenyl)-N-(pyridin-3-ylmethyl)thieno[2,3-d]pyrimidin-4-amine;
N-Allyl-5-phenylthieno[2,3-d]pyrimidin-4-amine;
5-(4-Methylphenyl)-N-(2-thien-2-ylethyl)thieno[2,3-d]pyrimidin-4-amine;
N-(2-Furylmethyl)-5-phenylthieno[2,3-d]pyrimidin-4-amine;
5-(4-Chlorophenyl)-N-(2-thien-2-ylethyl)thieno[2,3-d]pyrimidin-4-amine;
5-(4-Fluorophenyl)-N-(2-thien-2-ylethyl)thieno[2,3-d]pyrimidin-4-amine;

N-Allyl-5-(4-chlorophenyl)thieno[2,3-d]pyrimidin-4-amine;
5-(4-Chlorophenyl)-N-(tetrahydrofuran-2-ylmethyl)thieno[2,3-d]pyrimidin-4-amine;
5-Phenyl-N-(tetrahydrofuran-2-ylmethyl)thieno[2,3-d]pyrimidin-4-amine;
5-(4-Bromophenyl)-N-(pyridin-3-ylmethyl)thieno[2,3-d]pyrimidin-4-amine;
N-[3-(1H-Imidazol-1-yl)propyl]-5-phenylthieno[2,3-d]pyrimidin-4-amine;
1-(2-{[5-(4-Methylphenyl)thieno[2,3-d]pyrimidin-4-yl]amino}ethyl)imidazolidin-2-one; or
N-(2-Furylmethyl)-5-(4-methylphenyl)thieno[2,3-d]pyrimidin-4-amine.

As used herein, an alkyl group or moiety is typically a linear or branched alkyl group or moiety containing from 1 to 6 carbon atoms, such as a $C_1$-$C_4$ alkyl group or moiety, for example methyl, ethyl, n-propyl, i-propyl, butyl, i-butyl and t-butyl. An alkyl group or moiety may be unsubstituted or substituted at any position. Typically, it is unsubstituted or carries one or two substituents. Suitable substituents include halogen, cyano, nitro, NR9R10, alkoxy, hydroxyl, unsubstituted aryl, unsubstituted heteroaryl, $CO_2R7$, C(O)NR9R10, NC(O)R8 and $SO_2NR9R10$.

As used herein, an aryl group is typically a $C_6$-$C_{10}$ aryl group such as phenyl or napthyl. A preferred aryl group is phenyl. An aryl group may be unsubstituted or substituted at any position. Typically, it carries 1, 2, 3 or 4 substituents. Suitable substituents include cyano, halogen, nitro, trifluoromethyl, alkyl, alkylthio, alkoxy, NR9R10, $CO_2R7$, C(O)NR9R10, NC(O)R8 and $SO_2NR9R10$ and hydroxyl.

As used herein, a heterocyclic group is a heteroaryl group, typically a 5- to 10-membered aromatic ring, such as a 5- or 6-membered ring, containing at least one heteroatom selected from O, S and N. Examples include pyridyl, pyrazinyl, pyrimidinyl, pyridazinyl, furanyl, thienyl, pyrazolidinyl, pyrrolyl and pyrazolyl groups. Preferred heteroaryl groups are furanyl, thienyl and pyridyl. Examples of polycyclic heterocycles include indolyl, benzofuranyl, benzothiophenyl and benzodioxolyl. Non-aryl heterocyclic groups are also included, such as tetrahydrofuranyl or pyrrolidinyl. A heterocyclic group may be unsubstituted or substituted at any position. Suitable substituents include cyano, nitro, halogen, alkyl, alkylthio, alkoxy, NR9R10, $CO_2R7$, C(O)NR9R10, NC(O)R8 and $SO_2NR9R10$ and hydroxyl.

R9 and R10 can be the same or different, and may be selected from H, unsubstituted alkyl, unsubstituted aryl, unsubstituted heteroaryl, unsubstituted cycloalkyl, aminoethyl, methylaminoethyl, dimethylaminoethyl, hydroxyethyl, alkoxyethyl, or R9 and R10 may together form a saturated, unsaturated or partially saturated 4 to 7 member ring.

When R4 and R5 or R9 and R10 together form a saturated, unsaturated or partially saturated 4 to 7 member ring, the ring may optionally comprise one, two, or three further heteroatoms.

As used herein, alkoxy means $C_{1-3}$ alkoxy, cycloalkyl means $C_{3-6}$ cycloalkyl and halogen means Cl, F, Br, or I, preferably Cl, F or Br.

Preferred compounds of formula I are those wherein R1 is aryl or heteroaryl, R2 is H or alkyl, R3 is H, NR4R5, alkoxy or alkyl, X is O or NR6, R6 is H, n is 1 or 2 and Y is alkyl, cycloalkyl, aryl or heteroaryl.

More preferred compounds of formula I are those wherein R1 is aryl or heteroaryl, R2 is H or methyl, R3 is H, NR4R5, alkoxy or alkyl, X is NR6, R6 is H, n is 1 and Y is heteroaryl.

Preferably Y is furanyl, thienyl or pyridyl. More preferably Y is optionally substituted furan-2-yl or optionally substituted pyridin-2-yl.

Preferred compounds include:
2-{5-Phenyl-4-[(pyridin-2-ylmethyl)-amino]-thieno[2,3-d]pyrimidin-2-yl}-propane-1,3-diol;
2-{5-(4-Fluorophenyl)-4-[(pyridin-2-ylmethyl)-amino]-thieno[2,3-d]pyrimidin-2-ylamino}-ethanol;
Pyridin-2-ylmethyl-(5-p-tolyl-thieno[2,3-d]pyrimidin-4-yl)-amine;
2-{5-Phenyl-4-[(pyridin-2-ylmethyl)-amino]-thieno[2,3-d]pyrimidin-2-ylamino}-ethanol;
2-{5-Phenyl-4-[(pyridin-2-ylmethyl)amino]thieno[2,3-d]pyrimidin-2-yl}ethanol;
2-((2-Hydroxy-ethyl)-{5-phenyl-4-[(pyridin-2-ylmethyl)-amino]-thieno[2,3-d]pyrimidin-2-yl}-amino)-ethanol;
2-Methyl-N-(2-pyridyl)methyl-5-phenylthieno[2,3-d]pyrimidin-4-ylamine;
2-{4-[(Furan-2-ylmethyl)-amino]-5-phenyl-thieno[2,3-d]pyrimidin-2-yl}-ethanol;
[2-(2-Methoxy-ethoxy)-5-phenyl-thieno[2,3-d]pyrimidin-4-yl]-pyridin-2-ylmethyl-amine;
(2-Methoxy-5-phenyl-thieno[2,3-d]pyrimidin-4-yl)-pyridin-2-ylmethyl-amine;
5-(4-Fluorophenyl)-$N^2$-(2-methoxy-ethyl)-$N^4$-pyridin-2-ylmethyl-thieno[2,3-d]pyrimidine-2,4-diamine;
[5-(4-Dimethylamino-phenyl)-thieno[2,3-d]pyrimidin-4-yl]-pyridin-2-ylmethyl-amine;
5-(4-Fluorophenyl)-$N^2,N^2$-dimethyl-$N^4$-pyridin-2-ylmethyl-thieno[2,3-d]pyrimidine-2,4-diamine;
Pyridin-2-ylmethyl-[5-(4-trifluoromethyl-phenyl)-thieno[2,3-d]pyrimidin-4-yl]-amine;
[5-(1H-Indol-6-yl)-thieno[2,3-d]pyrimidin-4-yl]-pyridin-2-ylmethyl-amine;
(5-Benzo[1,3]dioxol-5-yl-thieno[2,3-d]pyrimidin-4-yl)-pyridin-2-ylmethyl-amine;
2-{5-Phenyl-4-[(pyridin-2-ylmethyl)-amino]-thieno[2,3-d]pyrimidin-2-ylamino}-propane-1,3-diol;
3-{5-Phenyl-4-[(pyridin-2-ylmethyl)-amino]-thieno[2,3-d]pyrimidin-2-ylamino}-propane-1,2-diol;
N-Methyl-2-{5-phenyl-4-[(pyridin-2-ylmethyl)amino]thieno[2,3-d]pyrimidin-2-yl}acetamide; or
6-Methyl-N-[(6-methylpyridin-2-yl)methyl]-5-phenylthieno[2,3-d]pyrimidin-4-amine;
and pharmaceutically acceptable salts thereof.

Compounds of formula I wherein R3 is H, alkyl or trifluoroalkyl are synthesised from a compound of formula II by reaction with a suitable nucleophile X-L-Y, where X, Y and L are as defined herein, optionally in the presence of a solvent and a base, and optionally at elevated temperature or with microwave irradiation. Preferably the solvent (if present) is an alcohol, preferably ethanol, and the base is a hindered nitrogen base such as triethylamine. If a solvent is present the reaction is carried out at the reflux temperature of the solvent, or under sealed conditions and with microwave irradiation at a temperature of 120-160° C.

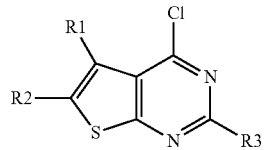

II

A compound of formula II may be obtained from a compound of formula III by reaction with a chlorinating reagent such as phenylphosphonic dichloride or phosphorous oxychloride in a suitable solvent or no solvent, and with heating. Preferably the chlorinating reagent is phosphorous oxychloride and the reaction is carried out at reflux temperature and in the absence of additional solvent.

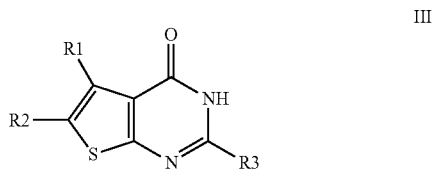

III

Compounds of formula III may be obtained by the reaction of a compound of formula IV with a suitable substituted or unsubstituted amidine of formula V, or its salt equivalent. The reaction may be carried out in the presence of a suitable solvent at elevated temperature. Preferably the solvent is ethanol and the reaction is carried out under reflux conditions.

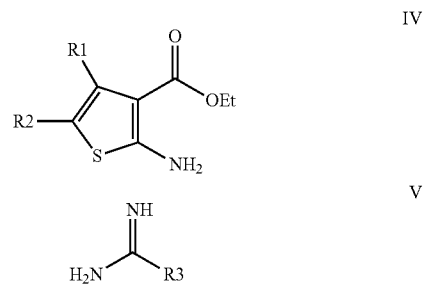

IV

V

In an alternative synthesis of compounds of formula III, also applicable to those examples wherein R3 is an alkyl group, reaction of a compound of formula VI under basic conditions in a suitable solvent is performed. Suitable bases include alkali metal alkoxides such as sodium methoxide. Suitable solvents include alcohols such as methanol.

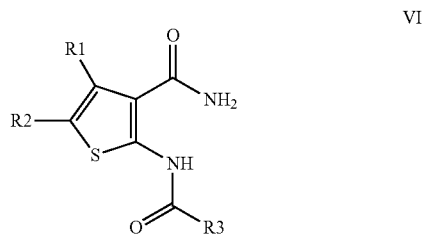

VI

A compound of formula VI can be prepared by reaction of a compound of formula VII under acylating conditions, for example in the presence of an acid chloride and a base. Exemplified acid chlorides include acetyl chloride. Suitable bases include the nitrogenous bases such as triethylamine and pyridine.

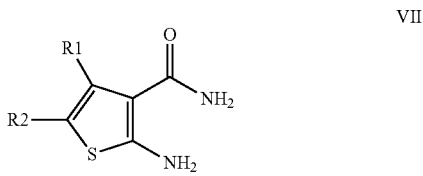

VII

Compounds of formula VII are widely available from standard commercial sources or may be obtained from compounds of formula IV by simple functional group interconversions.

Compounds of formula V are widely available from standard commercial sources or can be synthesised by routine organic chemistry procedures.

A compound of formula IV can be prepared by reaction of a compound of formula VIII, under basic conditions and in a suitable solvent, with powdered sulphur. Preferably the base is diethylamine and the reaction is carried out at 25 to 65° C. The solvent may be an alcohol, preferably ethanol.

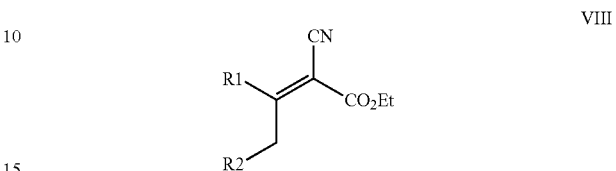

VIII

Compounds of formula VIII can be prepared by heating a compound of formula IX with ethylcyanoacetate (NCCH$_2$CO$_2$Et) in the presence of an acid and ammonium acetate in a suitable solvent, optionally with azeotropic water removal. Preferably the acid is acetic acid.

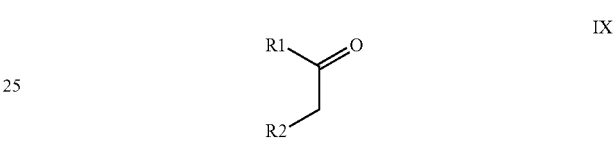

IX

Compounds of formula IX are widely available from commercial sources or can be readily synthesised using standard synthetic organic chemistry procedures.

Alternatively, compounds of formula I wherein R3 is other than H, alkyl or trifluoroalkyl, can be prepared from a compound of formula X by displacement of the 2-chloro substituent with a suitable nucleophilic species. Such a reaction may be carried out with heating or microwave irradiation.

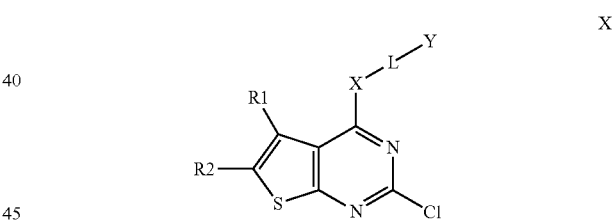

X

Compounds of formula X are readily synthesised from compounds of formula XI by reaction with a suitable nucleophile X-L-Y, optionally in the presence of a solvent and a base, and optionally at elevated temperature or with microwave irradiation. Preferably the solvent (if present) is an alcohol, preferably propan-2-ol, and the base is a hindered nitrogen base such as triethylamine. The reaction is carried out at ambient temperatures.

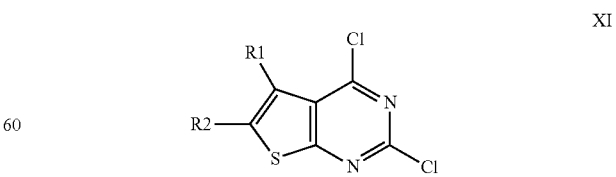

XI

A compound of formula XI may be synthesised by reaction of a compound of formula XII with a chlorinating reagent such as phenylphosphonic dichloride or phosphorous oxychloride.

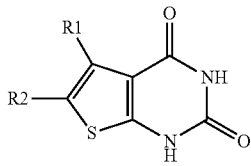

XII

Compounds of formula XII are available by the reaction of a compound of formula IV with an alkali metal cyanate, preferably potassium cyanate.

Alternatively, compounds of formula I wherein R3 is an ester-substituted alkyl group, in particular an acetic acid ester, can be prepared by the reaction of a compound of formula XIII, by reaction with a suitable nucleophile X-L-Y optionally in the presence of a solvent and a base, and optionally at elevated temperature or with microwave irradiation. Preferably the solvent (if present) is an alcohol, preferably ethanol, and the base is a hindered nitrogen base such as triethylamine. If a solvent is present the reaction is carried out at the reflux temperature of the solvent, or under sealed conditions and with microwave irradiation at a temperature of 120-160° C.

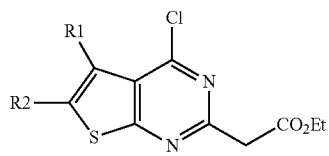

XIII

Compounds of formula XIII may be synthesized from compounds of formula XIV by reaction with a chlorinating reagent such as phenylphosphonic dichloride or phosphorous oxychloride.

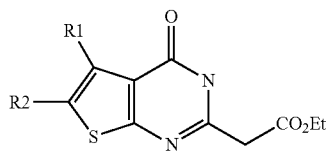

XIV

Compounds of formula XIV are synthesized by reaction of compounds of formula IV with ethyl cyanoacetate, performed under acidic conditions with or without the presence of solvent. Suitable acids include gaseous hydrogen chloride.

It is understood that compounds of formula I wherein R3 is a carboethoxy group may undergo functional group transformation of the ester moiety using methods familiar to those skilled in the art. In a preferred instance such compounds may undergo amidation by reaction with an alkyl or dialkylamine. In another preferred instance compounds of formula I wherein R3 is a 1-hydroxyethyl group can be prepared by reaction with a reducing agent such as diisobutylaluminium hydride or lithium aluminium hydride. In a further instance compounds of formula I wherein R3 is a carboethoxy group may be reacted with a dialkyl carbonate under basic conditions to provide a compound of formula I wherein R3 is a dialkylmalonyl group. Such compounds may be reduced, preferably with a reducing agent such as diisobutylaluminium hydride or lithium aluminium hydride, to provide compounds of formula I wherein R3 is a propanediol group.

Compounds of formula I wherein R3 is a chloromethyl group may be synthesized from compounds of formula XV by reaction with a suitable nucleophile X-L-Y optionally in the presence of a solvent and a base, and optionally at elevated temperature or with microwave irradiation. Preferably the solvent (if present) is an alcohol, preferably propan-2-ol, and the base is a hindered nitrogen base such as triethylamine. The reaction is carried out at ambient temperature.

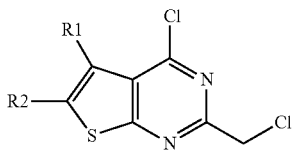

XV

Compounds of formula XV may be synthesized from compounds of formula XVI by reaction with a chlorinating reagent such as phenylphosphonic dichloride or phosphorous oxychloride.

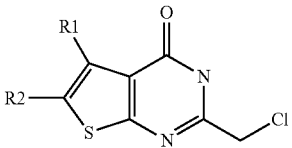

XVI

Compounds of formula XVI may be synthesized by reaction of a compound of formula IV under acidic conditions in a suitable solvent with chloroacetonitrile. Suitable acids include gaseous hydrogen chloride. Suitable solvents include alkyl ethers such as 1,4-dioxane.

It is understood that compounds of formula I wherein R3 is a chloromethyl group may undergo standard functional group transformations of the chloromethyl moiety using methods familiar to those skilled in the art. In a preferred instance reaction with a nucleophile is carried out. Suitable nucleophiles may include an alkyl or dialkyl amine, an alcohol or a thiol, or anion derivatives thereof.

In an alternative synthesis of compounds of formula I, particularly applicable to those examples wherein R1 comprises an aryl or heteroaryl group, a compound of formula XVII is reacted with an aryl or heteroaryl boronic acid, preferably under coupling conditions such as in the presence of a palladium(0) catalyst, preferably tetrakis(triphenylphosphine) palladium(0) which may be generated in situ or attached to a polymer resin. Alternative coupling conditions will be familiar to those skilled in the art. If a solvent is present the reaction is carried out at the reflux temperature of the solvent, or under sealed conditions and with microwave irradiation at a temperature of 120-160° C.

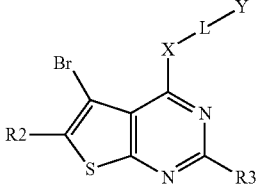

XVII

A compound of formula XVII may be synthesised from a compound of formula XVIII by reaction with a suitable nucleophile X-L-Y optionally in the presence of a solvent and a base, and optionally at elevated temperature or with microwave irradiation. Preferably the solvent (if present) is an alcohol, preferably ethanol, and the base is a hindered nitrogen base such as triethylamine. If a solvent is present the reaction is carried out at the reflux temperature of the solvent, or under sealed conditions and with microwave irradiation at a temperature of 120-160° C.

XVIII

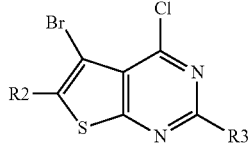

Compounds of formula XVIII wherein R2 is H may be synthesized by reaction of a compound of formula XIX under basic conditions at reduced temperature in a suitable solvent. Preferably the base is an alkyllithium, in the most preferred instance lithium diisopropylamide and the solvent is an alkylether, in the most preferred instance tetrahydrofuran. The reaction may be carried out from −80° C. to ambient temperature.

XIX

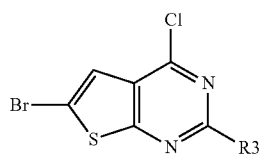

A compound of formula XIX may be obtained from a compound of formula XX by reaction with a chlorinating reagent such as phenylphosphonic dichloride or phosphorous oxychloride in a suitable solvent or no solvent, and with heating. Preferably the chlorinating reagent is phosphorous oxychloride and the reaction is carried out at reflux temperature and in the absence of additional solvent.

XX

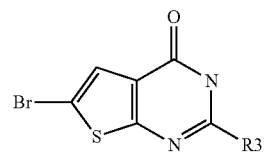

Compounds of formula XX may be synthesized by reactions of compounds of formula III wherein R1 is H and R2 is H with an electrophilic halogenating reagent preferably bromine in a suitable solvent preferably glacial acetic acid.

Alternatively, compounds of formula XVIII wherein R3 is other than H, alkyl or trifluoroalkyl and R2 is other than hydrogen may be synthesized from compounds of formula XXI by displacement of the 2-chloro substituent with a suitable nucleophilic species. Such a reaction may be carried out with heating or microwave irradiation.

XXI

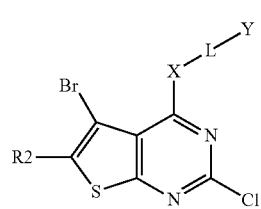

Compounds of formula XXI are readily synthesised from compounds of formula XXII by reaction with a suitable nucleophile X-L-Y, optionally in the presence of a solvent and a base, and optionally at elevated temperature or with microwave irradiation. Preferably the solvent (if present) is an alcohol, preferably ethanol, and the base is a hindered nitrogen base such as triethylamine.

XXII

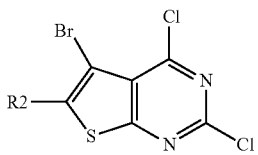

A compound of formula XXII may be synthesised by reaction of a compound of formula XXIII with a chlorinating reagent such as phenylphosphonic dichloride or phosphorous oxychloride.

XXIII

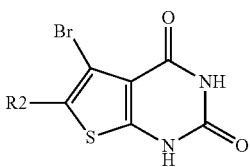

A compound of formula XXIII may be synthesized by reaction of a compound of formula XII wherein R1 is H and R2 is alkyl with an electrophilic halogenating reagent, preferably bromine, in a suitable solvent, preferably glacial acetic acid.

Many of the starting materials referred to in the reactions described above are available from commercial sources or can be made by methods cited in the literature references. Synthetic methods can also be found in reviews; thiophenes for example can be found in references cited in Comprehensive Heterocyclic Chemistry, Eds Katritzky, A. R., Rees, C. R., (4), 863-934, and Comprehensive Heterocyclic Chemistry (II), Eds Katritzky, A. R., Rees, C. W., Scriven, E. F. V., (2). 607-678.

| Suitable starting materials include: | | |
|---|---|---|
| Material | Reference | Supplier |
| Formamidine Hydrochloride | 26,860-7 | Aldrich |
| 2-Methyl Propionamidine | M23802 | Tyger |
| Acetamidine Hydrochloride | 15,915-8 | Aldrich |
| Trifluoroacetamidine | 12422 | Lancaster |
| 4-Fluoroacetophenone | F-320-7 | Aldrich |
| Acetophenone | A1 070-1 | Aldrich |
| 2-Methylacetophenone | M2,659-3 | Aldrich |
| 3,4-Dimethylacetophenone | 13,723-5 | Aldrich |
| 4-Methylacetophenone | M2,661-5 | Aldrich |
| 2-Acetylpyridine | A2,100-2 | Aldrich |
| 2-Acetyl-4-methylpyridine | 49,923-4 | Aldrich |
| 3-Acetylpyridine | A2,120-7 | Aldrich |
| 3-Acetylthiophene | 19,632-0 | Aldrich |
| 2-Acetylthiophene | A2,260-2 | Aldrich |
| 2-Acetylfuran | A1,625-4 | Aldrich |
| Furfurylamine | F2,000-9 | Aldrich |
| Benzylamine | B1,630-5 | Aldrich |
| 2-(Aminomethyl)pyridine | A6,520-4 | Aldrich |

-continued

Suitable starting materials include:

| Material | Reference | Supplier |
| --- | --- | --- |
| 2-Pyridinemethanol | P6,660-2 | Aldrich |
| Propiophenone | P5,160-5 | Aldrich |
| N-Butyrophenone | 12,433-8 | Aldrich |
| 4-Chloro-5-(2-thienyl)thieno[2,3d]pyrimidine[2,3-d]pyrimidine | AW00007 | Maybridge |
| 4-Chloro-5-phenylthieno[2,3d]pyrimidine[2,3-d]pyrimidine | 30\08-39 | Buttpark |
| 4-Chloro-5-(4-chlorophenyl)thieno[2,3d]pyrimidine[2,3-d]pyrimidine | 17097 | Fluorochem |
| Ethyl-2-cyano-3-phenyl-2-butenoate | 39,875-6 | Aldrich |
| 4-Fluorophenylboronic acid | 41,755-6 | Aldrich |
| 4-Trifluoromethylphenylboronic acid | 43,932-0 | Aldrich |
| 3,4-Methylenedioxyphenylboronic acid | 49,999-4 | Aldrich |
| Phenylboronic acid | P2,000-9 | Aldrich |
| 4-Methoxyphenylboronic acid | M1,920-1 | Aldrich |
| 2-Amino-4-phenylthiophene-3-carboxamide | B014343 | Art-Chem-BB |
| 2-Amino-4-(4-fluorophenyl)-5-methylthiophene-3-carboxamide | B006163 | Art-Chem-BB |
| 2-Amino-5-methyl-4-phenylthiophene-3-carboxamide | B014344 | Art-Chem-BB |

As discussed herein, the compounds of the invention are useful in the treatment of various conditions. Thus, in a second aspect, the present invention provides a pharmaceutical formulation comprising at least one compound and optionally one or more excipients, carriers or diluents; wherein said compound has the formula:

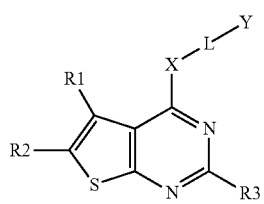

Wherein
R1 is aryl, heteroaryl, cycloalkyl or alkyl;
R2 is H, alkyl, nitro, $CO_2R7$, $CONR4R5$ or halo;
R3 is H, NR4R5, NC(O)R8, halo, trifluoromethyl, alkyl, nitrile or alkoxy;
R4 and R5 may be the same or different, and may be H, alkyl, aryl, heteroaryl or cycloalkyl; or R4 and R5 may together form a saturated, unsaturated or partially saturated 4 to 7 member ring, wherein said ring may optionally comprise one or more further heteroatoms selected from N, O or S;
X is O, S or NR6;
R6 is H or alkyl;
R7 is hydrogen, methyl or ethyl;
R8 is methyl or ethyl;
L is $(CH_2)_n$, where n is 1, 2 or 3; and
Y is aryl, a heterocyclic group, alkyl, alkenyl or cycloalkyl; or pharmaceutically acceptable salts thereof;
with the proviso that when Y is phenyl, phenyl monosubstituted by Cl or methoxy, furanyl, tetrahydrofurayl, pyrimidinyl, pyrrolidinyl or 1,3-benzodioxolyl, then R1 is not phenyl, phenyl monosubstituted by halogen or phenyl substituted by methyl.

Preferably the compound is a compound as described in the first aspect.

The compositions of the invention may be presented in unit dose forms containing a predetermined amount of each active ingredient per dose. Such a unit may be adapted to provide 5-100 mg/day of the compound, preferably either 5-15 mg/day, 10-30 mg/day, 25-50 mg/day 40-80 mg/day or 60-100 mg/day. For compounds of formula I, doses in the range 100-1000 mg/day are provided, preferably either 100-400 mg/day, 300-600 mg/day or 500-1000 mg/day. Such doses can be provided in a single dose or as a number of discrete doses. The ultimate dose will depend on the condition being treated, the route of administration and the age, weight and condition of the patient and will be at the doctor's discretion.

The compositions of the invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For applications to the eye or other external tissues, for example the mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use.

Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

In a further aspect the present invention provides a compound, or a pharmaceutical composition comprising said compound for use in medicine, wherein said compound has the formula:

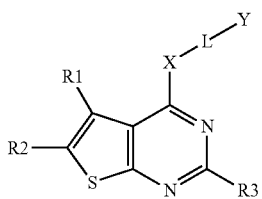

Wherein
R1 is aryl, heteroaryl, cycloalkyl or alkyl;
R2 is H, alkyl, nitro, $CO_2R7$, CONR4R5 or halo;
R3 is H, NR4R5, NC(O)R8, halo, trifluoromethyl, alkyl, nitrile or alkoxy;
R4 and R5 may be the same or different, and may be H, alkyl, aryl, heteroaryl or cycloalkyl; or R4 and R5 may together form a saturated, unsaturated or partially saturated 4 to 7 member ring, wherein said ring may optionally comprise one or more further heteroatoms selected from N, O or S;
X is O, S or NR6;
R6 is H or alkyl;
R7 is hydrogen, methyl or ethyl;
R8 is methyl or ethyl;
L is $(CH_2)_n$, where n is 1, 2 or 3; and
Y is aryl, a heterocyclic group, alkyl, alkenyl or cycloalkyl;
or pharmaceutically acceptable salts thereof;
with the proviso that when Y is phenyl, phenyl monosubstituted by Cl or methoxy, furanyl, tetrahydrofurayl, pyrimidinyl, pyrrolidinyl or 1,3-benzodioxolyl, then R1 is not phenyl, phenyl monosubstituted by halogen or phenyl substituted by methyl.

Preferably, the compound is a compound of the first aspect.

The compositions of the invention can be used to treat conditions which require inhibition of potassium channels, for example in the treatment of arrhythmia. Thus, in further aspects, the present invention provides:

(i) a method of treating or preventing a disorder which requires potassium channel inhibition, eg arrhythmia, comprising administering to a subject an effective amount of at least one compound or of a pharmaceutical composition comprising said at least one compound and optionally one or more excipients, diluents and/or carriers wherein said compound has the formula:

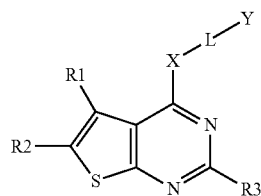

Wherein
R1 is aryl, heteroaryl, cycloalkyl or alkyl;
R2 is H, alkyl, nitro, $CO_2R7$, CONR4R5 or halo;
R3 is H, NR4R5, NC(O)R8, halo, trifluoromethyl, alkyl, nitrile or alkoxy;
R4 and R5 may be the same or different, and may be H, alkyl, aryl, heteroaryl or cycloalkyl; or R4 and R5 may together form a saturated, unsaturated or partially saturated 4 to 7 member ring, wherein said ring may optionally comprise one or more further heteroatoms selected from N, O or S;
X is O, S or NR6;
R6 is H or alkyl;
R7 is hydrogen, methyl or ethyl;
R8 is methyl or ethyl;
L is $(CH_2)_n$, where n is 1, 2 or 3; and
Y is aryl, a heterocyclic group, alkyl, alkenyl or cycloalkyl;
or pharmaceutically acceptable salts thereof; and (ii) the use of a compound of the invention in the manufacture of a medicament for use in potassium channel inhibition; wherein the compound has the formula:

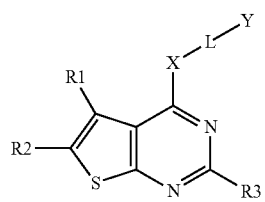

Wherein
R1 is aryl, heteroaryl, cycloalkyl or alkyl;
R2 is H, alkyl, nitro, $CO_2R7$, CONR4R5 or halo;
R3 is H, NR4R5, NC(O)R8, halo, trifluoromethyl, alkyl, nitrile or alkoxy;
R4 and R5 may be the same or different, and may be H, alkyl, aryl, heteroaryl or cycloalkyl; or R4 and R5 may together form a saturated, unsaturated or partially saturated 4 to 7 member ring, wherein said ring may optionally comprise one or more further heteroatoms selected from N, O or S;
X is O, S or NR6;
R6 is H or alkyl;
R7 is hydrogen, methyl or ethyl;
R8 is methyl or ethyl;

L is (CH$_2$)$_n$, where n is 1, 2 or 3; and

Y is aryl, a heterocyclic group, alkyl, alkenyl or cycloalkyl; or pharmaceutically acceptable salts thereof.

In particular, the medicament is for use in the treatment or prevention of arrhythmia.

Preferably the compounds are compounds of the first aspect.

EXAMPLES

Using the information outlined herein the following compounds can be synthesised which are given by way of example only. The pharmacological profile of compounds of the present invention can readily be assessed by those skilled in the art using routine experimentation, such as procedures and techniques illustrated herein and described in detail in Ford et al., 2002.

Example 1

2-Cyano-3-phenyl-but-2-enoic acid ethyl ester

A stirred mixture of acetophenone (180 g, 1.5 mol), ethyl cyanoacetate (170 g, 1.3 mol), ammonium acetate (23.1 g), acetic acid (72 g) and toluene (300 ml) was heated under reflux for 18 hours while water was removed from the reaction by azeotropic distillation. The mixture was allowed to cool to ambient temperature, toluene (100 ml) was added, then the mixture was washed with water (3×100 ml). The combined aqueous washings were shaken with toluene (50 ml), then the combined toluene solutions were dried (MgSO$_4$) and the solvent was removed in vacuo. The residual oil was distilled under reduced pressure to give 2-cyano-3-phenyl-but-2-enoic acid ethyl ester as an oil which was used without further purification.

Examples 2 to 18

The compounds set out below were prepared in the same way as in Example 1, using the appropriate starting materials.

| Example | Compound |
|---|---|
| 2 | 2-Cyano-3-(5-methyl-pyridin-2-yl)-but-2-enoic acid ethyl ester |
| 3 | 2-Cyano-3-(4-fluoro-phenyl)-but-2-enoic acid ethyl ester |
| 4 | 2-Cyano-3-thiophen-2-yl-but-2-enoic acid ethyl ester |
| 5 | 2-Cyano-3-methyl-but-2-enoic acid ethyl ester |
| 6 | 2-Cyano-3-p-tolyl-but-2-enoic acid ethyl ester |
| 7 | 3-(4-Chloro-phenyl)-2-cyano-but-2-enoic acid ethyl ester |
| 8 | 2-Cyano-3-(4-methoxy-phenyl)-but-2-enoic acid ethyl ester |
| 9 | 2-Cyano-3-phenyl-hex-2-enoic acid ethyl ester |
| 10 | 2-Cyano-3-o-tolyl-but-2-enoic acid ethyl ester |
| 11 | 2-Cyano-3-(3,4-dimethyl-phenyl)-but-2-enoic acid ethyl ester |
| 12 | 3-(4-Bromo-phenyl)-2-cyano-but-2-enoic acid ethyl ester |
| 13 | 2-Cyano-cyclohexyl-but-2-enoic acid ethyl ester |
| 14 | 3-(4-tert-Butyl-phenyl)-2-cyano-but-2-enoic acid ethyl ester |
| 15 | 2-Cyano-3-phenyl-pent-2-enoic acid ethyl ester |
| 16 | 3-Benzo[1,3]dioxol-5-yl-2-cyano-but-2-enoic acid ethyl ester |
| 17 | 3-Benzo[1,3]dioxol-5-yl-2-cyano-pent-2-enoic acid ethyl ester |
| 18 | 2-Cyano-3-(4-fluoro-phenyl)-pent-2-enoic acid ethyl ester |

Example 19

2-Amino-4-phenyl-thiophene-3-carboxylic acid ethyl ester

2-Cyano-3-phenyl-but-2-enoic acid ethyl ester (513.25 g, 2.3 mol) was added at ambient temperature to a vigorously-stirred suspension of powdered sulfur (76 g, 2.3 mols) in ethanol (500 ml). Diethylamine (200 ml) was added in portions over 20 minutes, during which time the temperature of the reaction rose to 62° C. The mixture was allowed to cool to 36° C., then it was heated to 50° C. and stirring at that temperature was continued for 1 hour. After this time, stirring was discontinued, the hot solution was removed by decantation from unreacted sulfur, then it was allowed to cool to ambient temperature. The resulting solid was collected by filtration, washed With a little cold ethanol and dried in vacuo to give 2-amino-4-phenylthiophene-3-carboxylic acid ethyl ester as an orange solid which was used without further purification.

Examples 20 to 36

The compounds set out below were prepared in the same way as in Example 19, using the appropriate starting materials.

| Example | Compound |
|---|---|
| 20 | 2-Amino-4-(5-methyl-pyridin-2-yl)-thiophene-3-carboxylic acid ethyl ester |
| 21 | 2-Amino-4-(4-fluoro-phenyl)-thiophene-3-carboxylic acid ethyl ester |
| 22 | 5'-Amino-[2,3']bithiophenyl-4'-carboxylic acid ethyl ester |
| 23 | 2-Amino-4-methyl-thiophene-3-carboxylic acid ethyl ester |
| 24 | 2-Amino-4-p-tolyl-thiophene-3-carboxylic acid ethyl ester |
| 25 | 2-Amino-4-(4-chloro-phenyl)-thiophene-3-carboxylic acid ethyl ester |
| 26 | 2-Amino-4-(4-bromo-phenyl)-thiophene-3-carboxylic acid ethyl ester |
| 27 | 2-Amino-4-(4-methoxy-phenyl)-thiophene-3-carboxylic acid ethyl ester |
| 28 | 2-Amino-4-(3,4-dimethyl-phenyl)-thiophene-3-carboxylic acid ethyl ester |
| 29 | 2-Amino-4-o-tolyl-thiophene-3-carboxylic acid ethyl ester |
| 30 | 2-Amino-5-ethyl-4-phenyl-thiophene-3-carboxylic acid ethyl ester |
| 31 | 2-Amino-4-(4-tert-butyl-phenyl)-thiophene-3-carboxylic acid ethyl ester |
| 32 | 2-Amino-4-cyclohexyl-thiophene-3-carboxylic acid ethyl ester |
| 33 | 2-Amino-5-methyl-4-phenyl-thiophene-3-carboxylic acid ethyl ester |
| 34 | 2-Amino-4-benzo[1,3]dioxol-5-yl-thiophene-3-carboxylic acid ethyl ester |
| 35 | 2-Amino-4-benzo[1,3]dioxol-5-yl-5-methyl-thiophene-3-carboxylic acid ethyl ester |
| 36 | 2-Amino-4-(4-fluoro-phenyl)-5-methyl-thiophene-3-carboxylic acid ethyl ester |

Example 37

5-Phenyl-3H-thieno[2,3-d]pyrimidin-4-one

A stirred mixture of 2-amino-4-phenylthiophene-3-carboxylic acid ethyl ester (350.43 g, 1.535 mol), formamidine acetate (799.13 g, 7.7 mol) and ethanol (1500 ml) was heated under reflux for 18 hours then allowed to cool to ambient temperature. The resulting solid was collected by filtration, washed with a little cold ethanol, then crystallised from ethanol to give 5-Phenyl-3H-thieno[2,3-d]pyrimidin-4-one as a yellow solid which was used without further purification.

Examples 38 to 54

The compounds set out below were prepared in the same way as in Example 37, using the appropriate starting materials.

| Example | Compound |
|---|---|
| 38 | 5-(5-Methyl-pyridin-2-yl)-3H-thieno[2,3-d]pyrimidin-4-one; |
| 39 | 5-(4-Fluoro-phenyl)-3H-thieno[2,3-d]pyrimidin-4-one; |
| 40 | 5-Thiophen-2-yl-3H-thieno[2,3-d]pyrimidin-4-one; |
| 41 | 5-Methyl-3H-thieno[2,3-d]pyrimidin-4-one; |
| 42 | 5-p-Tolyl-3H-thieno[2,3-d]pyrimidin-4-one; |
| 43 | 5-(4-Chloro-phenyl)-3H-thieno[2,3-d]pyrimidin-4-one; |
| 44 | 5-(4-Bromo-phenyl)-3H-thieno[2,3-d]pyrimidin-4-one; |
| 45 | 5-(4-Methoxy-phenyl)-3H-thieno[2,3-d]pyrimidin-4-one; |
| 46 | 5-(3,4-Dimethyl-phenyl)-3H-thieno[2,3-d]pyrimidin-4-one; |
| 47 | 5-(4-tert-Butyl-phenyl)-3H-thieno[2,3-d]pyrimidin-4-one; |
| 48 | 6-Ethyl-5-phenyl-3H-thieno[2,3-d]pyrimidin-4-one; |
| 49 | 5-Cyclohexyl-3H-thieno[2,3-d]pyrimidin-4-one; |
| 50 | 5-o-Tolyl-3H-thieno[2,3-d]pyrimidin-4-one; |
| 51 | 6-Methyl-5-phenyl-3H-thieno[2,3-d]pyrimidin-4-one |
| 52 | 5-Benzo[1,3]dioxol-5-yl-3H-thieno[2,3-d]pyrimidin-4-one |
| 53 | 5-Benzo[1,3]dioxol-5-yl-6-methyl-3H-thieno[2,3-d]pyrimidin-4-one |
| 54 | 5-(4-Fluoro-phenyl)-6-methyl-3H-thieno[2,3-d]pyrimidin-4-one |

Example 55

2-Methyl-5-phenyl-3H-thieno[2,3-d]pyrimidin-4-one

A stirred mixture of 2-amino-4-phenylthiophene-3-carboxylic acid ethyl ester (350.43 g, 1.54 mol), acetamidine hydrochloride (725.13 g, 7.676 mol) and ethanol (1500 ml) was heated under reflux for 18 hours then allowed to cool to ambient temperature. The resulting solid was collected by filtration, washed with a little cold ethanol, then crystallised from ethanol to give 2-Methyl-5-phenyl-3H-thieno[2,3-d]pyrimidin-4-one as a yellow solid which was used without further purification.

Example 56

The compound set out below was prepared in the same way as in Example 55, using the appropriate starting materials.

| Example | Compound |
|---|---|
| 56 | 5-(4-Fluoro-phenyl)-2-methyl-3H-thieno[2,3-d]pyrimidin-4-one |

Example 57

4-phenyl-2-propionylaminothiophene-3-carboxylic amide

A mixture of 2-amino-4-phenylthiophene-3-carboxylic acid amide (3.0 g, 13.8 mmol) and anhydrous pyridine (12 ml) was treated with propionyl chloride (1.32 ml, 15.2 mmol) and stirred at ambient temperature for 3 hours. The excess pyridine was removed in vacuo to give a residue, which was treated with ethanol (50 ml) and sodium methoxide (2.24 g, 41.4 mmol) and the resultant mixture was heated under reflux for 18 hours. The cooled mixture was then diluted with water (300 ml) and acidified with concentrated hydrochloric acid. The resulting solid was collected by filtration, washed with water and dried in vacuo to give 4-phenyl-2-propionylaminothiophene-3-carboxylic amide.

Example 58

2-ethyl-5-phenyl-3H-thieno[2,3-d]pyrimidin-4-one

The solid 4-phenyl-2-propionylaminothiophene-3-carboxylic amide was added to a mixture of ethanol (50 ml) and sodium methoxide (2.24 g) and the resultant mixture was heated under reflux with stirring for 18 hours. The cooled mixture was diluted with water (300 ml) and acidified with concentrated hydrochloric acid. The resulting solid was collected by filtration, washed with water followed by acetonitrile and dried in vacuo to give 2-ethyl-5-phenyl-3H-thieno[2,3-d]pyrimidin-4-one (2.38 g), which was used without further purification.

Example 59

5-Phenyl-2-trifluoromethyl-3H-thieno[2,3-d]pyrimidin-4-one

A stirred mixture of 2-amino-4-phenylthiophene-3-carboxylic acid ethyl ester (350.43 g, 1.535 mol), trifluoromethylacetamidine hydrochloride (1167.36 g, 7.676 mol) and ethanol (1500 ml) was heated under reflux for 18 hours then allowed to cool to ambient temperature. The resulting solid was collected by filtration, washed with a little cold ethanol, then crystallised from ethanol to give 5-Phenyl-2-trifluoromethyl-3H-thieno[2,3-d]pyrimidin-4-one as a yellow solid which was used without further purification.

Example 60

2-Isopropyl-5-phenyl-3H-thieno[2,3-d]pyrimidin-4-one

A stirred mixture of 2-amino-4-phenylthiophene-3-carboxylic acid ethyl ester (350.43 g, 1.54 mol), isopropylacetamidine hydrochloride (958.75 g, 7.7 mol) and ethanol (1500 ml) was heated under reflux for 18 hours then allowed to cool to ambient temperature. The resulting solid was collected by filtration, washed with a little cold ethanol, then crystallised from ethanol to give 2-Isopropyl-5-phenyl-3H-thieno[2,3-d]pyrimidin-4-one as a yellow solid which was used without further purification.

Example 61

4-Chloro-5-phenyl-thieno[2,3-d]pyrimidine

5-Phenyl-3H-thieno[2,3-d]pyrimidin-4-one (294.6 g, 1.29 mol) was added in portions to stirred phosphoryl chloride (1000 ml), then the stirred suspension was warmed gently to reflux temperature, heated under reflux for 4 hours, and allowed to stand at ambient temperature for 18 hours. The resulting dark solution was removed by decantation from a solid residue and concentrated in vacuo to give a gummy solid. The two solids were combined and added to crushed ice (1000 ml). The product was extracted into dichloromethane (3×500 ml), then the combined extracts were washed with water (2×300 ml) and saturated aqueous sodium hydrogen carbonate solution (500 ml) and dried and decolourised (MgSO$_4$+charcoal). The solvent was removed in vacuo to give 4-Chloro-5-phenyl-thieno[2,3-d]pyrimidine as a yellow/orange solid which was used without further purification.

Examples 62 to 82

The compounds set out below were prepared in the same way as in Example 61, using the appropriate starting materials.

| Example | Compound |
|---|---|
| 62 | 4-Chloro-5-(5-methyl-pyridin-2-yl)-thieno[2,3-d]pyrimidine |
| 63 | 4-Chloro-5-(4-fluoro-phenyl)-thieno[2,3-d]pyrimidine |
| 64 | 4-Chloro-5-thiophen-2-yl-thieno[2,3-d]pyrimidine |
| 65 | 4-Chloro-5-methyl-thieno[2,3-d]pyrimidine |
| 66 | 4-Chloro-5-p-tolyl-thieno[2,3-d]pyrimidine |
| 67 | 4-Chloro-5-(3,4-dimethyl-phenyl)-thieno[2,3-d]pyrimidine |
| 68 | 4-Chloro-5-(4-chloro-phenyl)-thieno[2,3-d]pyrimidine |
| 69 | 5-(4-Bromo-phenyl)-4-chloro-thieno[2,3-d]pyrimidine |
| 70 | 4-Chloro-5-(4-methoxy-phenyl)-thieno[2,3-d]pyrimidine |
| 71 | 4-Chloro-6-ethyl-5-phenyl-thieno[2,3-d]pyrimidine |
| 72 | 4-Chloro-5-o-tolyl-thieno[2,3-d]pyrimidine |
| 73 | 5-(4-tert-Butyl-phenyl)-4-chloro-thieno[2,3-d]pyrimidine |
| 74 | 4-Chloro-5-cyclohexyl-thieno[2,3-d]pyrimidine |
| 75 | 4-Chloro-2-methyl-5-phenyl-thieno[2,3-d]pyrimidine |
| 76 | 4-Chloro-5-phenyl-2-trifluoromethyl-thieno[2,3-d]pyrimidine |
| 77 | 4-Chloro-2-isopropyl-5-phenyl-thieno[2,3-d]pyrimidine |
| 78 | 4-Chloro-2-ethyl-5-phenyl-thieno[2,3-d]pyrimidine |
| 79 | 4-Chloro-6-methyl-5-phenyl-thieno[2,3-d]pyrimidine |
| 80 | 4-Chloro-5-(4-fluoro-phenyl)-2-methyl-thieno[2,3-d]pyrimidine |
| 81 | 5-(1,3-Benzodioxol-5-yl)-4-chloro-6-methylthieno[2,3-d]pyrimidine |
| 82 | 4-Chloro-5-(4-fluorophenyl)-6-methylthieno[2,3-d]pyrimidine |

Example 83

Furan-2-ylmethyl-(5-phenyl-thieno[2,3-d]pyrimidin-4-yl)-amine

A stirred mixture of 4-chloro-5-phenylthieno[2,3-d]pyrimidine (2.2 g, 0.009 mol), furfurylamine (1.26 g, 0.013 mol), triethylamine (1.3 g) and ethanol (20 ml) was heated under reflux for 2 hours then cooled to ambient temperature and poured into water (50 ml). The resulting solid was collected by filtration, washed with water (30 ml), dried in vacuo and crystallised from a mixture of hexane and toluene to give furan-2-ylmethyl-(5-phenyl-thieno[2,3-d]pyrimidin-4-yl)-amine as a pale yellow solid, m.pt. 77-79° C.

Examples 84 to 100

The compounds set out below were prepared in the same way as in Example 83, using the appropriate starting materials.

| Example | Compound |
|---|---|
| 84 | Cyclopropylmethyl-(5-phenyl-thieno[2,3-d]pyrimidin-4-yl)-amine |
| 85 | (5-Phenyl-thieno[2,3-d]pyrimidin-4-yl)-thiophen-2-ylmethyl-amine |
| 86 | Benzyl-(5-phenyl-thieno[2,3-d]pyrimidin-4-yl)-amine |
| 87 | Allyl-(5-phenyl-thieno[2,3-d]pyrimidin-4-yl)-amine |
| 88 | Furan-2-ylmethyl-methyl-(5-phenyl-thieno[2,3-d]pyrimidin-4-yl)-amine |
| 89 | Cyclohexylmethyl-(5-phenyl-thieno[2,3-d]pyrimidin-4-yl)-amine |
| 90 | Phenethyl-(5-phenyl-thieno[2,3-d]pyrimidin-4-yl)-amine |
| 91 | Cyclohexyl-(5-phenyl-thieno[2,3-d]pyrimidin-4-yl)-amine |
| 92 | Furan-2-ylmethyl-(5-thiophen-2-yl-thieno[2,3-d]pyrimidin-4-yl)-amine |
| 93 | (4-Nitro-benzyl)-(5-thiophen-2-yl-thieno[2,3-d]pyrimidin-4-yl)-amine |
| 94 | (5-Thiophen-2-yl-thieno[2,3-d]pyrimidin-4-yl)-(3,4,5-trimethoxy-benzyl)-amine |
| 95 | Cyclopropylmethyl-(5-thiophen-2-yl-thieno[2,3-d]pyrimidin-4-yl)-amine |
| 96 | Isobutyl-(5-thiophen-2-yl-thieno[2,3-d]pyrimidin-4-yl)-amine |
| 97 | Benzyl-(5-thiophen-2-yl-thieno[2,3-d]pyrimidin-4-yl)-amine |
| 98 | Thiophen-2-ylmethyl-(5-thiophen-2-yl-thieno[2,3-d]pyrimidin-4-yl)-amine |
| 99 | Allyl-(5-thiophen-2-yl-thieno[2,3-d]pyrimidin-4-yl)-amine |
| 100 | Furan-2-ylmethyl-methyl-(5-thiophen-2-yl-thieno[2,3-d]pyrimidin-4-yl)-amine |

Example 101

2-Methyl-N-(2-pyridyl)methyl-5-phenylthieno[2,3-d]pyrimidin-4-ylamine

In a 10 ml glass tube were placed 2-methyl-4-chloro-5-phenylthieno[2,3-d]pyrimidin-4-ylamine (0.076 g, 0.293 mmol), 2-(aminomethyl)pyridine (0.0364 g, 0.03 mmol) and ethanol (2.5 ml). The vessel was sealed with a septum and placed in the microwave cavity. Microwave irradiation of 200 W was used, the temperature being ramped from room temperature to 150° C. Once 150° C. was reached, the reaction mixture was held at this temperature for 10 minutes. After cooling to ambient temperature, water (4 ml) was added and the mixture stirred for 2.5 hours. The resulting solid was collected by filtration, washed with water and dried in vacuo to give 2-methyl-N-(2-pyridyl)methyl-5-phenylthieno[2,3-d]pyrimidin-4-ylamine (0.084 g) as an off white solid, m.pt. 110-112° C.

Examples 102 to 167

The compounds set out below were prepared in the same way as in Example 101, using the appropriate starting materials.

| Example | Compound |
|---|---|
| 102 | (1-Ethyl-pyrrolidin-2-ylmethyl)-(5-phenyl-thieno[2,3-d]pyrimidin-4-yl)-amine |
| 103 | N,N-Dimethyl-2-(5-phenyl-thieno[2,3-d]pyrimidin-4-ylamino)-acetamide |
| 104 | (3-Imidazol-1-yl-propyl)-(5-phenyl-thieno[2,3-d]pyrimidin-4-yl)-amine |
| 105 | (5-Phenyl-thieno[2,3-d]pyrimidin-4-yl)-pyridin-2-ylmethyl-amine |
| 106 | 5-Phenyl-4-(pyridin-2-ylmethoxy)-thieno[2,3-d]pyrimidine |
| 107 | Furan-3-ylmethyl-(5-phenyl-thieno[2,3-d]pyrimidin-4-yl)-amine |
| 108 | (5-Methyl-furan-2-ylmethyl)-(5-phenyl-thieno[2,3-d]pyrimidin-4-yl)-amine |
| 109 | 4-(Furan-2-ylmethoxy)-5-phenyl-thieno[2,3-d]pyrimidine |
| 110 | (1-Methyl-1H-pyrrol-2-ylmethyl)-(5-phenyl-thieno[2,3-d]pyrimidin-4-yl)-amine |
| 111 | (5-Phenyl-thieno[2,3-d]pyrimidin-4-yl)-(2-pyridin-2-yl-ethyl)-amine |
| 112 | (5-Phenyl-thieno[2,3-d]pyrimidin-4-ylamino)-acetic acid methyl ester |
| 113 | (2-Methoxy-ethyl)-(5-phenyl-thieno[2,3-d]pyrimidin-4-yl)-amine |
| 114 | (5-Phenyl-thieno[2,3-d]pyrimidin-4-yl)-(tetrahydro-furan-2-ylmethyl)-amine |
| 115 | Thiophen-2-ylmethyl-(5-thiophen-2-yl-thieno[2,3-d]pyrimidin-4-yl)-amine |
| 116 | [1,3]Dioxolan-2-ylmethyl-(5-phenyl-thieno[2,3-d]pyrimidin-4-yl)-amine |
| 117 | 4-(Furan-2-ylmethylsulfanyl)-5-phenyl-thieno[2,3-d]pyrimidine |
| 118 | (5-Phenyl-thieno[2,3-d]pyrimidin-4-yl)-(2-thiophen-2-yl-ethyl)-amine |
| 119 | 4-Benzyloxy-5-phenyl-thieno[2,3-d]pyrimidine |
| 120 | 5-Phenyl-4-(pyridin-2-ylmethylsulfanyl)-thieno[2,3-d]pyrimidine |
| 121 | [5-(5-Methyl-pyridin-2-yl)-thieno[2,3-d]pyrimidin-4-yl]-pyridin-2-ylmethyl-amine |
| 122 | Furan-2-ylmethyl-[5-(5-methyl-pyridin-2-yl)-thieno[2,3-d]pyrimidin-4-yl]-amine |

| Example | Compound |
|---|---|
| 123 | [5-(4-Fluoro-phenyl)-thieno[2,3-d]pyrimidin-4-yl]-pyridin-2-ylmethyl-amine |
| 124 | [5-(4-Fluoro-phenyl)-thieno[2,3-d]pyrimidin-4-yl]-furan-2-ylmethyl-amine |
| 125 | [2-(4-Chloro-phenyl)-ethyl]-(5-methyl-thieno[2,3-d]pyrimidin-4-yl)-amine |
| 126 | Furan-2-ylmethyl-(5-p-tolyl-thieno[2,3-d]pyrimidin-4-yl)-amine |
| 127 | [2-(3,4-Dimethoxy-phenyl)-ethyl]-(5-p-tolyl-thieno[2,3-d]pyrimidin-4-yl)-amine |
| 128 | 1-[2-(5-p-Tolyl-thieno[2,3-d]pyrimidin-4-ylamino)-ethyl]-imidazolidin-2-one |
| 129 | 4-(Naphthalen-2-yloxy)-5-p-tolyl-thieno[2,3-d]pyrimidine |
| 130 | Phenethyl-(5-p-tolyl-thieno[2,3-d]pyrimidin-4-yl)-amine |
| 131 | 4-(5-p-Tolyl-thieno[2,3-d]pyrimidin-4-yloxy)-benzoic acid methyl ester |
| 132 | [2-(2,3-Dihydro-benzo[1,4]dioxin-6-yl)-ethyl]-[5-(3,4-dimethyl-phenyl)-thieno[2,3-d]pyrimidin-4-yl]-amine |
| 133 | [5-(3,4-Dimethyl-phenyl)-thieno[2,3-d]pyrimidin-4-yl]-furan-2-ylmethyl-amine |
| 134 | 4-(4-tert-Butyl-phenoxy)-5-(4-chloro-phenyl)-thieno[2,3-d]pyrimidine |
| 135 | [5-(4-Chloro-phenyl)-thieno[2,3-d]pyrimidin-4-yl]-furan-2-ylmethyl-amine |
| 136 | [5-(4-Chloro-phenyl)-thieno[2,3-d]pyrimidin-4-yl]-phenethyl-amine |
| 137 | [5-(4-Bromo-phenyl)-thieno[2,3-d]pyrimidin-4-yl]-[2-(2,3-dihydro-benzo[1,4]dioxin-6-yl)-ethyl]-amine |
| 138 | [5-(4-Methoxy-phenyl)-thieno[2,3-d]pyrimidin-4-yl]-pyridin-2-ylmethyl-amine |
| 139 | Furan-2-ylmethyl-[5-(4-methoxy-phenyl)-thieno[2,3-d]pyrimidin-4-yl]-amine |
| 140 | (6-Ethyl-5-phenyl-thieno[2,3-d]pyrimidin-4-yl)-furan-2-ylmethyl-amine |
| 141 | (6-Ethyl-5-furan-3-yl-thieno[2,3-d]pyrimidin-4-yl)-furan-2-ylmethyl-amine |
| 142 | Pyridin-2-ylmethyl-(5-o-tolyl-thieno[2,3-d]pyrimidin-4-yl)-amine |
| 143 | Furan-2-ylmethyl-(5-o-tolyl-thieno[2,3-d]pyrimidin-4-yl)-amine |
| 144 | [5-(4-tert-Butyl-phenyl)-thieno[2,3-d]pyrimidin-4-yl]-pyridin-2-ylmethyl-amine |
| 145 | [5-(4-tert-Butyl-phenyl)-thieno[2,3-d]pyrimidin-4-yl]-furan-2-ylmethyl-amine |
| 146 | (5-Cyclohexyl-thieno[2,3-d]pyrimidin-4-yl)-pyridin-2-ylmethyl-amine |
| 147 | (5-Cyclohexyl-thieno[2,3-d]pyrimidin-4-yl)-furan-2-ylmethyl-amine |
| 148 | (2-Isopropyl-5-phenyl-thieno[2,3-d]pyrimidin-4-yl)-pyridin-2-ylmethyl-amine |
| 149 | (5-Phenyl-thieno[2,3-d]pyrimidin-4-yl)-(1-pyridin-2-yl-ethyl)-amine |
| 150 | Furan-2-ylmethyl-(2-methyl-5-phenyl-thieno[2,3-d]pyrimidin-4-yl)-amine |
| 151 | (5-Phenyl-2-trifluoromethyl-thieno[2,3-d]pyrimidin-4-yl)-pyridin-2-ylmethyl-amine |
| 152 | (2-Ethyl-5-phenyl-thieno[2,3-d]pyrimidin-4-yl)-pyridin-2-ylmethyl-amine |
| 153 | (2-Ethyl-5-phenyl-thieno[2,3-d]pyrimidin-4-yl)-furan-2-ylmethyl-amine |
| 154 | (6-Methylpyridin-2-ylmethyl)-(5-phenyl-thieno[2,3-d]pyrimidin-4-yl)-amine |
| 155 | [5-(4-Fluorophenyl)-2-methyl-thieno[2,3-d]pyrimidin-4-yl]-pyridin-2-ylmethyl-amine |
| 156 | (3-methyl-pyridin-2-ylmethyl)-(5-phenyl-thieno[2,3-d]pyrimidin-4-yl)-amine |
| 157 | (6-Methyl-5-phenyl-thieno[2,3-d]pyrimidin-4-yl)-pyridin-2-ylmethyl-amine |
| 158 | (5-Phenyl-thieno[2,3-d]pyrimidin-4-yl)-(1,2,3,4-tetrahydro-naphthalen-l-yl)-amine |
| 159 | 6-Methyl-5-phenyl-4-piperidin-l-yl-thieno[2,3-d]pyrimidine |
| 160 | 2-[(5-Phenyl-thieno[2,3-d]pyrimidin-4-ylamino)-methyl]-nicotinic acid ethyl ester |
| 161 | (5-Phenyl-thieno[2,3-d]pyrimidin-4-yl)-(2-thiophen-2-yl-thiazol-4-ylmethyl)-amine |
| 162 | (2-Phenyl-thiazol-4-ylmethyl)-(5-phenyl-thieno[2,3-d]pyrimidin-4-yl)-amine |
| 163 | Phenethyl-(5-thiophen-2-yl-thieno[2,3-d]pyrimidin-4-yl)-amine |
| 164 | (6-Bromo-5-phenyl-thieno[2,3-d]pyrimidin-4-yl)-pyridin-2-ylmethyl-amine |
| 165 | (6-Bromo-5-phenyl-thieno[2,3-d]pyrimidin-4-yl)-furan-2-ylmethyl-amine |
| 166 | 6-methyl-N-[(6-methylpyridin-2-yl)methyl]-5-phenylthieno[2,3-d]pyrimidin-4-amine |
| 167 | 6-bromo-N-[(6-methylpyridin-2-yl)methyl]-5-phenylthieno[2,3-d]pyrimidin-4-amine |

Example 168

5-Phenyl-1,3H-thieno[2,3-d]pyrimidine-2,4-dione

A mixture of ethyl 2-amino-4-phenyl-thiophene-3-carboxylate (2.0 g, 8.1 mmol) and potassium cyanate (2.0 g, 24.3 mmol) in glacial acetic acid (20 ml) was stirred at ambient temperature for 72 hours. The resultant solid material was filtered off. The filtrate was diluted with water (50 ml) and the precipitated solid was filtered off. The two solids were combined, suspended in water (100 ml) and made alkaline by the addition of concentrated sodium hydroxide solution. The resultant suspension was heated at 100° C. for 2 hours with stirring, then allowed to cool to ambient temperature and acidified by the addition of glacial acetic acid. The resulting solid was collected by filtration to give 5-phenyl-1,3H-thieno[2,3-d]pyrimidin-2,4-dione (1.1 g) as a white solid which was used without further purification.

Examples 169 to 174

The compounds set out below were prepared in the same way as in Example 168, using the appropriate starting materials.

| Example | Compound |
|---|---|
| 169 | 5-(4-Fluorophenyl)-1,3H-thieno[2,3-d]pyrimidine-2,4-dione |
| 170 | 6-Methyl-1,3H-thieno[2,3-d]pyrimidine-2,4-dione |
| 171 | 5-Benzo[1,3]dioxol-5-yl-1,3H-thieno[2,3-d]pyrimidine-2,4-dione |
| 172 | 5-(1,3-Benzodioxol-5-yl)-6-methyl-1,3H-thieno[2,3-d]pyrimidine-2,4-dione |
| 173 | 5-(4-Fluorophenyl)-6-methyl-1,3H-thieno[2,3-d]pyrimidine-2,4-dione |
| 174 | 6-Methyl-5-phenyl-1,3H-thieno[2,3-d]pyrimidine-2,4-dione |

Example 175

2,4-Dichloro-5-phenyl-thieno[2,3-d]pyrimidine

A stirred mixture of 5-phenyl-1,3H-thieno[2,3-d]pyrimidin-2,4-dione (1.07 g, 4.39 mmol) and phenylphosphonic dichloride (10 ml) was heated at 150° C. for 7 hours then allowed to stand at ambient temperature for 18 hours. The resulting dark solution was poured into ice-water and extracted with dichloromethane (3×150 ml). The combined extracts were washed with saturated sodium hydrogen carbonate solution (150 ml) and dried (MgSO$_4$). The solvent was removed in vacuo and the oily residue triturated with 40-60° C. petrol to give 2,4-dichloro-5-phenyl-thieno[2,3-d]pyrimidine (0.82 g) as a pale yellow solid which was used without further purification.

Examples 176 to 180

The compounds set out below were prepared in the same way as in Example 175, using the appropriate starting materials.

| Example | Compound |
|---------|----------|
| 176 | 2,4-Dichloro-5-(4-fluoro-phenyl)-thieno[2,3-d]pyrimidine |
| 177 | 5-Benzo[1,3]dioxol-5-yl-2,4-dichloro-thieno[2,3-d]pyrimidine |
| 178 | 2,4-Dichloro-6-methyl-5-phenylthieno[2,3-d]pyrimidine |
| 179 | 2,4-Dichloro-5-(4-fluorophenyl)-6-methylthieno[2,3-d]pyrimidine |
| 180 | 5-(1,3-Benzodioxol-5-yl)-2,4-dichloro-6-methylthieno[2,3-d]pyrimidine |

Example 181

(2-Chloro-5-phenyl-thieno[2,3]pyrimidin-4-yl)-pyridin-2-ylmethyl-amine

A mixture of 2,4-dichloro-5-phenyl-thieno[2,3-d]pyrimidine (0.82 g, 2.92 mmol), 2-(aminomethyl)pyridine (0.35 g, 3.21 mmol), triethylamine (0.32 g, 0.45 ml, 3.21 mmol) and propan-2-ol (20 ml) was stirred at ambient temperature for 72 hours. Water (50 ml) was added to the reaction mixture and the organic phase was extracted using dichloromethane (3×50 ml). The combined extracts were washed with water and dried (MgSO$_4$). The solvent was removed in vacuo to give 2-chloro-N-(2-pyridyl)methyl-5-phenylthieno[2,3-d]pyrimidin-4-ylamine (1.0 g) as a white solid which was used without further purification.

Examples 182 to 187

The compounds set out below were prepared in the same way as in Example 181, using the appropriate starting materials.

| Example | Compound |
|---------|----------|
| 182 | (2-Chloro-5-phenyl-thieno[2,3-d]pyrimidin-4-yl)-furan-2-ylmethyl-amine; |
| 183 | [2-Chloro-5-(4-fluorophenyl)-thieno[2,3-d]pyrimidin-4-yl]-pyridin-2-ylmethyl-amine |
| 184 | (2-Chloro-5-phenyl-thieno[2,3-d]pyrimidin-4-yl)-(6-methyl-pyridin-2-ylmethyl)-amine |
| 185 | [2-Chloro-5-(4-fluorophenyl)-thieno[2,3-d]pyrimidin-4-yl]-(6-methyl-pyridin-2-ylmethyl)-amine |
| 186 | (5-Benzo[1,3]dioxol-5-yl-2-chloro-thieno[2,3-d]pyrimidin-4-yl)-(6-methyl-pyridin-2-ylmethyl)-amine |
| 187 | (5-Benzo[1,3]dioxol-5-yl-2-chloro-thieno[2,3-d]pyrimidin-4-yl)-pyridin-2-ylmethyl-amine |

Example 188

$N^2$-Cyclopropylmethyl-5-phenyl-$N^4$-pyridin-2-ylmethyl-thieno[2,3-d]pyrimidine-2,4-diamine In a 10 ml glass tube were placed 2-chloro-N-(2-pyridyl)methyl-5-phenylthieno[2,3-d]pyrimidin-4-ylamine (0.03 g, 0.0852 mmol) and cyclopropylmethylamine (0.5 ml). The vessel was sealed with a septum and placed in the microwave cavity. Microwave irradiation of 200 W was used, the temperature being ramped from room temperature to 200° C. Once 200° C. was reached, the reaction mixture was held at this temperature for 40 minutes. After cooling to ambient temperature, water (4 ml) was added and the mixture stirred for 2.5 hours. The resulting solid was collected by filtration, washed with water and dried under reduced pressure to give $N^2$-Cyclopropylmethyl-5-phenyl-$N^4$-pyridin-2-ylmethyl-thieno[2,3-d]pyrimidine-2,4-diamine (0.025 g) as a yellow solid, m.p.t. 109-111° C.

Examples 189 to 224

The compounds set out below were prepared in the same way as in Example 188, using the appropriate starting materials.

| Example | Compound |
|---------|----------|
| 189 | $N^2$-(2-Methoxyethyl)-5-phenyl-$N^4$-(pyridin-2-ylmethyl)thieno[2,3-d]pyrimidine-2,4-diamine |
| 190 | 2-{5-Phenyl-4-[(pyridin-2-ylmethyl)-amino]-thieno[2,3-d]pyrimidin-2-ylamino}-ethanol |
| 191 | (2-Methoxy-5-phenyl-thieno[2,3-d]pyrimidin-4-yl)-pyridin-2-ylmethyl-amine |
| 192 | 5-Phenyl-N-4-pyridin-2-ylmethyl-thieno[2,3-d]pyrimidine-2,4-diamine |
| 193 | N,N'-Bis(2-furylmethyl)-5-phenylthieno[2,3-d]pyrimidine-2,4-diamine |
| 194 | 5-(3,4-Dimethylphenyl)-N-(2-furylmethyl)thieno[2,3-d]pyrimidin-4-amine |
| 195 | (2-Benzyloxy-5-phenyl-thieno[2,3-d]pyrimidin-4-yl)-furan-2-ylmethyl-amine |
| 196 | $N^2$-methyl-5-phenyl-$N^4$-(pyridin-2-ylmethyl)thieno[2,3-d]pyrimidine-2,4-diamine |
| 197 | (2-Morpholin-4-yl-5-phenyl-thieno[2,3-d]pyrimidin-4-yl)-pyridin-2-ylmethyl-amine |
| 198 | $N^2,N^2$-Dimethyl-5-phenyl-$N^4$-pyridin-2-ylmethyl-thieno[2,3-d]pyrimidine-2,4-diamine |
| 199 | 5-Phenyl-4-[(pyridin-2-ylmethyl)-amino]-thieno[2,3-d]pyrimidine-2-carbonitrile |
| 200 | 5-(4-Fluorophenyl)-$N^2,N^2$-dimethyl-$N^4$-pyridin-2-ylmethyl-thieno[2,3-d]pyrimidine-2,4-diamine |
| 201 | 1-{5-(4-Fluorophenyl)-4-[(pyridin-2-ylmethyl)-amino]-thieno[2,3-d]pyrimidin-2-yl}-piperidine-4-carboxylic acid methyl ester |
| 202 | 3-{5-Phenyl-4-[(pyridin-2-ylmethyl)-amino]-thieno[2,3-d]pyrimidin-2-ylamino}-propionic acid ethyl ester |
| 203 | [2-(2-Methoxy-ethoxy)-5-phenyl-thieno[2,3-d]pyrimidin-4-yl]-pyridin-2-ylmethyl-amine |
| 204 | 5-(4-Fluorophenyl)-$N^2$-methyl-$N^4$-pyridin-2-ylmethyl-thieno[2,3-d]pyrimidine-2,4-diamine |
| 205 | 5-(4-Fluorophenyl)-$N^4$-pyridin-2-ylmethyl-thieno[2,3-d]pyrimidine-2,4-diamine |
| 206 | 2-(1-{5-Phenyl-4-[(pyridin-2-ylmethyl)-amino]-thieno[2,3-d]pyrimidin-2-yl}-piperidin-4-yl)-ethanol |
| 207 | [5-(4-Fluorophenyl)-2-morpholin-4-yl-thieno[2,3-d]pyrimidin-4-yl]-pyridin-2-ylmethyl-amine |
| 208 | 2-((2-Hydroxy-ethyl)-{5-phenyl-4-[(pyridin-2-ylmethyl)-amino]-thieno[2,3-d]pyrimidin-2-yl}-amino)-ethanol |
| 209 | 5-(4-Fluorophenyl)-$N^2$-(2-methoxy-ethyl)-$N^4$-pyridin-2-ylmethyl-thieno[2,3-d]pyrimidine-2,4-diamine |
| 210 | 2-{5-Phenyl-4-[(pyridin-2-ylmethyl)-amino]-thieno[2,3-d]pyrimidin-2-ylamino}-propane-1,3-diol |
| 211 | [2-(2-Dimethylamino-ethoxy)-5-phenyl-thieno[2,3-d]pyrimidin-4-yl]-pyridin-2-ylmethyl-amine |
| 212 | 2-{5-(4-Fluorophenyl)-4-[(pyridin-2-ylmethyl)-amino]-thieno[2,3-d]pyrimidin-2-ylamino}-ethanol |
| 213 | 2-{4-[(6-Methyl-pyridin-2-ylmethyl)-amino]-5-phenyl-thieno[2,3-d]pyrimidin-2-ylamino}-ethanol |
| 214 | 3-{5-Phenyl-4-[(pyridin-2-ylmethyl)-amino]-thieno[2,3-d]pyrimidin-2-ylamino)}-propane-1,2-diol |
| 215 | [2-(4-Methyl-piperazin-1-yl)-5-phenyl-thieno[2,3-d]pyrimidin-4-yl]-pyridin-2-ylmethyl-amine |
| 216 | 2-{4-[(6-Methyl-pyridin-2-ylmethyl)-amino]-5-phenyl-thieno[2,3-d]pyrimidin-2-ylamino}-ethanol |
| 217 | 2-((2-Hydroxy-ethyl)-{4-[(6-methyl-pyridin-2-ylmethyl)-amino]-5-phenyl-thieno[2,3-d]pyrimidin-2-yl}-amino)-ethanol |

| Example | Compound |
|---|---|
| 218 | 2-{5-(4-Fluorophenyl)-4-[(6-methyl-pyridin-2-ylmethyl)-amino]-thieno[2,3-d]pyrimidin-2-ylamino}-ethanol |
| 219 | 2-[{5-(4-Fluorophenyl)-4-[(pyridin-2-ylmethyl)-amino]-thieno[2,3-d]pyrimidin-2-yl}-(2-hydroxy-ethyl)-amino]-ethanol |
| 220 | 2-[{5-(4-Fluorophenyl)-4-[(6-methyl-pyridin-2-ylmethyl)-amino]-thieno[2,3-d]pyrimidin-2-yl}-(2-hydroxy-ethyl)-amino]-ethanol |
| 221 | 2-{5-Benzo[1,3]dioxol-5-yl-4-[(pyridin-2-ylmethyl)-amino]-thieno[2,3-d]pyrimidin-2-ylamino}-ethanol |
| 222 | 2-{5-Benzo[1,3]dioxol-5-yl-4-[(6-methyl-pyridin-2-ylmethyl)-amino]-thieno[2,3-d]pyrimidin-2-ylamino}-ethanol |
| 223 | 2-[{5-Benzo[1,3]dioxol-5-yl-4-[(pyridin-2-ylmethyl)-amino]-thieno[2,3-d]pyrimidin-2-yl}-(2-hydroxy-ethyl)-amino]-ethanol |
| 224 | 2-[{5-Benzo[1,3]dioxol-5-yl-4-[(6-methyl-pyridin-2-ylmethyl)-amino]-thieno[2,3-d]pyrimidin-2-yl}-(2-hydroxy-ethyl)-amino]-ethanol |

Example 225

(4-Oxo-5-phenyl-3,4-dihydrothieno[2,3-d]pyrimidin-2-yl)acetic acid ethyl ester

Hydrogen chloride gas was bubbled through a stirred reaction mixture of 2-amino-4-phenylthiophene-3-carboxylic acid ethyl ester (4.94 g, 0.02 mol) in ethyl cyanoacetate (50 ml) for 2 hours. A thick suspension formed initially which slowly dissolved on gentle warming. The mixture was allowed to stand at ambient temperature for 18 hours. Excess hydrogen chloride was removed by bubbling nitrogen through the reaction mixture and most of the excess ethyl cyanoacetate was distilled out at reduced pressure. The solid residue was recrystallised from ethanol to give (4-oxo-5-phenyl-3,4-dihydrothieno[2,3-d]pyrimidin-2-yl)acetic acid ethyl ester (3.64 g), which was used without further purification.

Examples 226 to 230

The compounds set out below were prepared in the same way as in Example 225, using the appropriate starting materials.

| Example | Compound |
|---|---|
| 226 | [5-(4-Fluorophenyl)-4-oxo-3,4-dihydro-thieno[2,3-d]pyrimidin-2-yl]-acetic acid ethyl ester |
| 227 | (5-Benzo[1,3]dioxol-5-yl-4-oxo-3,4-dihydro-thieno[2,3-d]pyrimidin-2-yl)-acetic acid ethyl ester |
| 228 | (6-Methyl-4-oxo-5-phenyl-3,4-dihydro-thieno[2,3-d]pyrimidin-2-yl)-acetic acid ethyl ester |
| 229 | [5-(4-Fluorophenyl)-6-methyl-4-oxo-3,4-dihydro-thieno[2,3-d]pyrimidin-2-yl]-acetic acid ethyl ester |
| 230 | (5-Benzo[1,3]dioxol-5-yl-6-methyl-4-oxo-3,4-dihydro-thieno[2,3-d]pyrimidin-2-yl)-acetic acid ethyl ester |

Example 231

(4-Chloro-5-phenylthieno[2,3-d]pyrimidin-2-yl)acetic acid ethyl ester

A stirred solution of (4-oxo-5-phenyl-3,4-dihydrothieno[2,3-d]pyrimidin-2-yl)acetic acid ethyl ester (1.0 g, 3.185 mmol), phosphoryl chloride (15 ml) and N,N-dimethylaniline (4.8 ml) was heated under reflux for 6 hours and then left to stand at ambient temperature for 18 hours. The excess phosphoryl chloride was removed in vacuo to give a dark residue, which was dissolved in dichloromethane (100 ml) and then washed with water (2×50 ml) followed by saturated sodium hydrogen carbonate solution (50 ml). The organic layer was dried (MgSO$_4$) and the solvent was removed in vacuo to give the crude product. Purification by flash chromatography (silica) eluting with dichloromethane and 40°-60° petroleum ether (3:1) gave (4-chloro-5-phenylthieno[2,3-d]pyrimidin-2-yl)acetic acid ethyl ester as a pale-yellow solid (0.86 g).

Examples 232 to 236

The compounds set out below were prepared in the same way as in Example 231, using the appropriate starting materials.

| Example | Compound |
|---|---|
| 232 | [4-Chloro-5-(4-Fluorophenyl)-thieno[2,3-d]pyrimidin-2-yl]-acetic acid ethyl ester |
| 233 | (4-Chloro-5-Benzo[1,3]dioxol-5-yl-thieno[2,3-d]pyrimidin-2-yl)-acetic acid ethyl ester |
| 234 | (4-Chloro-6-methyl-5-phenyl-thieno[2,3-d]pyrimidin-2-yl)-acetic acid ethyl ester |
| 235 | [4-Chloro-5-(4-fluorophenyl)-6-methyl-thieno[2,3-d]pyrimidin-2-yl]-acetic acid ethyl ester |
| 236 | (5-Benzo[1,3]dioxol-5-yl-4-chloro-6-methyl-thieno[2,3-d]pyrimidin-2-yl)-acetic acid ethyl ester |

Example 237

{5-Phenyl-4-[(pyridin-2-ylmethyl)amino]thieno[2,3-d]pyrimidin-2-yl}acetic acid ethyl ester A stirred mixture of (4-chloro-5-phenylthieno[2,3-d]pyrimidin-2-yl)acetic acid ethyl ester (0.36 g, 1.08 mmol), 2-aminomethylpyridine (0.12 ml, 1.19 mmol), triethylamine (0.17 ml, 1.19 mmol) and ethanol (8 ml) was heated under reflux for 4 hours. The solution was then cooled to ambient temperature, poured into water (100 ml) and extracted with dichloromethane (3×50 ml). The combined organic extracts were dried (MgSO$_4$) and the solvent removed in vacuo to give the crude product. Purification by flash chromatography (silica) eluting with ethyl acetate and 40°-60° petroleum ether (1:2) gave {5-phenyl-4-[(pyridin-2-ylmethyl)amino]thieno[2,3-d]pyrimidin-2-yl}acetic acid ethyl ester as a colourless gum (0.41 g).

Examples 238 to 249

The compounds set out below were prepared in the same way as in Example 237, using the appropriate starting materials.

| Example | Compound |
|---|---|
| 238 | {4-[(Furan-2-ylmethyl)-amino]-5-phenyl-thieno[2,3-d]pyrimidin-2-yl}-acetic acid ethyl ester |
| 239 | {5-(4-Fluorophenyl)-4-[(pyridin-2-ylmethyl)-amino]-thieno[2,3-d]pyrimidin-2-yl}-acetic acid ethyl ester |
| 240 | {5-Benzo[1,3]dioxol-5-yl-4-[(pyridin-2-ylmethyl)-amino]-thieno[2,3-d]pyrimidin-2-yl}-acetic acid ethyl ester |
| 241 | {5-(4-Fluorophenyl)-4-[(6-methyl-pyridin-2-ylmethyl)-amino]-thieno[2,3-d]pyrimidin-2-yl}-acetic acid ethyl ester |

-continued

| Example | Compound |
|---------|----------|
| 242 | {5-Benzo[1,3]dioxol-5-yl-4-[(6-methyl-pyridin-2-ylmethyl)-amino]-thieno[2,3-d]pyrimidin-2-yl}-acetic acidethyl ester |
| 243 | {6-Methyl-4-[(6-methyl-pyridin-2-ylmethyl)-amino]-5-phenyl-thieno[2,3-d]pyrimidin-2-yl}-acetic acid ethyl ester |
| 244 | {5-(4-Fluorophenyl)-6-methyl-4-[(6-methyl-pyridin-2-ylmethyl)-amino]-thieno[2,3-d]pyrimidin-2-yl}-acetic acid ethyl ester |
| 245 | {5-Benzo[1,3]dioxol-5-yl-6-methyl-4-[(6-methyl-pyridin-2-ylmethyl)-amino]-thieno[2,3-d]pyrimidin-2-yl}-acetic acid ethyl ester |
| 246 | {6-Methyl-5-phenyl-4-[(pyridin-2-ylmethyl)-amino]-thieno[2,3-d]pyrimidin-2-yl}-acetic acid ethyl ester |
| 247 | {5-(4-Fluorophenyl)-6-methyl-4-[(pyridin-2-ylmethyl)-amino]-thieno[2,3-d]pyrimidin-2-yl}-acetic acid ethyl ester |
| 248 | {5-Benzo[1,3]dioxol-5-yl-6-methyl-4-[(pyridin-2-ylmethyl)-amino]-thieno[2,3-d]pyrimidin-2-yl}-acetic acid ethyl ester |
| 249 | 4-[(6-Methyl-pyridin-2-ylmethyl)-amino]-5-phenyl-thieno[2,3-d]pyrimidine-2-carboxylic acid ethyl ester |

Example 250

2-{5-Phenyl-4-[(pyridin-2-ylmethyl)amino]thieno[2,3-d]pyrimidin-2-yl}ethanol

A stirred solution of {5-phenyl-4-[(pyridin-2-ylmethyl)amino]thieno[2,3-d]pyrimidin-2-yl}acetic acid ethyl ester (0.10 g, 0.248 mmol) in anhydrous tetrahydrofuran (1 ml) was cooled in an ice-bath and treated, under a nitrogen atmosphere, with diisobutylaluminium hydride (1M solution in hexane, 1.04 ml, 1.04 mmol) over about 15 minutes. The reaction mixture was allowed to warm up and left to stir at ambient temperature for 3 hours. The resultant mixture was then cooled in an ice-bath and quenched by the slow addition of methanol (0.5 ml) followed by water (1 ml). The mixture was then diluted with 2M sodium hydroxide solution (10 ml) and extracted with ethyl acetate (3×20 ml). The combined organic extracts were dried (MgSO$_4$) and the solvent removed in vacuo to give the crude product. Purification by flash chromatography (silica) eluting with ethyl acetate and 40°-60° petroleum ether (4:1) gave 2-{5-phenyl-4-[(pyridin-2-ylmethyl)amino]thieno[2,3-d]pyrimidin-2-yl}ethanol as an off-white solid (0.05 g), m.p. 90°-92° C.

Examples 251 to 262

The compounds set out below were prepared in the same way as in Example 250, using the appropriate starting materials.

| Example | Compound |
|---------|----------|
| 251 | 2-{4-[(Furan-2-ylmethyl)-amino]-5-phenyl-thieno[2,3-d]pyrimidin-2-yl}-ethanol |
| 252 | 2-{4-[(6-Methyl-pyridin-2-ylmethyl)-amino]-5-phenyl-thieno[2,3-d]pyrimidin-2-yl}-ethanol |
| 253 | 2-{5-(4-Fluorophenyl)-4-[(pyridin-2-ylmethyl)-amino]-thieno[2,3-d]pyrimidin-2-yl}-ethanol |
| 254 | 2-{5-(4-Fluorophenyl)-4-[(6-methyl-pyridin-2-ylmethyl)-amino]-thieno[2,3-d]pyrimidin-2-yl}-ethanol |
| 255 | 2-{5-Benzo[1,3]dioxol-5-yl-4-[(pyridin-2-ylmethyl)-amino]-thieno[2,3-d]pyrimidin-2-yl}-ethanol |
| 256 | 2-{5-Benzo[1,3]dioxol-5-yl-4-[(6-methyl-pyridin-2-ylmethyl)-amino]-thieno[2,3-d]pyrimidin-2-yl}-ethanol |
| 25 | 2-{6-Methyl-5-phenyl-4-[(pyridin-2-ylmethyl)-amino]-thieno[2,3-d]pyrimidin-2-yl}-ethanol |
| 258 | 2-{6-Methyl-4-[(6-methyl-pyridin-2-ylmethyl)-amino]-5-phenyl-thieno[2,3-d]pyrimidin-2-yl}-ethanol |
| 259 | 2-{5-(4-Fluorophenyl)-6-methyl-4-[(pyridin-2-ylmethyl)-amino]-thieno[2,3-d]pyrimidin-2-yl}-ethanol |
| 260 | 2-{5-(4-Fluorophenyl)-6-methyl-4-[(6-methyl-pyridin-2-ylmethyl)-amino]-thieno[2,3-d]pyrimidin-2-yl}-ethanol |
| 261 | 2-{5-Benzo[1,3]dioxol-5-yl-6-methyl-4-[(pyridin-2-ylmethyl)-amino]-thieno[2,3-d]pyrimidin-2-yl}-ethanol |
| 262 | 2-{5-Benzo[1,3]dioxol-5-yl-6-methyl-4-[(6-methyl-pyridin-2-ylmethyl)-amino]-thieno[2,3-d]pyrimidin-2-yl}-ethanol |

Example 263

2-{5-Phenyl-4-[(pyridin-2-ylmethyl)amino]thieno[2,3-d]pyrimidin-2-yl}malonic acid diethyl ester Sodium hydride (60% dispersion in oil, 64 mg, 1.59 mmol) was treated with a solution of {5-phenyl-4-[(pyridin-2-ylmethyl)amino]thieno[2,3-d]pyrimidin-2-yl}acetic acid ethyl ester (0.43 g, 1.06 mmol) in diethyl carbonate (2.5 ml). The resulting suspension was stirred at ambient temperature for 5 hours and left to stand for 18 hours. The mixture was then quenched with aqueous ammonium chloride solution (50 ml) and extracted with diethyl ether (3×50 ml). The combined organic extracts were dried (MgSO$_4$) and the solvent removed in vacuo to give the crude product. Purification by flash chromatography (silica) eluting with dichloromethane followed by dichloromethane and ethyl acetate (5:1) gave 2-{5-phenyl-4-[(pyridin-2-ylmethyl)amino]thieno[2,3-d]pyrimidin-2-yl}malonic acid diethyl ester as a colourless gum (0.32 g).

Examples 264 to 274

The compounds set out below were prepared in the same way as in Example 263, using the appropriate starting materials.

| Example | Compound |
|---------|----------|
| 264 | 2-{5-(4-Fluorophenyl)-4-[(pyridin-2-ylmethyl)-amino]-thieno[2,3-d]pyrimidin-2-yl}-malonic acid diethyl ester |
| 265 | 2-{5-Benzo[1,3]dioxol-5-yl-4-[(pyridin-2-ylmethyl)-amino]-thieno[2,3-d]pyrimidin-2-yl}-malonic acid diethyl ester |
| 266 | 2-{5-(4-Fluorophenyl)-4-[(6-methyl-pyridin-2-ylmethyl)-amino]-thieno[2,3-d]pyrimidin-2-yl}-malonic acid diethyl ester |
| 267 | 2-{4-[(6-Methyl-pyridin-2-ylmethyl)-amino]-5-phenyl-thieno[2,3d]pyrimidin-2-yl}-malonic acid diethyl ester |
| 268 | 2-{5-Benzo[1,3]dioxol-5-yl-4-[(6-methyl-pyridin-2-ylmethyl)-amino]-thieno[2,3-d]pyrimidin-2-yl}-malonic acid diethyl ester |
| 269 | 2-{6-Methyl-5-phenyl-4-[(pyridin-2-ylmethyl)-amino]-thieno[2,3d]pyrimidin-2-yl}-malonic acid diethyl ester |
| 270 | 2-{5-(4-Fluorophenyl)-6-methyl-4-[(pyridin-2-ylmethyl)-amino]-thieno[2,3-d]pyrimidin-2-yl}-malonic acid diethyl ester |
| 271 | 2-{5-Benzo[1,3]dioxol-5-yl-6-methyl-4-[(pyridin-2-ylmethyl)-amino]-thieno[2,3-d]pyrimidin-2-yl}-malonic acid diethyl ester |
| 272 | 2-{6-Methyl-4-[(6-methyl-pyridin-2-ylmethyl)-amino]-5-phenylthieno[2,3-d]pyrimidin-2-yl}-malonic acid diethyl ester |
| 273 | 2-{5-(4-Fluorophenyl)-6-methyl-4-[(6-methyl-pyridin-2-ylmethyl)-amino]-thieno[2,3-d]pyrimidin-2-yl}-malonic acid diethyl ester |
| 274 | 2-{5-Benzo[1,3]dioxol-5-yl-6-methyl-4-[(6-methyl-pyridin-2-ylmethyl)-amino]-thieno[2,3-d]pyrimidin-2-yl}-malonic acid diethyl ester |

Example 275

2-{5-Phenyl-4-[(pyridin-2-ylmethyl)-amino]-thieno[2,3-d]pyrimidin-2-yl}-propane-1,3-diol A stirred solution of 2-{5-phenyl-4-[(pyridin-2-ylmethyl)amino]thieno[2,3-d]pyrimidin-2-yl}malonic acid diethyl ester (0.32 g, 0.672 mmol) in anhydrous tetrahydrofuran (10 ml) was cooled in an ice-bath and treated, under a nitrogen atmosphere, with diisobutylaluminium hydride (1M solution in hexane, 5.52 ml, 5.52 mmol) over 15 minutes. The reaction mixture was allowed to warm up and left to stir at ambient temperature for 3 hours. The resultant mixture was then cooled in an ice-bath and quenched by the slow addition of methanol (5 ml) followed by water (10 ml). The mixture was then diluted with 2M sodium hydroxide solution (50 ml) and extracted with ethyl acetate (3×50 ml). The combined organic extracts were dried (MgSO$_4$) and the solvent removed in vacuo to give the crude product. Purification by flash chromatography (silica) eluting with 5% methanol in dichloromethane gave 2-{5-phenyl-4-[(pyridin-2-ylmethyl)amino]thieno[2,3-d]pyrimidin-2-yl}propane-1,3-diol as a pale yellow solid (0.08 g), m.p. 137°-139° C.

Examples 276 to 286

The compounds set out below were prepared in the same way as in Example 275, using the appropriate starting materials.

| Example | Compound |
|---|---|
| 276 | 2-{4-[(6-Methyl-pyridin-2-ylmethyl)-amino]-5-phenyl-thieno[2,3-d]pyrimidin-2-yl}-propane-1,3-diol |
| 277 | 2-{5-(4-Fluorophenyl)-4-[(pyridin-2-ylmethyl)-amino]-thieno[2,3-d]pyrimidin-2-yl}-propane-1,3-diol |
| 278 | 2-{5-(4-Fluorophenyl)-4-[(6-methyl-pyridin-2-ylmethyl)-amino]-thieno[2,3-d]pyrimidin-2-yl}-propane-1,3-diol |
| 279 | 2-{5-Benzo[1,3]dioxol-5-yl-4-[(pyridin-2-ylmethyl)-amino]-thieno[2,3-d]pyrimidin-2-yl}-propane-1,3-diol |
| 280 | 2-{5-Benzo[1,3]dioxol-5-yl-4-[(6-methyl-pyridin-2-ylmethyl)-amino]-thieno[2,3-d]pyrimidin-2-yl}-propane-1,3-diol |
| 281 | 2-{6-Methyl-5-phenyl-4-[(pyridin-2-ylmethyl)-amino]-thieno[2,3-d]pyrimidin-2-yl}-propane-1,3-diol |
| 282 | 2-{6-Methyl-4-[(6-methyl-pyridin-2-ylmethyl)-amino]-5-phenyl-thieno[2,3-d]pyrimidin-2-yl}-propane-1,3-diol |
| 283 | 2-{5-(4-Fluorophenyl)-6-methyl-4-[(pyridin-2-ylmethyl)-amino]-thieno[2,3-d]pyrimidin-2-yl}-propane-1,3-diol |
| 284 | 2-{5-(4-Fluorophenyl)-6-methyl-4-[(6-methyl-pyridin-2-ylmethyl)-amino]thieno[2,3-d]pyrimidin-2-yl}-propane-1,3-diol |
| 285 | 2-{5-Benzo[1,3]dioxol-5-yl-6-methyl-4-[(pyridin-2-ylmethyl)-amino]-thieno[2,3-d]pyrimidin-2-yl}-propane-1,3-diol |
| 286 | 2-{5-Benzo[1,3]dioxol-5-yl-6-methyl-4-[(6-methyl-pyridin-2-ylmethyl)-amino]-thieno[2,3-d]pyrimidin-2-yl}-propane-1,3-diol |

Example 287

N-Methyl-2-[5-phenyl-4-[{pyridin-2-ylmethyl)amino]thieno[2,3-d]pyrimidin-2-yl]acetamide In a 10 ml glass tube were placed (5-phenyl-4-[(pyridin-2-ylmethyl)amino]thieno[2,3-d]pyrimidin-2-yl}acetic acid ethyl ester (35 mg, 0.088 mmol) and a saturated solution of methylamine in ethanol (2.0 ml). The tube was sealed with a septum and placed in the microwave cavity. Microwave irradiation of 200 W was used, the temperature being ramped from room temperature to 100° C. Once 100° C. was reached, the reaction mixture was held at this temperature for 30 minutes. The temperature was then ramped up to 150° C. and the reaction mixture was held at this temperature for a further 30 minutes. The resultant mixture was diluted with water (50 ml) and extracted with dichloromethane (3×50 ml). The combined organic extracts were dried (MgSO$_4$) and the solvent removed in vacuo to give a residue which was purified by flash chromatography (silica) eluting with 5% methanol in dichloromethane to give N-methyl-2-{5-phenyl-4-[{pyridin-2-ylmethyl)amino]thieno[2,3-d]pyrimidin-2-yl}acetamide (2 mg).

Examples 288 to 298

The compounds set out below were prepared in the same way as in Example 287, using the appropriate starting materials.

| Example | Compound |
|---|---|
| 288 | N-Methyl-2-{4-[(6-methyl-pyridin-2-ylmethyl)-amino]-5-phenyl-thieno[2,3-d]pyrimidin-2-yl}-acetamide |
| 289 | 2-{5-(4-Fluorophenyl)-4-[(pyridin-2-ylmethyl)-amino]-thieno[2,3-d]pyrimidin-2-yl}-N-methyl-acetamide |
| 290 | 2-{5-(4-Fluorophenyl)-4-[(6-methyl-pyridin-2-ylmethyl)-amino]-thieno[2,3-d]pyrimidin-2-yl}-N-methyl-acetamide |
| 291 | 2-{5-Benzo[1,3]dioxol-5-yl-4-[(pyridin-2-ylmethyl)-amino]-thieno[2,3-d]pyrimidin-2-yl}-N-methyl-acetamide |
| 292 | 2-{5-Benzo[1,3]dioxol-5-yl-4-[(6-methyl-pyridin-2-ylmethyl)-amino]-thieno[2,3-d]pyrimidin-2-yl}-N-methyl-acetamide |
| 293 | N-Methyl-2-{6-methyl-5-phenyl-4-[(pyridin-2-ylmethyl)-amino]-thieno[2,3-d]pyrimidin-2-yl]-acetamide |
| 294 | N-Methyl-2-{6-methyl-4-[(6-methyl-pyridin-2-ylmethyl)-amino]-5-phenyl-thieno[2,3-d]pyrimidin-2-yl}-acetamide |
| 295 | 2-{5-(4-Fluorophenyl)-6-methyl-4-[(pyridin-2-ylmethyl)-amino]-thieno[2,3-d]pyrimidin-2-yl}-N-methyl-acetamide |
| 296 | 2-{5-(4-Fluorophenyl)-6-methyl-4-[(6-methyl-pyridin-2-ylmethyl)-amino]-thieno[2,3-d]pyrimidin-2-yl}-N-methyl-acetamide |
| 297 | 2-{5-Benzo[1,3]dioxol-5-yl-6-methyl-4-[(pyridin-2-ylmethyl)-amino]-thieno[2,3-d]pyrimidin-2-yl}-N-methyl-acetamide |
| 298 | 2-{5-Benzo[1,3]dioxol-5-yl-6-methyl-4-[(6-methyl-pyridin-2-ylmethyl)-amino]-thieno[2,3-d]pyrimidin-2-yl}-N-methyl-acetamide |

Example 299

2-Chloromethyl-5-phenyl-3H-thieno[2,3-d]pyrimidin-4-one

Hydrogen chloride gas was bubbled through a stirred solution of 2-amino-4-phenylthiophene-3-carboxylic acid ethyl ester (4.94 g, 0.02 mol) and chloroacetonitrile (1.4 ml, 0.022 mol) in anhydrous 1,4-dioxane (60 ml) for about 4 hours. A thick suspension formed initially which slowly dissolved. The mixture was stirred at ambient temperature for 18 hours before being poured into water (250 ml) and basified (pH 8) by the addition of sodium hydrogen carbonate. The supernatant was then decanted to leave a gummy solid which was triturated with aqueous ethanol to give 2-chloromethyl-5-phenyl-3H-thieno[2,3-d]pyrimidin-4-one as a yellow solid (3.70 g), which was used without further purification.

Example 300

4-Chloro-2-chloromethyl-5-phenylthieno[2,3-d]pyrimidine

A stirred suspension of 2-chloromethyl-5-phenyl-3H-thieno[2,3-d]pyrimidin-4-one (1.5 g, 5.42 mmol) and phosphoryl chloride (23 ml) was heated under reflux for 7 hours and then left to stand at ambient temperature for 18 hours. The excess phosphoryl chloride was removed in vacuo to give a dark residue, which was dissolved in dichloromethane (100 ml) and then washed with water (2×100 ml) followed by saturated sodium hydrogen carbonate solution (100 ml). The organic extract was dried (MgSO$_4$) and the solvent was removed in vacuo to give the crude product. Purification by flash chromatography (silica) eluting with dichloromethane gave 4-chloro-2-chloromethyl-5-phenylthieno[2,3-d]pyrimidine as a pale-yellow solid (1.42 g).

Example 301

(2-Chloromethyl-5-phenylthieno[2,3-d]pyrimidin-4-yl)pyridin-2-ylmethylamine

A reaction mixture of 4-chloro-2-chloromethyl-5-phenylthieno[2,3-d]pyrimidine (0.50 g, 1.69 mmol), 2-aminomethylpyridine (0.17 ml, 1.69 mmol), triethylamine (0.26 ml, 1.86 mmol) and propan-2-ol (15 ml) was stirred at ambient temperature for 4 days. The solution was then poured into water (150 ml) and extracted with ethyl acetate (3×75 ml). The combined organic extracts were dried (MgSO$_4$) and the solvent removed in vacuo to give the crude product. Purification by flash chromatography (silica) eluting with ethyl acetate and 40°-60° petroleum ether (1:4) gave (2-chloromethyl-5-phenylthieno[2,3-d]pyrimidin-4-yl)pyridin-2-ylmethylamine as a yellow solid (0.17 g), m.p. 97°-99° C.

Example 302

(2-Dimethylaminomethyl-5-phenylthieno[2,3-d]pyrimidin-4-yl)pyridin-2-ylmethylamine In a 10 ml glass tube were placed (2-chloromethyl-5-phenylthieno[2,3-c]pyrimidin-4-yl)pyridin-2-ylmethylamine (50 mg, 0.136 mmol) and a saturated solution of dimethylamine in ethanol (2.0 ml). The tube was sealed with a septum and placed in the microwave cavity. Microwave irradiation of 200 W was used, the temperature being ramped from room temperature to 150° C. Once 150° C. was reached, the reaction mixture was held at this temperature for 10 minutes. The resultant mixture was diluted with water (50 ml) and extracted with dichloromethane (3×50 ml). The combined organic extracts were dried (MgSO$_4$) and the solvent removed in vacuo to give the crude product. Purification by flash chromatography (silica) eluting with 4% triethylamine in ethyl acetate gave (2-dimethylaminomethyl-5-phenylthieno[2,3-c]pyrimidin-4-yl)pyridin-2-ylmethylamine as a yellow gum (36 mg).

Examples 303 to 304

The compounds set out below were prepared in the same way as in Example 302, using the appropriate starting materials.

| Example | Compound |
|---------|----------|
| 303 | (2-Morpholin-4-ylmethyl-5-phenyl-thieno[2,3-d]pyrimidin-4-yl)-pyridin-2-ylmethyl-amine |
| 304 | (2-Methylaminomethyl-5-phenyl-thieno[2,3-d]pyrimidin-4-yl)-pyridin-2-ylmethyl-amine |

Example 305

(2-Methoxymethyl-5-phenylthien[2,3-d]primidin-4-yl)pyridin-2-ylmethylamine

In a 10 ml glass tube was placed anhydrous methanol (1 ml). This was cooled in an ice-bath and treated with sodium hydride (60% dispersion in oil, 6 mg, 0.147 mmol).

After stirring for about 10 minutes, (2-chloromethyl-5-phenylthieno[2,3-d]pyrimidin-4-yl)pyridin-2-ylmethylamine (36 mg, 0.098 mmol) was added. The tube was sealed with a septum and placed in the microwave cavity. Microwave irradiation of 200 W was used, the temperature being ramped from room temperature to 150° C. Once 150° C. was reached, the reaction mixture was held at this temperature for 10 minutes. The resultant mixture was diluted with water (50 ml) and extracted with dichloromethane (3×50 ml). The combined organic extracts were dried (MgSO$_4$) and the solvent removed in vacuo to give the crude product. Purification by flash chromatography (silica) eluting with ethyl acetate and 40°-60° petroleum ether (3:2) gave (2-methoxymethyl-5-phenylthien[2,3-d]primidin-4-yl)pyridin-2-ylmethylamine as a pale brown gum (1 mg).

Example 306

6-Bromo-3H-thieno[2,3-d]pyrimidin-4-one

A suspension of 3H-thieno[2,3-d]pyrimidin-4-one (7.68 g, 0.056 mol) in glacial acetic acid (75 ml) was treated with bromine (7.5 ml) and stirred at ambient temperature for 4 hours. The resulting solid was collected by filtration, washed with water and dried in vacuo to give 6-bromo-3H-thieno[2,3-d]pyrimidin-4-one as a light brown solid (11.64 g), which was used without further purification.

Example 307

The compound set out below was prepared in the same way as in Example 306, using the appropriate starting materials.

| Example | Compound |
|---------|----------|
| 307 | 6-Bromo-5-phenylthieno[2,3-d]pyrimidin-4(3H)-one |

Example 308

6-Bromo-4-chlorothieno[2,3-d]pyrimidine

6-Bromo-3H-thieno[2,3-d]pyrimidin-4-one (11.64 g, 0.05 mol) was added portion-wise to phosphoryl chloride (220 ml) and the resulting mixture was heated under reflux for 6 hours. The excess phosphoryl chloride was then removed in vacuo. The resulting residue was dissolved in dichloromethane (250 ml) and washed with water (2×100 ml), followed by saturated sodium hydrogen carbonate solution (100 ml). The organic layer was then dried (MgSO$_4$) and the solvent was removed in vacuo to give 6-bromo-4-chlorothieno[2,3-d]pyrimidine (9.06 g) as a yellow solid, which was used without further purification.

Example 309

The compound set out below was prepared in the same way as in Example 308, using the appropriate starting materials.

| Example | Compound |
|---|---|
| 309 | 6-Bromo-4-chloro-5-phenylthieno[2,3-d]pyrimidin-4(3H)-one |

Example 310

5-Bromo-4-chlorothieno[2,3-d]pyrimidine

A stirred solution of 6-bromo-4-chlorothieno[2,3-d]pyrimidine (4.0 g, 0.016 mol) in anhydrous tetrahydrofuran (100 ml) was cooled in a dry-ice/acetone bath and treated, under a nitrogen atmosphere, with lithium diisopropylamide (1.8M solution in tetrahydrofuran, 9.0 ml, 0.016 mol) over about 20 minutes. The resultant dark solution was stirred in the cold for 1 hour and then treated with a mixture of water (5 ml) and tetrahydrofuran (20 ml) over about 20 minutes. The mixture was then allowed to warm up to about 0° C. before being poured into water (250 ml) and extracted with dichloromethane (3×100 ml). The combined organic extracts were dried (MgSO$_4$) and the solvent removed in vacuo to give the crude product. Purification by flash chromatography (silica) eluting with dichloromethane gave 5-bromo-4-chlorothieno[2,3-d]pyrimidine as a pale brown solid (3.8 g).

Example 311

(5-Bromothieno[2,3-d]pyrimidin-4-yl)pyridin-2-ylmethylamine

A stirred mixture of 5-bromo-4-chlorothieno[2,3-d]pyrimidine (3.8 g, 15.2 mmol), ethanol (250 ml), triethylamine (2.32 ml, 16.7 mmol) and 2-aminomethylpyridine (1.72 ml, 16.7 mmol) was heated under reflux for 2.5 hours. The solution was then cooled to ambient temperature, poured into water (300 ml) and extracted with dichloromethane (3×150 ml). The combined organic extracts were dried (MgSO$_4$) and the solvent removed in vacuo to give the crude product. Purification by flash chromatography (silica) eluting with ethyl acetate and 40°-60° petroleum ether (1:1) gave (5-bromothieno[2,3-d]pyrimidin-4-yl)pyridin-2-ylmethylamine as a yellow solid (3.12 g), m.pt. 127°-129° C.

Example 312

[5-(1-Methyl-1H-indol-5-yl)thieno[2,3-d]pyrimidin-4-yl]pyridin-2-ylmethylamine

In a 10 ml glass tube were placed 5-bromothieno[2,3-d]pyrimidin-4-yl)pyridin-2-ylmethylamine (47 mg, 0.146 mmol), N-methylindole-5-boronic acid (51 mg, 0.294 mmol), polymer-bound triphenylphosphine-Pd(0) (Argonaut PS—PPh$_3$-Pd, 0.13 mmol/g, 146 mg, 0.0146 mmol), sodium carbonate (46 mg, 0.440 mmol), dimethoxyethane (0.75 ml), ethanol (0.75 ml) and water (0.5 ml). The tube was sealed with a septum and placed in the microwave cavity. Microwave irradiation of 200 W was used, the temperature being ramped from room temperature to 150° C. Once 150° C. was reached, the reaction mixture was held at this temperature for 1 hour. The resultant mixture was filtered through Kieselguhr, the filtered solid being washed through with water and dichloromethane. The filtrate was then extracted with dichloromethane (3×50 ml) and the organic extracts dried (MgSO$_4$). The solvent was removed in vacuo to give the crude product. Purification by flash chromatography (silica) eluting with ethyl acetate and 40°-60° petroleum ether (2:1) gave [5-(1-methyl-1H-indol-5-yl)thieno[2,3-d]pyrimidin-4-yl]pyridin-2-ylmethylamine as a yellow solid (25 mg), m.pt. 184-185° C.

Examples 313 to 333

The compounds set out below were prepared in the same way as in Example 312, using the appropriate starting materials.

| Example | Compound |
|---|---|
| 313 | Pyridin-2-ylmethyl-[5-(4-trifluoromethyl-phenyl)-thieno[2,3-d]pyrimidin-4-yl]-amine |
| 314 | (5-Benzo[1,3]dioxol-5-yl-thieno[2,3-d]pyrimidin-4-yl)-pyridin-2-ylmethyl-amine |
| 315 | [5-(4-Dimethylamino-phenyl)-thieno[2,3-d]pyrimidin-4-yl]-pyridin-2-ylmethyl-amine |
| 316 | [5-(3,4-Dimethyl-phenyl)-thieno[2,3-d]pyrimidin-4-yl]-pyridin-2-ylmethyl-amine |
| 317 | Pyridin-2-ylmethyl-[5-(4-trifluoromethoxy-phenyl)-thieno[2,3-d]pyrimidin-4-yl]-amine |
| 318 | Pyridin-2-ylmethyl-(5-p-tolyl-thieno[2,3-d]pyrimidin-4-yl)-amine |
| 319 | (5-Benzo[1,3]dioxol-5-yl-thieno[2,3-d]pyrimidin-4-yl)-pyridin-2-ylmethyl-amine |
| 320 | [5-(2,3-Dihydro-benzo[1,4]dioxin-6-yl)-thieno[2,3-d]pyrimidin-4-yl]-pyridin-2-ylmethyl-amine |
| 321 | [5-(3-Chlorophenyl)-thieno[2,3-d]pyrimidin-4-yl]-pyridin-2-ylmethyl-amine |
| 322 | [5-(3-Methoxyphenyl)-thieno[2,3-d]pyrimidin-4-yl]-pyridin-2-ylmethyl-amine |
| 323 | [5-(1H-Indol-6-yl)-thieno[2,3-d]pyrimidin-4-yl]-pyridin-2-ylmethyl-amine |
| 324 | [5-(4-Methoxymethoxy-phenyl)-thieno[2,3-d]pyrimidin-4-yl]-pyridin-2-ylmethyl-amine |
| 325 | [5-(4-Chlorophenyl)-thieno[2,3-d]pyrimidin-4-yl]-pyridin-2-ylmethyl-amine |
| 326 | [5-(2,2-Difluoro-benzo[1,3]dioxol-5-yl)-thieno[2,3-d]pyrimidin-4-yl]-pyridin-2-ylmethyl-amine |
| 327 | 4-{4-[(Pyridin-2-ylmethyl)-amino]-thieno[2,3-d]pyrimidin-5-yl}-benzoic acid methyl ester |
| 328 | [5-(6-Methoxy-pyridin-3-yl)-thieno[2,3-d]pyrimidin-4-yl]-pyridin-2-ylmethyl-amine |
| 329 | [5-(2,4-Dichloro-phenyl)-thieno[2,3-d]pyrimidin-4-yl]-pyridin-2-ylmethyl-amine |
| 330 | [5-(4-Chloro-3-trifluoromethyl-phenyl)-thieno[2,3-d]pyrimidin-4-yl]-pyridin-2-ylmethyl-amine |
| 331 | [5-(3-Fluorophenyl)-thieno[2,3-d]pyrimidin-4-yl]-pyridin-2-ylmethyl-amine |
| 332 | [5-(4-Morpholin-4-yl-phenyl)-thieno[2,3-d]pyrimidin-4-yl]-pyridin-2-ylmethyl-amine |
| 333 | [5-(3,4-Difluoro-phenyl)-thieno[2,3-d]pyrimidin-4-yl]-pyridin-2-ylmethyl-amine |

Example 334

5-Bromo-6-methyl-1H-thieno[2,3-d]pyrimidine-2,4-dione

A brown glass round-bottom flask was charged with 6-methyl-1H-thieno[2,3-d]pyrimidine-2,4-dione (2.70 g, 14.8 mmol) and glacial acetic acid (30 ml). Bromine (2.70 ml) was added and the mixture stirred at ambient temperature for 4 hours. The resultant mixture was diluted with water (30 ml) and the solid was collected by filtration, washed thoroughly with water and then dried in vacuo to give 5-bromo-6-methyl-1H-thieno[2,3-d]pyrimidine-2,4-dione as a brown solid (2.43 g), which was used without further purification.

Example 335

5-Bromo-2,4-dichloro-6-methylthieno[2,3-d]pyrimidine

A stirred mixture of 5-bromo-6-methyl-1H-thieno[2,3-d]pyrimidine-2,4-dione (2.43 g, 9.3 mmol) and phenylphosphonic dichloride (15 ml) was heated at a temperature of 150° C. for 6 hours in a vessel protected by a calcium chloride drying tube. The reaction mixture was allowed to cool to ambient temperature and poured into ice-water (250 ml). After stirring for 45 minutes, the resulting mixture was extracted with dichloromethane (3×100 ml). The combined organic extracts were washed with water (100 ml) followed by saturated sodium hydrogen carbonate solution (100 ml) and dried (MgSO$_4$). The solvent was removed in vacuo to give the crude product which was purified by flash chromatography (silica) eluting with dichloromethane giving 2.02 g of 5-bromo-2,4-dichloro-6-methylthieno[2,3-d]pyrimidine as a yellow solid.

Example 336

5-Bromo-2-chloro-6-methylthieno[2,3-d]pyrimidin-4-yl)pyridin-2-ylmethylamine A stirred mixture of 5-bromo-2,4-dichloro-6-methylthieno[2,3-d]pyrimidine (1.0 g, 3.35 mmol), ethanol (40 ml), 2-aminomethylpyridine (0.40 ml, 3.69 mmol) and triethylamine (0.50 ml, 3.69 mmol) was heated at a temperature of 60° C. for 1 hour. The reaction mixture was then cooled to ambient temperature, diluted with water (100 ml) and extracted with dichloromethane (3×50 ml). The combined organic extracts were dried (MgSO$_4$) and the solvent removed in vacuo to give a residue. Purification by flash chromatography (silica) eluting with dichloromethane followed by 5% ethyl acetate in dichloromethane gave (5-bromo-2-chloro-6-methylthieno[2,3-d]pyrimidin-4-yl)pyridin-2-ylmethylamine as a white solid (0.99 g).

Example 337

The compound set out below was prepared in the same way as in Example 336, using the appropriate starting materials.

| Example | Compound |
|---|---|
| 337 | 5-Bromo-2-chloro-6-methyl-thieno[2,3-d]pyrimidin-4-yl)-(6-methyl-pyridin-2-ylmethyl)-amine |

Example 338

2-[{5-Bromo-6-methyl-4-[(pyridin-2-ylmethyl)amino]thieno[2,3-d]pyrimidin-2-yl}-(2-hydroxyethyl)amino]ethanol In a 10 ml glass tube were placed 5-bromo-2-chloro-6-methylthieno[2,3-d]pyrimidin-4-yl)pyridin-2-ylmethylamine (0.10 g, 0.27 mmol) and diethanolamine (0.80 ml). The tube was sealed with a septum and placed in the microwave cavity. Microwave irradiation of 200 W was used, the temperature being ramped from room temperature to 200° C. Once 200° C. was reached, the reaction mixture was held at this temperature for 30 minutes. After cooling to ambient temperature, water (50 ml) was added and the mixture extracted with dichloromethane (3×50 ml). The combined organic extracts were dried (MgSO$_4$) and the solvent removed in vacuo to give the crude product which was recrystallised from dichloromethane to give 2-[{5-bromo-6-methyl-4-[(pyridin-2-ylmethyl)amino]thieno[2,3-d]pyrimidin-2-yl}-(2-hydroxyethyl)amino]ethanol as a white solid (0.71 g), m.pt. 152° C.

Examples 339 to 341

The compounds set out below were prepared in the same way as in Example 338, using the appropriate starting materials.

| Example | Compound |
|---|---|
| 339 | 2-{5-Bromo-6-methyl-4-[(6-methyl-pyridin-2-ylmethyl)-amino]-thieno[2,3-d]pyrimidin-2-ylamino}-ethanol |
| 340 | 2-[{5-Bromo-6-methyl-4-[(6-methyl-pyridin-2-ylmethyl)-amino]thieno[2,3-d]pyrimidin-2-yl}-(2-hydroxy-ethyl)-amino]-ethanol |
| 341 | 2-({5-Bromo-6-methyl-4-[(pyridin-2-ylmethyl)-amino]-thieno[2,3d]pyrimidin-2-yl}amino)-ethanol |

Example 342

2-β2-hydroxyethyl)-{6-methyl-5-phenyl-4-[(pyridin-2-ylmethyl)amino]thieno[2,3-d]pyrimidin-2-yl}amino)ethanol In a 10 ml glass tube were placed 2-[{5-bromo-6-methyl-4-[(pyridin-2-ylmethyl)amino]thieno[2,3-d]pyrimidin-2-yl}-(2-hydroxyethyl)amino]ethanol (32 mg, 0.073 mmol), phenylboronic acid (20 mg, 0.166 mmol), sodium carbonate (26 mg, 0.249 mmol), triphenylphosphine (7 mg, 0.025 mmol), palladium(II)acetate (2 mg, 0.008 mmol), dimethoxyethane (0.75 ml) and water (0.25 ml). The tube was sealed with a septum and placed in the microwave cavity. Microwave irradiation of 200 W was used, the temperature being ramped from room temperature to 150° C. Once 150° C. was reached, the reaction mixture was held at this temperature for 1 hour. The resultant mixture was diluted with water (50 ml), extracted into dichloromethane (3×50 ml) and the combined organic extracts were dried (MgSO$_4$). The solvent was removed in vacuo to give the crude product which was purified by flash chromatography (silica) eluting with ethyl acetate followed by 5% methanol in ethyl acetate to give 2-((2-hydroxyethyl)-{6-methyl-5-phenyl-4-[(pyridin-2-ylmethyl)amino]thieno[2,3-d]pyrimidin-2-yl}amino)ethanol as a brown gum (7 mg).

Examples 343 to 353

The compounds set out below were prepared in the same way as in Example 342, using the appropriate starting materials.

| Example | Compound |
|---|---|
| 343 | 2-[{5-Benzo[1,3]dioxol-5-yl-6-methyl-4-[(pyridin-2-ylmethyl)-amino]-thieno[2,3-d]pyrimidin-2-yl}-(2-hydroxy-ethyl)-amino]-ethanol |

| Example | Compound |
|---|---|
| 344 | 2-[{5-(4-Fluorophenyl)-6-methyl-4-[(pyridin-2-ylmethyl)-amino]-thieno[2,3-d]pyrimidin-2-yl}-(2-hydroxy-ethyl)-amino]-ethanol |
| 345 | 2-{6-Methyl-5-phenyl-4-[(pyridin-2-ylmethyl)-amino]-thieno[2,3-d]pyrimidin-2-ylamino}-ethanol |
| 346 | 2-{6-Methyl-4-[(6-methyl-pyridin-2-ylmethyl)-amino]-5-phenyl-thieno[2,3-d]pyrimidin-2-ylamino}-ethanol |
| 347 | 2-((2-Hydroxy-ethyl)-{6-methyl-4-[(6-methyl-pyridin-2-ylmethyl)-amino]-5-phenyl-thieno[2,3-d]pyrimidin-2-yl}-amino)-ethanol |
| 348 | 2-{5-(4-Fluorophenyl)-6-methyl-4-[(pyridin-2-ylmethyl)-amino]-thieno[2,3-d]pyrimidin-2-ylamino}-ethanol |
| 349 | 2-{5-(4-Fluorophenyl)-6-methyl-4-[(6-methyl-pyridin-2-ylmethyl)-amino]-thieno[2,3-d]pyrimidin-2-ylamino}-ethanol |
| 350 | 2-[{5-(4-Fluorophenyl)-6-methyl-4-[(6-methyl-pyridin-2-ylmethyl)-amino]-thieno[2,3-d]pyrimidin-2-yl}-(2-hydroxy-ethyl)-amino]-ethanol |
| 351 | 2-{5-Benzo[1,3]dioxol-5-yl-6-methyl-4-[(pyridin-2-ylmethyl)-amino]-thieno[2,3-d]pyrimidin-2-ylamino}-ethanol |
| 352 | 2-{5-Benzo[1,3]dioxol-5-yl-6-methyl-4-[(6-methyl-pyridin-2-ylmethyl)-amino]-thieno[2,3-d]pyrimidin-2-ylamino}-ethanol |
| 353 | 2-[{5-Benzo[1,3]dioxol-5-yl-6-methyl-4-[(6-methyl-pyridin-2-ylmethyl)-amino]-thieno[2,3-d]pyrimidin-2-yl}-(2-hydroxy-ethyl)-amino]-ethanol |

Example 354

Analytical Data for compounds representative of the above examples are shown in the table below.

| Example | NMR Spectrum $^1$H (400 MHz; CDCl$_3$; Me$_4$Si), | Mass Spectrum (m/z) (APCI) |
|---|---|---|
| 101 | 2.65 (3H, s), 4.72 (2H, d), 6.5 (1H, br s), 6.98 (1H, s), 7.12 (1H, m), 7.19 (1H, d), 7.48 (5H, s), 7.60 (1H, t), 8.25 (1H, d). | 333 (100%, [M + H]+) |
| 83 | 4.60 (2H, d), 5.27 (1H, br s), 6.07 (1H, d), 6.27 (1H, d), 7.10 (1H, m), 7.29 (1H, s), 7.43 (5H, m), 8.55 (1H, s). | 308 (100%, [M + H]+) |
| 105 | 4.73 (2H, s), 6.60 (1H, br s), 7.09 (1H, s), 7.12 (1H, m), 7.17 (1H, d), 7.51 (5H, m), 7.59 (1H, t), 8.25 (1H, d), 8.55 (1H, s). | 319 (100%, [M + H]+) |
| 106 | 5.55 (2H, s), 6.62 (1H, d), 7.15 (1H, m), 7.29 (1H, s), 7.36 (3H, m), 7.50 (3H, m), 8.55 (1H, m), 8.71 (1H, s). | 320 (100%, [M + H]+) |
| 190 | 3.60 (2H, m), 3.81 (2H, m), 4.42 (1H, br s), 4.61 (2H, d), 5.27 (1H, m), 6.31 (1H, br s), 6.65 (1H, s), 7.15 (1H, m), 7.46 (5H, s), 7.60 (1H, t), 8.25 (1H, d) | 378 (100%, [M + H]+) |
| 189 | 3.38 (3H, m), 3.55 (2H, m), 3.65 (2H, m), 4.65 (2H, d), 5.19 (1H, m), 6.10 (1H, br s), 6.61 (1H, s), 7.11 (2H, m), 7.45 (5H, m), 7.60 (1H, t), 8.30 (1H, d). | 393 (100%, [M + 2H]+) |
| 191 | 4.02 (3H, s), 4.70 (2H, d), 6.60 (1H, br s), 6.85 (1H, s), 7.13 (2H, m), 7.48 (5H, m), 7.58 (1H, t), 8.24 (1H, d). | 349 (100%, [M + H]+) |
| 196 | 3.00 (3H, d), 4.67 (2H, d), 4.82 (1H, br s), 6.07 (1H, br s), 6.60 (1H, s), 7.12 (1H, m), 7.43 (5H, m), 7.60 (1H, t), 8.31 (1H, d). | 348 (100%, [M + H]+) |
| 197 | 3.72 (4H, m), 3.80 (4H, m), 4.62 (2H, d), 6.04 (1H, br s), 6.62 (1H, s), 7.13 (2H, m), 7.45 (5H, m), 7.59 (1H, d), 8.30 (1H, d). | 404 (100%, [M + H]+) |
| 198 | 3.17 (6H, s), 4.68 (2H, d), 5.90 (1H br s), 6.59 (1H, s), 7.12 (1H, m), 7.18 (1H, d), 7.42 (5H, m), 7.58 (1H, t), 8.32 (1H, d). | 363 (100%, [M + 2H]+) |
| 123 | 4.70 (2H, d), 6.65 (1H, br s), 7.09 (1H, s), 7.18 (4H, m), 7.48 (1H, s), 7.60 (1H, t), 8.25 (1H, d), 8.56 (1H, s). | 337 (100%, [M + H]+) |
| 138 | 3.90 (3H, m), 4.73 (2H, d), 6.64 (1H, br s), 7.04 (3H, m), 7.18 (2H, m), 7.40 (2H, m), 7.60 (1H, t), 8.28 (1H, d), 8.52 (1H, s). | 350 (100%, [M + 2H]+) |
| 84 | 0.07 (2H, m), 0.38 (2H, m), 0.82 (1H, m), 3.30 (2H, m), 5.41 (1H, br s), 7.18 (1H, s), 7.50 (5H, m), 8.56 (1H, s). | 282 (100%, [M + H]+) |
| 135 | 4.61 (2H, d), 5.18 (1H, br s), 6.10 (1H, s), 6.28 (1H, d), 7.06 (1H, d), 7.32 (3H, m), 7.40 (2H, d), 8.51 (1H, s). | 341 (100%, [M]+) |
| 109 | 5.41 (2H, s), 6.28 (1H, d), 6.31 (1H, d), 7.26 (1H, s), 7.28 (3H, m), 7.40 (3H, m), 8.69 (1H, s). | 309 (100%, [M + H]+) |
| 108 | 2.20 (3H, s), 4.55 (2H, d), 5.26 (1H, br s), 5.82 (1H, d), 5.92 (1H, d), 7.07 (1H, s), 7.41 (5H, m), 8.52 (1H, s). | 322 (100%, [M + H]+) |
| 133 | 2.25 (3H, s), 2.30 (3H, s), 4.65 (2H, br s), 5.41 (1H, br s), 6.08 (1H, d), 6.25 (1H, d), 7.02 (1H, s), 7.15 (3H, m), 7.28 (1H, d), 8.50 (1H, s) | 336 (100%, [M + H]+) |
| 149 | 1.40 (3H, s), 5.37 (1H, m), 6.60 (1H, d), 7.06 (1H, s), 7.10 (2H, m), 7.48 (5H, m), 7.60 (1H, t), 8.22 (1H, d), 8.50 (1H, s). | 334 (100%, [M + 2H]+) |
| 150 | 2.63 (3H, s), 4.62 (2H, d), 5.20 (1H, br s), 6.06 (1H, d), 6.27 (1H, d), 6.98 (1H, s), 7.28 (1H, d), 7.40 (5H, m) | 322 (100%, [M + H]+) |
| 152 | 1.35 (3H, t), 2.90 (2H, q), 4.75 (2H, d), 6.35 (1H, br s), 7.00 (1H, s), 7.10 (1H, m), 7.20 (1H, d), 7.50 (5H, s), 7.60 (1H, t), 8.25 (1H, d) | 347 (100%, [M + H]+) |
| 312 | 3.85 (3H, s), 4.65 (2H, d), 6.45 (1H, br s), 6.55 (1H, br s), 7.00 (1H, m), 7.05 (1H, s), 7.10 (1H, d), 7.15 (1H, d), 7.30 (1H, m), 7.40 (1H, d), 7.50 (1H, t), 7.75 (1H, s), 7.80 (1H, m), 8.50 (1H, s) | 372 (100%, [M + H]+) |
| 313 | 4.75 (2H, d), 6.75 (1H, br s), 7.15 (3H, m), 7.20 (1H, m), 7.60 (1H, d), 7.80 (1H, d), 8.15 (1H, d), 8.60 (1H, s) | 387 (100%, [M + H]+) |
| 314 | 4.75 (2H, d), 6.05 (2H, s), 6.75 (1H, br s), 6.95 (3H, m), 7.05 (1H, s), 7.20 (2H, m), 7.60 (1H, t), 8.35 (1H, d), 8.50 (1H, s) | 363 (100%, [M + H]+) |
| 237 | 1.25 (3H, t), 3.90 (2H, s), 4.20 (2H, q), 4.70 (2H, d), 6.50 (1H, br s), 7.05 (1H, s), 7.10 (1H, m), 7.20 (1H, dd), 7.50 (5H, m), 7.60 (1H, t), 8.25 (1H, d) | 405 (100%, [M + H]+) |
| 275 | 3.20 (1H, m), 4.05 (4H, m), 4.40 (2H, br s), 4.65 (2H, d), 6.75 (1H, br s), 7.05 (1H, s), 7.15 (2H, m), 7.50 (5H, m), 7.60 (1H, m), 8.25 (1H, d) | 393 (100%, [M + H]+) |
| 250 | 3.10 (2H, t), 4.05 (2H, m), 4.65 (2H, d), 4.85 (1H, br s), 6.65 (1H, br s), 7.05 (1H, s), 7.15 (2H, m), 7.50 (5H, m), 7.60 (1H, m), 8.25 (1H, d) | 363 (100%, [M + H]+) |
| 287 | 2.80 (3H, d), 3.85 (2H, s), 4.70 (2H, d), 6.55 (1H, br s), 7.05 (1H, s), 7.15 (2H, m), 7.50 (6H, m), 7.60 (1H, m), 8.30 (1H, d) | 390 (100%, [M + H]+) |
| 302 | 2.40 (6H, s), 3.70 (2H, d), 4.75 (2H, d), 6.45 (1H, br s), 7.00 (1H, s), 7.10 (1H, m), 7.20 (1H, d), 7.50 (5H, br s), 7.60 (1H, t), 8.25 (1H, d) | 376 (100%, [M + H]+) |
| 303 | 2.65 (4H, m), 3.80 (6H, m), 4.75 (2H, d), 6.40 (1H, br s), 7.05 (1H, s), 7.10 (1H, m), 7.20 (1H, dd), 7.50 (5H, br s), 7.60 (1H, m), 8.30 (1H, d) | 418 (100%, [M + H]+) |
| 304 | 2.50 (3H, s), 3.90 (2H, s), 4.75 (2H, d), 6.50 (1H, br s), 7.05 (1H, s), 7.15 (2H, m), 7.20 (1H, d), 7.50 (6H, br s), 7.60 (1H, t), 8.30 (1H, d) | 362 (100%, [M + H]+) |
| 305 | 3.55 (3H, s), 4.60 (2H, s), 4.75 (2H, d), 6.55 (1H, br s), 7.05 (1H, s), 7.10 (1H, m), 7.20 (1H, d), 7.50 (5H, br s), 7.60 (1H, t), 8.25 (1H, d) | 363 (100%, [M + H]+) |
| 157 | 2.30 (3H, s), 4.65 (2H, d), 6.30 (1H, br s), 7.10 (2H, m), 7.40 (2H, m), 7.50 (3H, m), 7.60 (1H, t), 8.20 (1H, d), 8.50 (1H, s) | 333 (100%, [M + H]+) |
| 342 | 2.20 (3H, s), 3.80 (4H, m), 3.85 (4H, m), 4.50 (2H, d), 4.75 (2H, br s), 6.05 (1H, br s), 7.10 (2H, m), 7.35 (2H, m), 7.50 (3H, m), 7.55 (1H, m), 8.25 (1H, d) | 436 (100%, [M + H]+) |
| 343 | 2.20 (3H, s), 3.80 (4H, m), 3.90 (4H, m), 4.55 (2H, d), 4.75 (2H, br s), 6.00 (2H, s), 6.30 (1H, br s), 6.80 (2H, m), 6.95 (1H, d), 7.15 (2H, m), 7.60 (1H, t), 8.35 (1H, d) | 480 (100%, [M + H]+) |
| 344 | 2.20 (3H, s), 3.80 (4H, m), 3.90 (4H, m), 4.50 (2H, d), 4.75 (2H, br s), 6.20 (1H, br s), 7.15 (4H, m), 7.30 (2H, m), 7.55 (1H, t), 8.25 (1H, d) | 454 (100%, [M + H]+) |
| 148 | 1.30 (3H, s), 1.35 (3H, s), 3.10 (1H, q), 4.75 (2H, d), 6.25 (1H, br s), 7.00 (1H, s), 7.10 (1H, m), 7.20 (1H, d), 7.50 (5H, s), 7.60 (1H, t), 8.30 (1H, d) | 361 (100%, [M + H]+) |
| 212 | 3.62 (2H, m), 3.85 (2H, m), 4.37 (1H, br s), 4.62 (2H, d), 5.31 (1H, br t), 6.40 (1H, br s), 6.60 (1H, s), 7.16 (4H, m), 7.45 (2H, m), 7.62 (1H, m), 8.28 (1H, m). | 396 (100%, [M + H]+) |
| 208 | 3.80 (4H, m), 3.88 (4H, m), 4.50 (2H, d), 4.60 (2H, d), 6.35 (1H, br s), 6.63 (1H, s), 7.14 (2H, m), 7.45 (5H, m), 7.59 (1H, m), 8.27 (1H, d). | 422 (100%, [M + H]+) |
| 318 | 2.48 (3H, s), 4.73 (2H, d), 6.55 (1H, br s), 7.05 (1H, s), 7.16 (2H, m), 7.28 (2H, m), 7.37 (2H, m), 7.60 (1H, m), 8.26 (1H, m), 8.53 (1H, s). | 333 (100%, [M + H]+) |

-continued

| Example | NMR Spectrum ¹H (400 MHz; CDCl₃; Me₄Si), | Mass Spectrum (m/z) (APCI) |
|---|---|---|
| 213 | 2.33 (3H, s), 3.62 (2H, m), 3.83 (2H, m), 4.47 (1H, br s), 4.62 (2H, d), 5.42 (1H, br t), 6.11 (1H, br s), 6.61 (1H, s), 6.95 (2H, m), 7.44 (6H, m). | 392 (100%, [M + H]+) |
| 217 | 2.35 (3H, s), 3.79 (4H, m), 3.87 (4H, m), 4.59 (2H, d), 4.62 (2H, br s), 6.14 (1H, br s), 6.61 (1H, s), 6.96 (2H, m), 7.45 (6H, m). | 436 (100%, [M + H]+) |

Example 355

Bioassays-Kv1.5 Rb⁺ Efflux Assay

The pore of a potassium channel is permeable to other monovalent cations such as Rb⁺ and Tl⁺. Analysis of cellular efflux of potassium channel permeable ions enables potassium channel activity to be monitored directly. Cells stably transfected with cDNA for human Kv1.5 (in pEF6::VA-His-TOPO) were grown in Dulbecco's Modified Eagle media (DMEM) alpha supplemented with 10% Fetal Calf Serum (FCS), 20 µl/ml penicillin (5000 U/ml) streptomycin (5000 µg/ml), 10 µl/ml [100×] glutamine, and blasticidin (7.5 µg/ml). Cells were dispensed into 96 well cellstar TC plates and allowed to grow until a confluent monolayer was visible. On the morning of the assay run, cold media was aspirated using the TECAN plate washer, and a 50 µl media spike containing 2 µCi/ml (37 kBq/ml) ⁸⁶Rb⁺ added to each well containing cells using the Shallow-Well Matrix Platemate. Plates were placed in an incubator at 37° C. for a minimum of 3 hours. Unloaded ⁸⁶Rb⁺ in the "hot" media was aspirated and each well washed 4×250 µl with Earls Balanced Salt Solution (EBSS) which contained 5 mM KCl, 140 mM NaCl, 2 mM CaCl₂, 1 mM MgSO₄, 10 mM HEPES, and 5 mM glucose, pH 7.4, 290-300 mOsm. These cells were then pre-incubated with 50 µl of EBSS+/−test compounds for 10 minutes at room temperature. After the 10 minute incubation, 50 µl of modified EBSS which contained 145 mM KCl, 2 mM CaCl₂, 1 mM MgSO₄, 10 mM HEPES, 5 mM glucose, pH 7.4, 290-300 mOsm, was added, and the cells were incubated for a further 10 minutes at room temperature. The high KCl EBSS was used to depolarise cells to a membrane potential that would activate Kv1.5 channels. After the final incubation 80 µl/100 µl of the reaction from each well was transferred to equivalent wells in a Packard "Optiplate" white 96 well plate and counted in a Packard TopCount liquid scintillation counter by Cerenkov emission. Percentage inhibition ⁸⁶Rb⁺ efflux through Kv1.5 was calculated by normalisation to 2.5 mM 4 amino-pyridine control block of Kv1.5. Alternatively cells were loaded with ⁸⁵Rb⁺ and quantified by atomic absorption spectroscopy. IC₅₀ determinations were derived from 10 point concentration response curves n=2 using the method described above. Data was fitted as variable slope sigmoidal fit using Graphpad Prism (V3.02) software.

| Example | Compound | IC₅₀ (µM) |
|---|---|---|
| 83 | Furan-2-ylmethyl-(5-phenyl-thieno[2,3-d]pyrimidin-4-yl)-amine | 0.07 |
| 102 | (1-Ethyl-pyrrolidin-2-ylmethyl)-(5-phenyl-thieno[2,3-d]pyrimidin-4-yl)-amine | >30 |
| 103 | N,N-Dimethyl-2-(5-phenyl-thieno[2,3-d]pyrimidin-4-ylamino)-acetamide | >30 |
| 104 | (3-Imidazol-1-yl-propyl)-(5-phenyl-thieno[2,3-d]-pyrimidin-4-yl)-amine | >30 |
| 105 | (5-Phenyl-thieno[2,3-d]pyrimidin-4-yl)-pyridin-2-ylmethyl-amine | 0.28 |
| 106 | 5-Phenyl-4-(pyridin-2-ylmethoxy)-thieno[2,3-d]pyrimidine | 0.33 |
| 84 | Cyclopropylmethyl-(5-phenyl-thieno[2,3-d]pyrimidin-4-yl)-amine | 0.80 |
| 107 | Furan-3-ylmethyl-(5-phenyl-thieno[2,3-d]pyrimidin-4-yl)-amine | 1.05 |
| 108 | (5-Methyl-furan-2-ylmethyl)-(5-phenyl-thieno[2,3-d]pyrimidin-4-yl)-amine | 0.41 |
| 109 | 4-(Furan-2-ylmethoxy)-5-phenyl-thieno-[2,3-d]pyrimidine | 0.8 |
| 110 | (1-Methyl-1H-pyrrol-2-ylmethyl)-(5-phenyl-thieno[2,3-d]pyrimidin-4-yl)-amine | 3.90 |
| 85 | (5-Phenyl-thieno[2,3-d]pyrimidin-4-yl)-thiophen-2-ylmethyl-amine | 4.21 |
| 86 | Benzyl-(5-phenyl-thieno[2,3-d]pyrimidin-4-yl)-amine | 4.36 |
| 111 | (5-Phenyl-thieno[2,3-d]pyrimidin-4-yl)-(2-pyridin-2-yl-ethyl)-amine | 4.49 |
| 112 | (5-Phenyl-thieno[2,3-d]pyrimidin-4-ylamino)-acetic acid methyl ester | 5.03 |
| 87 | Allyl-(5-phenyl-thieno[2,3-d]pyrimidin-4-yl)-amine | 5.14 |
| 113 | (2-Methoxy-ethyl)-(5-phenyl-thieno[2,3-d]-pyrimidin-4-yl)-amine | 5.27 |
| 114 | (5-Phenyl-thieno[2,3-d]pyrimidin-4-yl)-(tetrahydro-furan-2-ylmethyl)-amine | 5.18 |
| 88 | Furan-2-ylmethyl-methyl-(5-phenyl-thieno[2,3-d]pyrimidin-4-yl)-amine | 6.82 |
| 115 | Thiophen-2-ylmethyl-(5-thiophen-2-yl-thieno[2,3-d]pyrimidin-4-yl)-amine | 7.07 |
| 116 | [1,3]Dioxolan-2-ylmethyl-(5-phenyl-thieno[2,3-d]pyrimidin-4-yl)-amine | 6.16 |
| 89 | Cyclohexylmethyl-(5-phenyl-thieno[2,3-d]-pyrimidin-4-yl)-amine | 8.10 |
| 117 | 4-(Furan-2-ylmethylsulfanyl)-5-phenyl-thieno[2,3-d]pyrimidine | 9.37 |
| 118 | (5-Phenyl-thieno[2,3-d]pyrimidin-4-yl)-(2-thiophen-2-yl-ethyl)-amine | 8.56 |
| 90 | Phenethyl-(5-phenyl-thieno[2,3-d]pyrimidin-4-yl)-amine | 10.09 |
| 91 | Cyclohexyl-(5-phenyl-thieno[2,3-d]pyrimidin-4-yl)-amine | >30 |
| 119 | 4-Benzyloxy-5-phenyl-thieno[2,3-d]pyrimidine | 5.79 |
| 120 | 5-Phenyl-4-(pyridin-2-ylmethylsulfanyl)-thieno[2,3-d]pyrimidine | 12.73 |
| 121 | [5-(5-Methyl-pyridin-2-yl)-thieno[2,3-d]-pyrimidin-4-yl]-pyridin-2-ylmethyl-amine | 2.09 |
| 122 | Furan-2-ylmethyl-[5-(5-methyl-pyridin-2-yl)-thieno[2,3-d]pyrimidin-4-yl]-amine | 3.53 |
| 123 | [5-(4-Fluorophenyl)-thieno[2,3-d]pyrimidin-4-yl]-pyridin-2-ylmethyl-amine | 0.05 |
| 124 | [5-(4-Fluorophenyl)-thieno[2,3-d]pyrimidin-4-yl]-furan-2-ylmethyl-amine | 1.16 |
| 92 | Furan-2-ylmethyl-(5-thiophen-2-yl-thieno[2,3-d]pyrimidin-4-yl)-amine | 1.91 |
| 93 | (4-Nitrobenzyl)-(5-thiophen-2-yl-thieno[2,3-d]pyrimidin-4-yl)-amine | >30 |
| 94 | (5-Thiophen-2-yl-thieno[2,3-d]pyrimidin-4-yl)-(3,4,5-trimethoxy-benzyl)-amine | >30 |
| 95 | Cyclopropylmethyl-(5-thiophen-2-yl-thieno-[2,3-d]pyrimidin-4-yl)-amine | 4.51 |
| 96 | Isobutyl-(5-thiophen-2-yl-thieno[2,3-d]-pyrimidin-4-yl)-amine | 6.32 |
| 97 | Benzyl-(5-thiophen-2-yl-thieno[2,3-d]pyrimidin-4-yl)-amine | 6.53 |
| 98 | Thiophen-2-ylmethyl-(5-thiophen-2-yl-thieno[2,3-d]pyrimidin-4-yl)-amine | 6.95 |
| 99 | Allyl-(5-thiophen-2-yl-thieno [2,3-d]pyrimidin-4-yl)-amine | 7.53 |
| 100 | Furan-2-ylmethyl-methyl-(5-thiophen-2-yl-thieno[2,3-d]pyrimidin-4-yl)-amine | 9.71 |

| Example | Compound | IC$_{50}$ (μM) |
|---|---|---|
| 125 | [2-(4-Chloro-phenyl)-ethyl]-(5-methyl-thieno[2,3-d]pyrimidin-4-yl)-amine | 6.91 |
| 126 | Furan-2-ylmethyl-(5-p-tolyl-thieno[2,3-d]-pyrimidin-4-yl)-amine | 0.47 |
| 127 | [2-(3,4-Dimethoxy-phenyl)-ethyl]-(5-p-tolyl-thieno[2,3-d]pyrimidin-4-yl)-amine | 5.3 |
| 128 | 1-[2-(5-p-Tolyl-thieno[2,3-d]pyrimidin-4-ylamino)-ethyl]-imidazolidin-2-one | >30 |
| 129 | 4-(Naphthalen-2-yloxy)-5-p-tolyl-thieno-[2,3-d]pyrimidine | >30 |
| 130 | Phenethyl-(5-p-tolyl-thieno[2,3-d]pyrimidin-4-yl)-amine | 8.05 |
| 131 | 4-(5-p-Tolyl-thieno[2,3-d]pyrimidin-4-yloxy)-benzoic acid methyl ester | >30 |
| 132 | [2-(2,3-Dihydro-benzo[1,4]dioxin-6-yl)-ethyl]-[5-(3,4-dimethyl-phenyl)-thieno[2,3-d]pyrimidin-4-yl]-amine | 4.58 |
| 133 | [5-(3,4-Dimethyl-phenyl)-thieno [2,3-d]pyrimidin-4-yl]-furan-2-ylmethyl-amine | 0.67 |
| 135 | [5-(4-Chlorophenyl)-thieno[2,3-d]pyrimidin-4-yl]-furan-2-ylmethyl-amine | 0.93 |
| 136 | [5-(4-Chlorophenyl)-thieno[2,3-d]pyrimidin-4-yl]-phenethyl-amine | 16.8 |
| 137 | [5-(4-Bromophenyl)-thieno[2,3-d]pyrimidin-4-yl]-[2-(2,3-dihydro-benzo[1,4]dioxin-6-yl)-ethyl]-amine | 10.68 |
| 138 | [5-(4-Methoxy-phenyl)-thieno[2,3-d]pyrimidin-4-yl]-pyridin-2-ylmethyl-amine | 0.22 |
| 139 | Furan-2-ylmethyl-[5-(4-methoxy-phenyl)-thieno[2,3-d]pyrimidin-4-yl]-amine | 1.68 |
| 140 | (6-Ethyl-5-phenyl-thieno[2,3-d]pyrimidin-4-yl)-furan-2-ylmethyl-amine | 2.71 |
| 141 | (6-Ethyl-5-furan-3-yl-thieno[2,3-d]pyrimidin-4-yl)-furan-2-ylmethyl-amine | 2.15 |
| 142 | Pyridin-2-ylmethyl-(5-o-tolyl-thieno[2,3-d]-pyrimidin-4-yl)-amine | 1.28 |
| 143 | Furan-2-ylmethyl-(5-o-tolyl-thieno[2,3-d]-pyrimidin-4-yl)-amine | 1.32 |
| 144 | [5-(4-tert-Butyl-phenyl)-thieno[2,3-d]-pyrimidin-4-yl]-pyridin-2-ylmethyl-amine | 1.32 |
| 145 | [5-(4-tert-Butyl-phenyl)-thieno[2,3-d]-pyrimidin-4-yl]-furan-2-ylmethyl-amine | 3.05 |
| 146 | (5-Cyclohexyl-thieno[2,3-d]pyrimidin-4-yl)-pyridin-2-ylmethyl-amine | 1.68 |
| 147 | (5-Cyclohexyl-thieno[2,3-d]pyrimidin-4-yl)-furan-2-ylmethyl-amine | 2.52 |
| 148 | (2-Isopropyl-5-phenyl-thieno[2,3-d]pyrimidin-4-yl)-pyridin-2-ylmethyl-amine | 1.51 |
| 149 | (5-Phenyl-thieno[2,3-d]pyrimidin-4-yl)-(1-pyridin-2-yl-ethyl)-amine | 0.37 |
| 150 | Furan-2-ylmethyl-(2-methyl-5-phenyl-thieno[2,3-d]pyrimidin-4-yl)-amine | 0.14 |
| 151 | (5-Phenyl-2-trifluoromethyl-thieno[2,3-d]pyrimidin-4-yl)-pyridin-2-ylmethyl-amine | 1.68 |
| 181 | (2-Chloro-5-phenyl-thieno[2,3-d]pyrimidin-4-yl)-pyridin-2-ylmethyl-amine | 4.13 |
| 182 | (2-Chloro-5-phenyl-thieno[2,3-d]pyrimidin-4-yl)-furan-2-ylmethyl-amine | 1.04 |
| 188 | N$^2$-Cyclopropylmethyl-5-phenyl-N$^4$-pyridin-2-ylmethyl-thieno[2,3-d]pyrimidine-2,4-diamine | 2.52 |
| 189 | N$^2$-(2-Methoxy-ethyl)-5-phenyl-N$^4$-pyridin-2-ylmethyl-thieno[2,3-d]pyrimidine-2,4-diamine | 0.28 |
| 190 | 2-{5-Phenyl-4-[(pyridin-2-ylmethyl)-amino]-thieno[2,3-d]pyrimidin-2-ylamino}-ethanol | 0.26 |
| 191 | (2-Methoxy-5-phenyl-thieno[2,3-d]pyrimidin-4-yl)-pyridin-2-ylmethyl-amine | 0.47 |
| 192 | 5-Phenyl-N$^4$-pyridin-2-ylmethyl-thieno[2,3-d]pyrimidine-2,4-diamine | 2.18 |
| 193 | N$^2$,N$^4$-Bis-furan-2-ylmethyl-5-phenyl-thieno[2,3-d]pyrimidine-2,4-diamine | 2.5 |
| 194 | N$^4$-Furan-2-ylmethyl-5-phenyl-N$^2$-pyridin-2-ylmethyl-thieno[2,3-d]pyrimidine-2,4-diamine | 4.16 |
| 195 | (2-Benzyloxy-5-phenyl-thieno[2,3-d]pyrimidin-4-yl)-furan-2-ylmethyl-amine | 6.39 |
| 196 | N$^2$-Methyl-5-phenyl-N$^4$-pyridin-2-ylmethyl-thieno[2,3-d]pyrimidine-2,4-diamine | 0.04 |
| 197 | (2-Morpholin-4-yl-5-phenyl-thieno[2,3-d]pyrimidin-4-yl)-pyridin-2-ylmethyl-amine | 0.15 |
| 198 | N$^2$,N$^2$-Dimethyl-5-phenyl-N$^4$-pyridin-2-ylmethyl-thieno[2,3-d]pyrimidine-2,4-diamine | 0.57 |
| 152 | (2-Ethyl-5-phenyl-thieno[2,3-d]pyrimidin-4-yl)-pyridin-2-ylmethyl-amine | 0.39 |
| 153 | (2-Ethyl-5-phenyl-thieno[2,3-d]pyrimidin-4-yl)-furan-2-ylmethyl-amine | 3.63 |
| 154 | [5-(4-Fluorophenyl)-2-methyl-thieno[2,3-d]pyrimidin-4-yl]-pyridin-2-ylmethyl-amine | 1.62 |
| 157 | (6-Methyl-5-phenyl-thieno[2,3-d]pyrimidin-4-yl)-pyridin-2-ylmethyl-amine | 0.24 |
| 158 | (5-Phenyl-thieno[2,3-d]pyrimidin-4-yl)-(1,2,3,4-tetrahydro-naphthalen-1-yl)-amine | 17.70 |
| 159 | 6-Methyl-5-phenyl-4-piperidin-1-yl-thieno[2,3-d]pyrimidine | 13.36 |
| 161 | (5-Phenyl-thieno[2,3-d]pyrimidin-4-yl)-(2-thiophen-2-yl-thiazol-4-ylmethyl)-amine | 25.46 |
| 162 | (2-Phenyl-thiazol-4-ylmethyl)-(5-phenyl-thieno[2,3-d]pyrimidin-4-yl)-amine | 19.72 |
| 163 | Phenethyl-(5-thiophen-2-yl-thieno[2,3-d]-pyrimidin-4-yl)-amine | 14.32 |
| 164 | (6-Bromo-5-phenyl-thieno[2,3-d]pyrimidin-4-yl)-pyridin-2-ylmethyl-amine | 0.53 |
| 165 | (6-Bromo-5-phenyl-thieno[2,3-d]pyrimidin-4-yl)-furan-2-ylmethyl-amine | 1.6 |
| 199 | 5-Phenyl-4-[(pyridin-2-ylmethyl)-amino]-thieno[2,3-d]pyrimidine-2-carbonitrile | 6.61 |
| 200 | 5-(4-Fluorophenyl)-N$^2$,N$^2$-dimethyl-N$^4$-pyridin-2-ylmethyl-thieno[2,3-d]pyrimidine-2,4-diamine | 71.77 |
| 201 | 1-{5-(4-Fluorophenyl)-4-[(pyridin-2-ylmethyl)-amino]-thieno [2,3-d]pyrimidin-2-yl}-piperidine-4-carboxylic acid methyl ester | 15.87 |
| 202 | 3-{5-Phenyl-4-[(pyridin-2-ylmethyl)-amino]-thieno[2,3-d]pyrimidin-2-ylamino}-propionic acid ethyl ester | 2.7 |
| 203 | [2-(2-Methoxy-ethoxy)-5-phenyl-thieno[2,3-d]pyrimidin-4-yl]-pyridin-2-ylmethyl-amine | 0.48 |
| 204 | 5-(4-Fluorophenyl)-N$^2$-methyl-N$^4$-pyridin-2-ylmethyl-thieno[2,3-d]pyrimidine-2,4-diamine | 4.7 |
| 205 | 5-(4-Fluorophenyl)-N$^4$-pyridin-2-ylmethyl-thieno[2,3-d]pyrimidine-2,4-diamine | 11.87 |
| 206 | 2-(1-{5-Phenyl-4-[(pyridin-2-ylmethyl)-amino]-thieno[2,3-d]pyrimidin-2-yl}-piperidin-4-yl)-ethanol | 3.41 |
| 207 | [5-(4-Fluorophenyl)-2-morpholin-4-yl-thieno[2,3-d]pyrimidin-4-yl]-pyridin-2-ylmethyl-amine | 42.5 |
| 208 | 2-((2-Hydroxy-ethyl)-{5-phenyl-4-[(pyridin-2-ylmethyl)-amino]-thieno[2,3-d]pyrimidin-2-yl}-amino)-ethanol | 0.33 |
| 209 | 5-(4-Fluorophenyl)-N$^2$-(2-methoxy-ethyl)-N$^4$-pyridin-2-ylmethyl-thieno[2,3-d]pyrimidine-2,4-diamine | 1.83 |
| 210 | 2-{5-Phenyl-4-[(pyridin-2-ylmethyl)-amino]-thieno[2,3-d]pyrimidin-2-ylamino}-propane-1,3-diol | 0.74 |
| 211 | [2-(2-Dimethylamino-ethoxy)-5-phenyl-thieno[2,3-d]pyrimidin-4-yl]-pyridin-2-ylmethyl-amine | 5.37 |
| 212 | 2-{5-(4-Fluorophenyl)-4-[(pyridin-2-ylmethyl)-amino]-thieno[2,3-d]pyrimidin-2-ylamino}-ethanol | 7.63 |
| 237 | {5-Phenyl-4-[(pyridin-2-ylmethy)amino]thieno-[2,3-d]pyrimidin-2-yl}acetic acid ethyl ester | 0.54 |
| 238 | {4-[(Furan-2-ylmethyl)-amino]-5-phenyl-thieno-[2,3-d]pyrimidin-2-yl}-acetic acid ethyl ester | 3.33 |
| 250 | 2-{5-Phenyl-4-[(pyridin-2-ylmethypamino]-thieno[2,3-d]pyrimidin-2-yl} ethanol | 0.33 |
| 251 | 2-{4-[(Furan-2-ylmethyl)-amino]-5-phenyl-thieno[2,3-d]pyrimidin-2-yl}-ethanol | 0.08 |
| 275 | 2-{5-Phenyl-4-[(pyridin-2-ylmethyl)-amino]-thieno[2,3-d]pyrimidin-2-yl)-propane-1,3-diol | 1.53 |
| 313 | Pyridin-2-ylmethyl-[5-(4-trifluoromethyl-phenyl)-thieno[2,3-d]pyrimidin-4-yl]-amine | 2.90 |
| 314 | (5-Benzo[1,3]dioxol-5-yl-thieno[2,3-d]pyrimidin-4-yl)-pyridin-2-ylmethyl-amine | 0.01 |
| 320 | [5-(2,3-Dihydro-benzo[1,4]dioxin-6-yl)-thieno-[2,3-d]pyrimidin-4-yl]-pyridin-2-ylmethyl-amine | 0.37 |
| 321 | [5-(3-Chlorophenyl)-thieno[2,3-d]pyrimidin-4-yl]-pyridin-2-ylmethyl-amine | 1.52 |
| 322 | [5-(3-Methoxyphenyl)-thieno[2,3-d]pyrimidin-4-yl]-pyridin-2-ylmethyl-amine | 0.26 |

-continued

| Example | Compound | IC$_{50}$ (μM) |
|---|---|---|
| 323 | [5-(1H-Indol-6-yl)-thieno[2,3-d]pyrimidin-4-yl]-pyridin-2-ylmethyl-amine | 0.04 |
| 325 | [5-(4-Chlorophenyl)-thieno[2,3-d]pyrimidin-4-yl]-pyridin-2-ylmethyl-amine | 2.54 |
| 326 | [5-(2,2-Difluoro-benzo[1,3]dioxol-5-yl)-thieno[2,3-d]pyrimidin-4-yl]-pyridin-2-ylmethyl-amine | 10.43 |
| 331 | [5-(3-Fluorophenyl)-thieno[2,3-d]pyrimidin-4-yl]-pyridin-2-ylmethyl-amine | 0.03 |
| 332 | [5-(4-Morpholin-4-yl-phenyl)-thieno[2,3-d]-pyrimidin-4-yl]-pyridin-2-ylmethyl-amine | 47.43 |
| 333 | [5-(3,4-Difluorophenyl)-thieno[2,3-d]-pyrimidin-4-yl]-pyridin-2-ylmethyl-amine | 10.36 |

Example 356

Kv1.5 Autopatch Electrophysiology Method

The external bathing solution contained (in mM): 150 NaCl, 10 KCl, 100 Potassium Gluconate, 3 MgCl$_2$, 1 CaCl$_2$, 10 HEPES, pH 7.4. Patch pipettes were filled with an electrode solution of composition (in mM): 160 KCl, 0.5 MgCl$_2$, 10 HEPES, 1 EGTA, pH 7.4 with KOH.

Compounds were dissolved in DMSO (100%) and made up in the external bather at a concentration of 1 μM. All experiments were conducted at room temperature (22-24° C.).

A cell suspension (10 ml), with a density of 100,000 cells/ml, was aliquoted into a 15 ml centrifuge tube and transferred to an incubator (37° C., 5% CO$_2$) for approximately one hour before use. Following 60 min incubation, a tube was taken and centrifuged at 1000 rpm for 4 mins at room temperature. 9.5 ml supernatant was thence discarded, leaving a cell pellet at the bottom of the tube. The pellet was then resuspended using 100 μl of cold (4° C.), filtered (0.22 μm), 0.2% BSA/bather solution (0.02 g BSA/10 ml bather). The bottom of the tube was manually agitated gently until the solution became cloudy with cells. The 100 μl cell resuspension solution was then stored on the bench at 4° C. (using a Peltier-based temperature control device) until used.

A length of capillary glass (1B150E-4, WPI) was dipped into the cell suspension solution, such that ~3 cm column of fluid was taken up by capillary action. A Ag/AgCl wire was dropped into the non-dipped end of the capillary also. The outside of the solution-filled end of the capillary was then dried and the capillary was loaded into the AutoPatch™

Borosilicate glass patch pipettes (from 1.5 mm OD, thin-walled filamented, GC150-TF capillary glass, Harvard) were pulled using a DMZ pipette puller (Zeitz Instruments), and were back-filled using the internal pipette solution, being careful that no bubbles remain at the tip or in the body of the pipette. Patch pipettes typically had resistances of 2.3-3.5 MΩ. Once filled, the pipette tip and a proportion of the shaft (~15 mm) were dipped into Sigmacote (Sigma). The recording pipette was then loaded into the AutoPatch™. Automated patch-clamping was initiated by the operator, but thereafter AutoPatch.exe continued the experiment providing that pre-set conditions and criteria were satisfied.

Whole cell patch-clamp recordings were made using the AutoPatch™ rig, which incorporated an EPC9 amplifier (HEKA, Germany) under control of Pulse software (v8.54, HEKA, Germany), a motion controller with 2 translators (Newport, UK), valve controller (VF1) and a c-level suction device all at room temperature (22-24° C.). This equipment was completely under the control of AutoPatch.exe and operator intervention was only made when there was a requirement to refill the drug reservoirs or to prevent the loss of a cell due to a technical error. Cells with an R$_{series}$ greater than 18 MΩ were discounted from the experiment.

Qualification stages prior to perfusion and drug application ensured that the observed current met the criteria for the experiment. Only those cells with an I$_K$>500 pA were used for experiments. Cells were continuously perfused with external solution at a flow rate of 1.8-2 ml/minute. The perfusion chamber had a working volume of 80-85 μl and allowed for rapid exchange of drug solutions. Online analysis of the hK$_v$1.5 current during the application of compounds was performed by the AutoPatch™ software. Voltage-step protocols and analysis of data was performed as described for conventional electrophysiology.

Electrophysiology voltage-step protocols and analysis of data was performed as follows. Data was sampled at 5 kHz, and filtered with a −3 dB bandwidth of 2.5 kHz. Cells were held at a voltage of −80 mV. Currents were evoked to a voltage step for 1000 ms in duration at 0 mV every 5 s. Currents were analysed using Pulsefit software (v8.54, HEKA, Germany), with the total charge measured during the whole of the voltage step. All other plots were produced using Igor Pro (WaveMetrics).

| Example | Compound | % Inhibition at 1 μM |
|---|---|---|
| 83 | Furan-2-ylmethyl-(5-phenyl-thieno[2,3-d]-pyrimidin-4-yl)-amine | 21.9 |
| 103 | N,N-Dimethyl-2-(5-phenyl-thieno[2,3-d]-pyrimidin-4-ylamino)-acetamide | 13.6 |
| 105 | (5-Phenyl-thieno[2,3-d]pyrimidin-4-yl)-pyridin-2-ylmethyl-amine | 63.0 |
| 106 | 5-Phenyl-4-(pyridin-2-ylmethoxy)-thieno[2,3-d]pyrimidine | 21.9 |
| 84 | Cyclopropylmethyl-(5-phenyl-thieno[2,3-d]-pyrimidin-4-yl)-amine | 15.3 |
| 107 | Furan-3-ylmethyl-(5-phenyl-thieno[2,3-d]-pyrimidin-4-yl)-amine | 25.3 |
| 108 | (5-Methyl-furan-2-ylmethyl)-(5-phenyl-thieno[2,3-d]pyrimidin-4-yl)-amine | 37.2 |
| 109 | 4-(Furan-2-ylmethoxy)-5-phenyl-thieno[2,3-d]pyrimidine | 52.3 |
| 110 | (1-Methyl-1H-pyrrol-2-ylmethyl)-(5-phenyl-thieno[2,3-d]pyrimidin-4-yl)-amine | 14.2 |
| 85 | (5-Phenyl-thieno[2,3-d]pyrimidin-4-yl)-thiophen-2-ylmethyl-amine | 24.2 |
| 86 | Benzyl-(5-phenyl-thieno[2,3-d]pyrimidin-4-yl)-amine | 46.0 |
| 111 | (5-Phenyl-thieno[2,3-d]pyrimidin-4-yl)-(2-pyridin-2-yl-ethyl)-amine | 40.0 |
| 112 | (5-Phenyl-thieno[2,3-d]pyrimidin-4-ylamino)-acetic acid methyl ester | 43.5 |
| 87 | Allyl-(5-phenyl-thieno[2,3-d]pyrimidin-4-yl)-amine | 3.4 |
| 111 | (2-Methoxy-ethyl)-(5-phenyl-thieno[2,3-d]pyrimidin-4-yl)-amine | 22.2 |
| 88 | Furan-2-ylmethyl-methyl-(5-phenyl-thieno[2,3-d]pyrimidin-4-yl)-amine | 26.4 |
| 115 | Thiophen-2-ylmethyl-(5-thiophen-2-yl-thieno[2,3-d]pyrimidin-4-yl)-amine | 45.9 |
| 89 | Cyclohexylmethyl-(5-phenyl-thieno[2,3-d]pyrimidin-4-yl)-amine | 73.4 |
| 117 | 4-(Furan-2-ylmethylsulfanyl)-5-phenyl-thieno[2,3-d]pyrimidine | 43.6 |
| 118 | (5-Phenyl-thieno[2,3-d]pyrimidin-4-yl)-(2-thiophen-2-yl-ethyl)-amine | 15.8 |
| 89 | Cyclohexyl-(5-phenyl-thieno[2,3-d]pyrimidin-4-yl)-amine | 42.2 |

| Example | Compound | % Inhibition at 1 μM |
|---|---|---|
| 117 | 4-Benzyloxy-5-phenyl-thieno[2,3-d]pyrimidine | 57.2 |
| 119 | [5-(5-Methyl-pyridin-2-yl)-thieno[2,3-d]pyrimidin-4-yl]-pyridin-2-ylmethyl-amine | 44.1 |
| 120 | Furan-2-ylmethyl-[5-(5-methyl-pyridin-2-yl)-thieno[2,3-d]pyrimidin-4-yl]-amine | 25.0 |
| 121 | [5-(4-Fluorophenyl)-thieno[2,3-d]pyrimidin-4-yl]-pyridin-2-ylmethyl-amine | 82.6 |
| 122 | [5-(4-Fluorophenyl)-thieno[2,3-d]pyrimidin-4-yl]-furan-2-ylmethyl-amine | 36.3 |
| 92 | Furan-2-ylmethyl-(5-thiophen-2-yl-thieno[2,3-d]pyrimidin-4-yl)-amine | 27.6 |
| 93 | (4-Nitrobenzyl)-(5-thiophen-2-yl-thieno[2,3-d]pyrimidin-4-yl)-amine | 44.0 |
| 94 | (5-Thiophen-2-yl-thieno[2,3-d]pyrimidin-4-yl)-(3,4,5-trimethoxy-benzyl)-amine | 19.4 |
| 95 | Cyclopropylmethyl-(5-thiophen-2-yl-thieno[2,3-d]pyrimidin-4-yl)-amine | 32.6 |
| 96 | Isobutyl-(5-thiophen-2-yl-thieno[2,3-d]pyrimidin-4-yl)-amine | 22.9 |
| 97 | Benzyl-(5-thiophen-2-yl-thieno[2,3-d]pyrimidin-4-yl)-amine | 43.3 |
| 98 | Thiophen-2-ylmethyl-(5-thiophen-2-yl-thieno[2,3-d]pyrimidin-4-yl)-amine | 21.0 |
| 99 | Allyl-(5-thiophen-2-yl-thieno[2,3-d]-pyrimidin-4-yl)-amine | 17.5 |
| 100 | Furan-2-ylmethyl-methyl-(5-thiophen-2-yl-thieno[2,3-d]pyrimidin-4-yl)-amine | 19.9 |
| 126 | Furan-2-ylmethyl-(5-p-tolyl-thieno[2,3-d]-pyrimidin-4-yl)-amine | 83.4 |
| 127 | [2-(3,4-Dimethoxyphenyl)-ethyl]-(5-p-tolyl-thieno[2,3-d]pyrimidin-4-yl)-amine | 20.7 |
| 128 | 1-[2-(5-p-Tolyl-thieno[2,3-d]pyrimidin-4-ylamino)-ethyl]-imidazolidin-2-one | 25.0 |
| 129 | 4-(Naphthalen-2-yloxy)-5-p-tolyl-thieno[2,3-d]pyrimidine | 47.4 |
| 131 | 4-(5-p-Tolyl-thieno[2,3-d]pyrimidin-4-yloxy)-benzoic acid methyl ester | 29.8 |
| 132 | [2-(2,3-Dihydro-benzo[1,4]dioxin-6-yl)-ethyl]-[5-(3,4-dimethyl-phenyl)-thieno[2,3-d]pyrimidin-4-yl]-amine | 92.0 |
| 133 | [5-(3,4-Dimethyl-phenyl)-thieno[2,3-d]pyrimidin-4-yl]-furan-2-ylmethyl-amine | 77.0 |
| 135 | [5-(4-Chlorophenyl)-thieno[2,3-d]pyrimidin-4-yl]-furan-2-ylmethyl-amine | 84.8 |
| 136 | [5-(4-Chlorophenyl)-thieno[2,3-d]pyrimidin-4-yl]-phenethyl-amine | 27.2 |
| 137 | [5-(4-Bromophenyl)-thieno[2,3-d]pyrimidin-4-yl]-[2-(2,3-dihydro-benzo[1,4]dioxin-6-yl)-ethyl]-amine | 96.0 |
| 138 | [5-(4-Methoxyphenyl)-thieno[2,3-d]pyrimidin-4-yl]-pyridin-2-ylmethyl-amine | 92.6 |
| 139 | Furan-2-ylmethyl-[5-(4-methoxy-phenyl)-thieno[2,3-d]pyrimidin-4-yl]-amine | 46.9 |
| 140 | (6-Ethyl-5-phenyl-thieno[2,3-d]pyrimidin-4-yl)-furan-2-ylmethyl-amine | 74.2 |
| 141 | (6-Ethyl-5-furan-3-yl-thieno[2,3-d]pyrimidin-4-yl)-furan-2-ylmethyl-amine | 81.3 |
| 142 | Pyridin-2-ylmethyl-(5-o-tolyl-thieno[2,3-d]pyrimidin-4-yl)-amine | 49.7 |
| 143 | Furan-2-ylmethyl-(5-o-tolyl-thieno[2,3-d]-pyrimidin-4-yl)-amine | 63.0 |
| 144 | [5-(4-tert-Butyl-phenyl)-thieno[2,3-d]pyrimidin-4-yl]-pyridin-2-ylmethyl-amine | 81.0 |
| 145 | [5-(4-tert-Butyl-phenyl)-thieno[2,3-d]pyrimidin-4-yl]-furan-2-ylmethyl-amine | 68.0 |
| 146 | (5-Cyclohexyl-thieno[2,3-d]pyrimidin-4-yl)-pyridin-2-ylmethyl-amine | 81.0 |
| 147 | (5-Cyclohexyl-thieno[2,3-d]pyrimidin-4-yl)-furan-2-ylmethyl-amine | 71.0 |
| 148 | (2-Isopropyl-5-phenyl-thieno[2,3-d]pyrimidin-4-yl)-pyridin-2-ylmethyl-amine | 88.0 |
| 149 | (5-Phenyl-thieno[2,3-d]pyrimidin-4-yl)-(1-pyridin-2-yl-ethyl)-amine | 78.0 |
| 150 | Furan-2-ylmethyl-(2-methyl-5-phenyl-thieno[2,3-d]pyrimidin-4-yl)-amine | 96.8 |
| 151 | (5-Phenyl-2-trifluoromethyl-thieno[2,3-d]pyrimidin-4-yl)-pyridin-2-ylmethyl-amine | 95.0 |
| 181 | (2-Chloro-5-phenyl-thieno[2,3-d]pyrimidin-4-yl)-pyridin-2-ylmethyl-amine | 96.0 |
| 182 | (2-Chloro-5-phenyl-thieno[2,3-d]pyrimidin-4-yl)-furan-2-ylmethyl-amine | 75.8 |
| 188 | $N^2$-Cyclopropylmethyl-5-phenyl-$N^4$-pyridin-2-ylmethyl-thieno[2,3-d]pyrimidine-2,4-diamine | 98.0 |
| 189 | $N^2$-(2-Methoxy-ethyl)-5-phenyl-$N^4$-pyridin-2-ylmethyl-thieno[2,3-d]pyrimidine-2,4-diamine | 97.4 |
| 190 | 2-{5-Phenyl-4-[(pyridin-2-ylmethyl)-amino]-thieno[2,3-d]pyrimidin-2-ylamino}-ethanol | 97.1 |
| 191 | (2-Methoxy-5-phenyl-thieno[2,3-d]pyrimidin-4-yl)-pyridin-2-ylmethyl-amine | 91.8 |
| 192 | 5-Phenyl-$N^4$-pyridin-2-ylmethyl-thieno[2,3-d]-pyrimidine-2,4-diamine | 90.0 |
| 193 | $N^2,N^4$-Bis-furan-2-ylmethyl-5-phenyl-thieno[2,3-d]pyrimidine-2,4-diamine | 89.2 |
| 194 | $N^4$-Furan-2-ylmethyl-5-phenyl-$N^2$-pyridin-2-ylmethyl-thieno[2,3-d]pyrimidine-2,4-diamine | 81.0 |
| 195 | (2-Benzyloxy-5-phenyl-thieno[2,3-d]pyrimidin-4-yl)-furan-2-ylmethyl-amine | 90.0 |
| 196 | $N^2$-Methyl-5-phenyl-$N^4$-pyridin-2-ylmethyl-thieno[2,3-d]pyrimidine-2,4-diamine | 97.0 |
| 197 | (2-Morpholin-4-yl-5-phenyl-thieno[2,3-d]-pyrimidin-4-yl)-pyridin-2-ylmethyl-amine | 98.0 |
| 198 | $N^2,N^2$-Dimethyl-5-phenyl-$N^4$-pyridin-2-ylmethyl-thieno[2,3-d]pyrimidine-2,4-diamine | 98.1 |
| 152 | (2-Ethyl-5-phenyl-thieno[2,3-d]pyrimidin-4-yl)-pyridin-2-ylmethyl-amine | 98.7 |
| 153 | (2-Ethyl-5-phenyl-thieno[2,3-d]pyrimidin-4-yl)-furan-2-ylmethyl-amine | 96.8 |
| 154 | (6-Methylpyridin-2-ylmethyl)-(5-phenyl-thieno[2,3-d]pyrimidin-4-yl)-amine | 93.0 |
| 155 | [5-(4-Fluorophenyl)-2-methyl-thieno[2,3-d]-pyrimidin-4-yl]-pyridin-2-ylmethyl-amine | 92.2 |
| 156 | (6-Methyl-pyridin-2-ylmethyl)-(5-phenyl-thieno[2,3-d]pyrimidin-4-yl)-amine | 92.0 |
| 157 | (6-Methyl-5-phenyl-thieno[2,3-d]pyrimidin-4-yl)-pyridin-2-ylmethyl-amine | 88.0 |
| 158 | (5-Phenyl-thieno[2,3-d]pyrimidin-4-yl)-(1,2,3,4-tetrahydro-naphthalen-1-yl)-amine | 83.4 |
| 159 | 6-Methyl-5-phenyl-4-piperidin-1-yl-thieno[2,3-d]pyrimidine | 83.0 |
| 160 | 2-[(5-Phenyl-thieno[2,3-d]pyrimidin-4-ylamino)-methyl]-nicotinic acid ethyl ester | 80.0 |
| 161 | (5-Phenyl-thieno[2,3-d]pyrimidin-4-yl)-(2-thiophen-2-yl-thiazol-4-ylmethyl)-amine | 79.4 |
| 162 | (2-Phenyl-thiazol-4-ylmethyl)-(5-phenyl-thieno[2,3-d]pyrimidin-4-yl)-amine | 74.5 |
| 163 | Phenethyl-(5-thiophen-2-yl-thieno[2,3-d]pyrimidin-4-yl)-amine | 70.8 |
| 164 | (6-Bromo-5-phenyl-thieno[2,3-d]pyrimidin-4-yl)-pyridin-2-ylmethyl-amine | 92.8 |
| 165 | (6-Bromo-5-phenyl-thieno[2,3-d]pyrimidin-4-yl)-furan-2-ylmethyl-amine | 91.0 |
| 199 | 5-Phenyl-4-[(pyridin-2-ylmethyl)-amino]-thieno[2,3-d]pyrimidine-2-carbonitrile | 99.5 |
| 200 | 5-(4-Fluorophenyl)-$N^2,N^2$-dimethyl-$N^4$-pyridin-2-ylmethyl-thieno[2,3-d]pyrimidine-2,4-diamine | 99.3 |
| 201 | 1-{5-(4-Fluorophenyl)-4-[(pyridin-2-ylmethyl)-amino]-thieno[2,3-d]pyrimidin-2-yl}-piperidine-4-carboxylicacid methyl ester | 98.2 |
| 202 | 3-{5-Phenyl-4-[(pyridin-2-ylmethyl)-amino]-thieno[2,3-d]pyrimidin-2-ylamino}-propionic acid ethyl ester | 98.0 |
| 203 | [2-(2-Methoxy-ethoxy)-5-phenyl-thieno[2,3-d]-pyrimidin-4-yl]-pyridin-2-ylmethyl-amine | 98.0 |
| 204 | 5-(4-Fluorophenyl)-$N^2$-methyl-$N^4$-pyridin-2-ylmethyl-thieno[2,3-d]pyrimidine-2,4-diamine | 97.9 |
| 205 | 5-(4-Fluorophenyl)-$N^4$-pyridin-2-ylmethyl-thieno[2,3-d]pyrimidine-2,4-diamine | 97.5 |
| 206 | 2-(1-{5-Phenyl-4-[(pyridin-2-ylmethyl)-amino]-thieno[2,3-d]pyrimidin-2-yl}-piperidin-4-yl)-ethanol | 97.5 |
| 207 | [5-(4-Fluorophenyl)-2-morpholin-4-yl-thieno[2,3-d]pyrimidin-4-yl]-pyridin-2-ylmethyl-amine | 97.2 |

-continued

| Example | Compound | % Inhibition at 1 μM |
|---|---|---|
| 208 | 2-((2-Hydroxy-ethyl)-{5-phenyl-4-[(pyridin-2-ylmethyl)-amino]-thieno[2,3-d]pyrimidin-2-yl}-amino)-ethanol | 96.6 |
| 209 | 5-(4-Fluorophenyl)-N²-(2-methoxy-ethyl)-N⁴-pyridin-2-ylmethyl-thieno[2,3-d]pyrimidine-2,4-diamine | 96.0 |
| 210 | 2-{5-Phenyl-4-[(pyridin-2-ylmethyl)-amino]-thieno[2,3-d]pyrimidin-2-ylamino}-propane-1,3-diol | 95.6 |
| 211 | [2-(2-Dimethylamino-ethoxy)-5-phenyl-thieno[2,3-d]pyrimidin-4-yl]-pyridin-2-ylmethyl-amine | 89.0 |
| 212 | 2-{5-(4-Fluorophenyl)-4-[(pyridin-2-ylmethyl)-amino]-thieno[2,3-d]pyrimidin-2-ylamino}-ethanol | 87.0 |
| 214 | 3-{5-Phenyl-4-[(pyridin-2-ylmethyl)-amino]-thieno[2,3-d]pyrimidin-2-ylamino}-propane-1,2-diol | 87.0 |
| 215 | [2-(4-Methyl-piperazin-1-yl)-5-phenyl-thieno[2,3-d]pyrimidin-4-yl]-pyridin-2-ylmethyl-amine | 82.0 |
| 237 | {5-Phenyl-4-[(pyridin-2-ylmethyl)amino]thieno-[2,3-d]pyrimidin-2-yl}acetic acid ethyl ester | 95.0 |
| 238 | {4-[(Furan-2-ylmethyl)-amino]-5-phenyl-thieno[2,3-d]pyrimidin-2-yl)-acetic acid ethyl ester | 96.0 |
| 250 | 2-{5-Phenyl-4-[(p yridin-2-ylmethy)amino]-thieno[2,3-d]pyrimidin-2-yl}ethanol | 98.0 |
| 251 | 2-{4-[(Furan-2-ylmethyp-amino]-5-phenyl-thieno[2,3-d]pyrimidin-2-yl}-ethanol | 98.0 |
| 275 | 2-{5-Phenyl-4-[(pyridin-2-ylmethyl)-amino]-thieno[2,3-d]pyrimidin-2-yl)-propane-1,3-diol | 93.0 |
| 287 | N-Methyl-2-{5-phenyl-4-[{pyridin-2-ylmethyl)amino]thieno[2,3-d]pyrimidin-2-y} acetamide | 91.0 |
| 302 | (2-Dimethylaminomethyl-5-phenylthieno-[2,3-d]pyrimidin-4-yl)pyridin-2-ylmethylamine | 76.0 |
| 303 | (2-Morpholin-4-ylmethyl-5-phenyl-thieno-[2,3-d]pyrimidin-4-yl)-pyridin-2-ylmethyl-amine | 63.0 |
| 304 | (2-Methylaminomethyl-5-phenyl-thieno-[2,3-d]pyrimidin-4-yl)-pyridin-2-ylmethyl-amine | 58.0 |
| 305 | (2-Methoxymethyl-5-phenylthien[2,3-d]primidin-4-yl)pyridin-2-ylmethylamine | 94.0 |
| 313 | Pyridin-2-ylmethyl-[5-(4-trifluoromethyl-phenyl)-thieno[2,3-d]pyrimidin-4-yl]-amine | 98.3 |
| 314 | (5-Benzo[1,3]dioxol-5-yl-thieno[2,3-d]pyrimidin-4-yl)-pyridin-2-ylmethyl-amine | 97.3 |
| 315 | [5-(4-Dimethylamino-phenyl)-thieno-[2,3-d]pyrimidin-4-yl]-pyridin-2-ylmethyl-amine | 98.0 |
| 316 | [5-(3,4-Dimethyl-phenyl)-thieno[2,3-d]pyrimidin-4-yl]-pyridin-2-ylmethyl-amine | 98.0 |
| 317 | Pyridin-2-ylmethyl-[5-(4-trifluoromethoxy-phenyl)-thieno[2,3-d]pyrimidin-4-yl]-amine | 98.0 |
| 318 | Pyridin-2-ylmethyl-(5-p-tolyl-thieno-[2,3-d]pyrimidin-4-yl)-amine | 98.0 |
| 319 | (5-Benzo[1,3]dioxol-5-yl-thieno[2,3-d]pyrimidin-4-yl)-pyridin-2-ylmethyl-amine | 97.3 |
| 320 | [5-(2,3-Dihydro-benzo[1,4]dioxin-6-yl)-thieno[2,3-d]pyrimidin-4-yl]-pyridin-2-ylmethyl-amine | 97.0 |
| 321 | [5-(3-Chlorophenyl)-thieno[2,3-d]pyrimidin-4-yl]-pyridin-2-ylmethyl-amine | 95.0 |
| 322 | [5-(3-Methoxyphenyl)-thieno[2,3-d]pyrimidin-4-yl]-pyridin-2-ylmethyl-amine | 94.0 |
| 323 | [5-(1H-Indol-6-yl)-thieno[2,3-d]pyrimidin-4-yl]-pyridin-2-ylmethyl-amine | 94.0 |
| 324 | [5-(4-Methoxymethoxy-phenyl)-thieno[2,3-d]-pyrimidin-4-yl]-pyridin-2-ylmethyl-amine | 93.0 |
| 325 | [5-(4-Chlorophenyl)-thieno[2,3-d]pyrimidin-4-yl]-pyridin-2-ylmethyl-amine | 90.8 |
| 326 | [5-(2,2-Difluoro-benzo[1,3]dioxol-5-yl)-thieno[2,3-d]pyrimidin-4-yl]-pyridin-2-ylmethyl-amine | 89.0 |
| 327 | 4-{4-[(Pyridin-2-ylmethyl)-amino]-thieno[2,3-d]-pyrimidin-5-yl}-benzoic acid methyl ester | 83.0 |
| 328 | [5-(6-Methoxy-pyridin-3-yl)-thieno[2,3-d]pyrimidin-4-yl]-pyridin-2-ylmethyl-amine | 83.0 |
| 329 | [5-(2,4-Dichlorophenyl)-thieno[2,3-d]pyrimidin-4-yl]-pyridin-2-ylmethyl-amine | 81.0 |
| 330 | [5-(4-Chloro-3-trifluoromethyl-phenyl)-thieno-[2,3-d]pyrimidin-4-yl]-pyridin-2-ylmethyl-amine | 79.0 |
| 331 | [5-(3-Fluorophenyl)-thieno[2,3-d]pyrimidin-4-yl]-pyridin-2-ylmethyl-amine | 76.0 |
| 332 | [5-(4-Morpholin-4-yl-phenyl)-thieno[2,3-d]pyrimidin-4-yl]-pyridin-2-ylmethyl-amine | 73.0 |
| 333 | [5-(3,4-Difluoro-phenyl)-thieno[2,3-d]pyrimidin-4-yl]-pyridin-2-ylmethyl-amine | 63.0 |
| 166 | 6-Methyl-N-[(6-methylpyridin-2-yl)methyl]-5-phenylthieno[2,3-d]pyrimidin-4-amine | 97 |
| 167 | 6-Bromo-N-[(6-methylpyridin-2-yl)methyl]-5-phenylthieno[2,3-d]pyrimidin-4-amine | 99 |

ABBREVIATIONS

| | |
|---|---|
| Kv$_{(ur)}$ | Cardiac Ultrarapid Delayed Rectifier |
| CHO | Chinese Hamster Ovary Cells |
| DMEM | Dulbecco's Modified Eagle media |
| FCS | Fetal Calf Serum |
| EBSS | Earls Balanced Salt Solution |
| WCPC | Whole-Cell Patch-Clamp |

REFERENCES

Herbert, "General principles of the structure of ion channels", Am. J. Med, 104, 87-98, 1998.

Armstrong & Hille, "Voltage-gated ion channels and electrical excitability", Neuron, 20, 371-380, 1998.

Gutman G A, Chandy K G, Adelman J P, Aiyar J, Bayliss D A, Clapham D E, Covarriubias M, Desir G V, Furuichi K, Ganetzky B, Garcia M L, Grissmer S, Jan L Y, Karschin A, Kim D, Kuperschmidt S, Kurachi Y, Lazdunski M, Lesage F, Lester H A, McKinnon D, Nichols C G, O'Kelly I, Robbins J, Robertson G A, Rudy B, Sanguinetti M, Seino S, Stuehmer W, Tamkun M M, Vandenberg C A, Wei A, Wulff H, Wymore R S International Union of Pharmacology. XLI. Compendium of voltage-gated ion channels: potassium channels. Pharmacol Rev. 2003 December; 55(4):583-6.

Shieh et al. "Potassium channels: molecular defects, diseases, and therapeutic opportunities", Pharmacol Rev, 52(4), 557-594, 2000.

Ford et al. "Potassium Channels: Gene Family, Therapeutic Relevance, High-Throughput Screening Technologies and Drug Discovery", Prog Drug Res, 58, 133-168, 2002.

Marban "Cardiac channelopalthies", Nature, 415, 213-218, 213-218, 2002.

Brendel and Peukert 'Blockers of the Kv1.5 Channel for the Treatment of Atrial Arrhythmias', Expert Opinion in Therapeutic Patents, 12 (11), 1589-1598 (2002).

Wang et al., "Sustained depolarization-induced outward current in human atrial myocytes. Evidence for a novel delayed rectifier K+ current similar to Kv1.5 cloned channel currents", Circ Res, 73, 1061-1076, 1993.

Fedida et al., "Identity of a novel delayed rectifier current from human heart with a cloned K+ channel current", Circ Res, 73, 210-216, 1993.

Feng et al., "Antisense oligodeoxynucleotides directed against Kv1.5 mRNA specifically inhibit ultrarapid delayed rectifier K+ current in cultured adult human atrial myocytes", Circ Res, 80, 572-579, 1997.

Amos et al., "Differences between outward currents of human atrial and subepicardial ventricular myocytes", J Physiol, 491, 31-50, 1996.

Li et al., "Evidence for two components of delayed rectifier K+ current in human ventricular myocytes", Circ Res, 78, 689-696, 1996.

Nattel, 'Therapeutic implications of atrial fibrillation mechanisms: can mechanistic insights be used to improve AF management?' Cardiovascular Research, Volume 54, Issue 2, 347-360, 2002.

Courtemanche et al., "Ionic targets for drug therapy and atrial fibrillation-induced electrical remodeling: insights from a mathematical model", Cardiovasc Res, 42(2), 477-489, 1999.

Nattel et al., "Cardiac ultrarapid delayed rectifiers: a novel potassium current family of functional similarity and molecular diversity", Cell Physiol Biochem, 9(4-5), 217-226, 1999.

Knobloch K, Brendel J, Peukert S, Rosenstein B, Busch A E, Wirth K J. Electrophysiological and antiarrhythmic effects of the novel I(Kur) channel blockers, S9947 and S20951, on left vs. right pig atrium in vivo in comparison with the I(Kr) blockers dofetilide, azimilide, d,l-sotalol and ibutilide. Naunyn Schmiedebergs Arch Pharmacol. 2002 November; 366(5):482-7.

Wirth K J, Paehler T, Rosenstein B, Knobloch K, Maier T, Frenzel J, Brendel J, Busch A E, Bleich M. Atrial effects of the novel K(+)-channel-blocker AVE0118 in anesthetized pigs. Cardiovasc Res. November 1; 60(2):298-306, 2003.

Colatsky et al., "Channel specificity in antiarrhythmic drug action. Mechanism of potassium channel block and its role in suppressing and aggravating cardiac arrhythmias", Circulation, 82(6), 2235-2242, 1990.

Feng et al., "Effects of class III antiarrhythmic drugs on transient outward and ultra-rapid delayed rectifier currents in human atrial myocytes", J Pharmacol Exp Ther, 281(1), 384-392, 1997.

Wang et al., "Effects of flecamide, quinidine, and 4-aminopyridine on transient outward and ultrarapid delayed rectifier currents in human atrial myocytes", J Pharmacol, 272(1), 184-196, 1995.

Malayev et al., "Mechanism of clofilium block of the human Kv1.5 delayed rectifier potassium channel", Mol Pharmaco, 147(1), 198-205, 1995.

Godreau et al., "Mechanisms of action of antiarrhythmic agent bertosamil on hKv1.5 channels and outward potassium current in human atrial myocytes", J Pharmacol Exp Ther 300(2), 612-620, 2002.

Matsuda et al., "Inhibition by a novel anti-arrhythmic agent, NIP-142, of cloned human cardiac K+ channel Kv1.5 current", Life Sci, 68, 2017-2024, 2001.

Bachmann et al., "Characterization of a novel Kv1.5 channel blocker in *Xenopus oocytes*, CHO cells, human and rat cardiomyocytes", Naunyn Schmiedebergs Arch Pharmacol, 364(5), 472-478, 2001.

Peukert S, Brendel J, Pirard B, Bruggemann A, Below P, Kleemann H W, Hemmerle H, Schmidt W. Identification, synthesis, and activity of novel blockers of the voltage-gated potassium channel Kv1.5. J Med. Chem. February 13; 46(4):486-98, 2003.

Xu & Xu, "The expression of arrhythmic related genes in *Xenopus oocytes* for evaluation of class III antiarrhythmic drugs from ocean active material", Yi Chuan Xue Bao, 27(3), 195-201, 2000.

Katada et al, 'Cytotoxic effects of NSL-1406, a new thienopyrimidine derivative, on leukocytes and osteoclasts.' Bioorg. Med. Chem. Lett., 9, 797-802, 1999.

Stewart et al, 'Discovery of inhibitors of cell adhesion molecule expression in human endothelial cells. 1. Selective inhibition of ICAM-1 and E-selectin expression', J. Med. Chem., 44, 988-1002, 2001.

Hozien et al, 'Synthesis and application of some new thienopyrimidine derivatives as antimicrobial agents', Synthetic Communications, 26(20), 3733-3755, 1996.

Ismail et al., 'Synthesis and antimicrobial activity of some tetramethylenethienopyrimidine derivatives', Farmaco, 50(9), 611-616, 1995.

Konno et al., 'Synthesis of thienopyrimidine derivatives and their antifungal activities', Yakugaku Zasshi, 109(7), 464-473, 1989.

Ram et al., 'Thienopyrimidines as potential chemotherapeutic agents II', J. Het. Chem., 18(7), 1277-1280, 1981.

Ram et al., 'Thienopyrimidines as potential chemotherapeutic agents', Archiv der Pharmazie, 312(1), 19-25, 1979.

Shehata et al., 'Synthesis, antitumour and anti-HIV-1 testing of certain thienopyrimidine, thienoimidazopyrimidine and thienothiazine derivatives' Med. Chem. Res., 6(3), 148-163, 1996.

Moneer et al, 'Reaction of 30-amino and 4-hydrazino-5,6-tetramethylenethienopyrimidine derivatives with azlactones', Egyptian Journal of Pharm. Sci., 34 (4-6), 599-609, 1994.

Jordis et al., '7,9-Dideaza-9-thiaadenines (4-aminothieno[2,3-d]pyrimidines) as potential anticytokinins' Vestnik Slovenskega Kemijskega Drustva, 33(3), 217-38, 1986.

Noravyan et al., 'Synthesis and anticonvulsive activity of 4-alkyl (or aryl)amino-6,6-dimethyl-5,6-dihydro-8H-pyrano (or thiopyrano)[3,4-b]thieno[5,4-d]pyrimidines' Khimiko-Farmatsevticheskii Zhurnal, 11(9), 38-42, 1977.

Hosni et al., 'Thienopyrimidines II: synthesis of newer thieno [2,3-d]pyrimidines and their quaternized derivatives with molluscicidal activity' Acta Poloniae Pharmaceutica, 56(1) 49-56, 1999.

Munchof et al., 'Design and SAR of thienopyrimidine and thienopyridine inhibitors of VEGFR-2 kinase activity'. Bioorganic & Medicinal Chemistry Letters, 14(1), 21-24, 2004

What is claimed is:

1. A compound of formula (I)

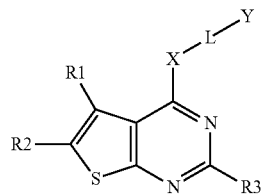

wherein

R1 is aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, C(O)NR9R10, NHC(O)R8, $SO_2NR9R10$, and hydroxyl; hetero aryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; or cycloalkyl;

R2 is H; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, $C(O)NR9R10$, $NHC(O)R8$, and $SO_2NR9R10$; nitro; $CO_2R7$; $CONR4R5$ or halo;

R3 is H; NR4R5; NHC(O)R8; halo; trifluoromethyl; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, $C(O)NR9R10$, $NHC(O)R8$, and $SO_2NR9R10$; cyano or alkoxy;

R4 and R5 may be the same or different, and may be H; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, $C(O)NR9R10$, $NHC(O)R8$, and $SO_2NR9R10$; aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, $C(O)NR9R10$, $NHC(O)R8$, $SO_2NR9R10$, and hydroxyl; heteroaryl, which is unsubstituted or substituted at any position with a substituent selected from the group consisting of cyano, nitro, halogen, alkyl, alkylthio, alkoxy, NR9R10, $CO_2R7$, $C(O)NR9R10$, $NHC(O)R8$, $SO_2NR9R10$, and hydroxyl; or cycloalkyl; or R4 and R5 may together form a saturated, unsaturated or partially saturated 4 to 7 member ring, wherein said ring may optionally comprise one or more further heteroatoms selected from N, O or S;

X is O, S or NR6;

R6 is H or alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, $C(O)NR9R10$, $NHC(O)R8$, and $SO_2NR9R10$;

R7 is hydrogen, methyl or ethyl;

R8 is methyl or ethyl;

R9 and R10 are independently selected from the group consisting of hydrogen, unsubstituted alkyl, unsubstituted aryl, unsubstituted heteroaryl, unsubstituted cycloalkyl, aminoethyl, methylaminoethyl, hydroxyethyl, and alkoxyethyl; or R9 and R10 taken together form a saturated, unsaturated, or partially saturated 4 to 7 membered ring;

L is $(CH_2)_n$, where n is 1, 2 or 3; and

Y is heterocyclic group, which is unsubstituted or substituted at any position with a substituent selected from the group consisting of cyano, nitro, halogen, alkyl, alkylthio, alkoxy, NR9R10, $CO_2R7$, $C(O)NR9R10$, $NHC(O)R8$, $SO_2NR9R10$, and hydroxyl; alkenyl or cycloalkyl;

or a pharmaceutically acceptable salt thereof;

with the proviso that when Y is furanyl; tetrahydrofuranyl; pyrimidinyl; pyrrolidinyl or 1,3-benzodioxolyl, then R1 is not phenyl, phenyl monosubstituted by halogen or phenyl substituted by methyl; and wherein the compound is not:

5-Phenyl-N-(pyridin-2-ylmethyl)thieno[2,3-d]pyrimidin-4-amine;
5-(4-Chlorophenyl)-N-[3-(1H-imidazol-1-yl)propyl]thieno[2,3-d]pyrimidin-4-amine;
5-(4-Chlorophenyl)-N-(pyridin-2-ylmethyl)thieno[2,3-d]pyrimidin-4-amine;
5-(4-Chlorophenyl)-N-(pyridin-3-ylmethyl)thieno[2,3-d]pyrimidin-4-amine;
5-(4-Fluorophenyl)-N-(pyridin-3-ylmethyl)thieno[2,3-d]pyrimidin-4-amine;
N-Allyl-5-phenylthieno[2,3-d]pyrimidin-4-amine;
5-(4-Methylphenyl)-N-(2-thien-2-ylethyl)thieno[2,3-d]pyrimidin-4-amine;
5-(4-Chlorophenyl)-N-(2-thien-2-ylethyl)thieno[2,3-d]pyrimidin-4-amine;
5-(4-Fluorophenyl)-N-(2-thien-2-ylethyl)thieno[2,3-d]pyrimidin-4-amine;
N-Allyl-5-(4-chlorophenyl)thieno[2,3-d]pyrimidin-4-amine;
5-(4-Bromophenyl)-N-(pyridin-3-ylmethyl)thieno[2,3-d]pyrimidin-4-amine;
N-[3-(1H-Imidazol-1-yl)propyl]-5-phenylthieno[2,3-d]pyrimidin-4-amine; or
1-(2-{[5-(4-Methylphenyl)thieno[2,3-d]pyrimidin-4-yl]amino}ethyl)imidazolidin-2-one.

2. A compound as claimed in claim 1 wherein R1 is aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, $C(O)NR9R10$, $NHC(O)R8$, $SO_2NR9R10$, and hydroxyl; or heteroaryl, which is unsubstituted or substituted at any position with a substituent selected from the group consisting of cyano, nitro, halogen, alkyl, alkylthio, alkoxy, NR9R10, $CO_2R7$, $C(O)NR9R10$, $NHC(O)R8$, $SO_2NR9R10$, and hydroxyl; R2 is H or alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, $C(O)NR9R10$, $NHC(O)R8$, and $SO_2NR9R10$; R3 is H; NR4R5; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, $C(O)NR9R10$, $NHC(O)R8$, and $SO_2NR9R10$; or alkoxy X is O or NR6, R6 is H, n is 1 or 2 and Y is cycloalkyl, or heteroaryl, which is unsubstituted or substituted at any position with a substituent selected from the group consisting of cyano, nitro, halogen, alkyl, alkylthio, alkoxy, NR9R10, $CO_2R7$, $C(O)NR9R10$, $NHC(O)R8$, $SO_2NR9R10$, and hydroxyl.

3. A compound as claimed in claim 2 wherein X is NR6, n is 1 and Y is heteroaryl, which is unsubstituted or substituted at any position with a substituent selected from the group consisting of cyano, nitro, halogen, alkyl, alkylthio, alkoxy, NR9R10, $CO_2R7$, $C(O)NR9R10$, $NHC(O)R8$, $SO_2NR9R10$, and hydroxyl.

4. A compound as claimed in any one of claims 1 to 3 wherein Y is furanyl, thienyl or pyridyl.

5. A compound as claimed in any one of claims 1 to 3 wherein Y is optionally substituted furan-2-yl or optionally substituted pyridin-2-yl.

6. A compound which is:
2-{5-Phenyl-4-[(pyridin-2-ylmethyl)-amino]-thieno[2,3-d]pyrimidin-2-yl}-propane-1,3-diol;
2-{5-(4-Fluorophenyl)-4-[(pyridin-2-ylmethyl)-amino]thieno[2,3-d]pyrimidin-2-ylamino}-ethanol;
Pyridin-2-ylmethyl-(5-p-tolyl-thieno[2,3-d]pyrimidin-4-yl)-amine;
2-{5-Phenyl-4-[(pyridin-2-ylmethyl)-amino]-thieno[2,3-d]pyrimidin-2-ylamino}-ethanol;
2-{5-Phenyl-4-[(pyridin-2-ylmethyl)amino]thieno[2,3-d]pyrimidin-2-yl}ethanol;
2-((2-Hydroxy-ethyl)-{5-phenyl-4-[(pyridin-2-ylmethyl)-amino]-thieno[2,3-d]pyrimidin-2-yl}-amino)-ethanol;

2-Methyl-N-(2-pyridyl)methyl-5-phenylthieno[2,3-d]pyrimidin-4-ylamine;
2-{4-[(Furan-2-ylmethyl)-amino]-5-phenyl-thieno[2,3-d]pyrimidin-2-yl}-ethanol;
[2-(2-Methoxy-ethoxy)-5-phenyl-thieno[2,3-d]pyrimidin-4-yl]-pyridin-2-ylmethylamine;
(2-Methoxy-5-phenyl-thieno[2,3-d]pyrimidin-4-yl)-pyridin-2-ylmethyl-amine;
5-(4-Fluorophenyl)-$N^2$-(2-methoxy-ethyl)-$N^4$-pyridin-2-ylmethyl-thieno[2,3-d]pyrimidine-2,4-diamine;
[5-(4-Dimethylamino-phenyl)-thieno[2,3-d]pyrimidin-4-yl]-pyridin-2-ylmethyl-amine;
5-(4-Fluorophenyl)-$N^2$,$N^2$-dimethyl-$N^4$-pyridin-2-ylmethyl-thieno[2,3-d]pyrimidine-2,4-diamine;
Pyridin-2-ylmethyl-[5-(4-trifluoromethyl-phenyl)-thieno[2,3-d]pyrimidin-4-yl]-amine;
[5-(1H-Indol-6-yl)-thieno[2,3-d]pyrimidin-4-yl]-pyridin-2-ylmethyl-amine;
(5-Benzo[1,3]dioxol-5-yl-thieno[2,3-d]pyrimidin-4-yl)-pyridin-2-ylmethyl-amine;
2-{5-Phenyl-4-[(pyridin-2-ylmethyl)-amino]-thieno[2,3-d]pyrimidin-2-ylamino}-propane-1,3-diol;
3-{5-Phenyl-4-[(pyridin-2-ylmethyl)-amino]-thieno[2,3-d]pyrimidin-2-ylamino}-propane-1,2-diol;
N-Methyl-2-{5-phenyl-4-[(pyridin-2-ylmethyl)amino]thieno[2,3-d]pyrimidin-2-yl}acetamide; or
6-Methyl-N-[(6-methylpyridin-2-yl)methyl]-5-phenylthieno[2,3-d]pyrimidin-4-amine;
or a pharmaceutically acceptable salt thereof.

7. A process for preparing a compound as claimed in claim 1 comprising:

(i) reacting a compound of formula II with a suitable nucleophile X-L-Y, optionally in the presence of a solvent and a base, and optionally at elevated temperature or with microwave irradiation; or

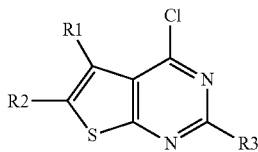

II (ii) reacting a compound of formula X by displacement of the 2-chloro substituent with a suitable nucleophilic species; or

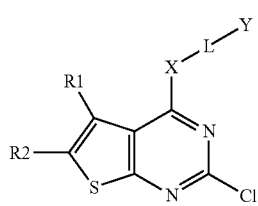

X (iii) reacting a compound of formula XVII with an aryl or heteroaryl boronic acid, optionally in the presence of a palladium catalyst, and optionally at elevated temperature or with microwave irradiation

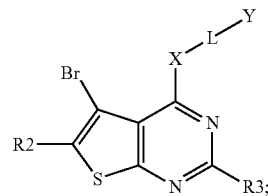

XVII wherein R1, R2, R3, X, L and Y are as defined in claim 1.

8. A pharmaceutical composition comprising at least one compound and one or more excipients, diluents or carriers, wherein said compound has the formula

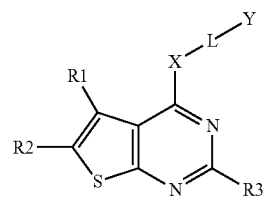

wherein

R1 is aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, C(O)NR9R10, NHC(O)R8, $SO_2NR9R10$, and hydroxyl; hetero aryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; or cycloalkyl;

R2 is H; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; nitro; $CO_2R7$; CONR4R5 or halo;

R3 is H; NR4R5; NHC(O)R8; halo; trifluoromethyl; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; cyano or alkoxy;

R4 and R5 may be the same or different, and may be H; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, C(O)NR9R10, NHC(O)R8, $SO_2NR9R10$, and hydroxyl; heteroaryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; or cycloalkyl; or R4 and R5 may together form a saturated, unsaturated or partially saturated 4 to 7 member ring, wherein said ring may optionally comprise one or more further heteroatoms selected from N, O or S;

X is O, S or NR6;

R6 is H or alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$;

R7 is hydrogen, methyl or ethyl;

R8 is methyl or ethyl;

R9 and R10 are independently selected from the group consisting of hydrogen, unsubstituted alkyl, unsubstituted aryl, unsubstituted heteroaryl, unsubstituted cycloalkyl, aminoethyl, methylaminoethyl, hydroxyethyl, and alkoxyethyl; or R9 and R10 taken together form a saturated, unsaturated, or partially saturated 4 to 7 membered ring;

L is $(CH2)_n$, where n is 1, 2 or 3; and

Y is heterocyclic group, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; alkenyl or cycloalkyl;

or a pharmaceutically acceptable salt thereof;

with the proviso that when Y is furanyl; tetrahydrofuranyl; pyrimidinyl;

pyrrolidinyl or 1,3-benzodioxolyl, then R1 is not phenyl, phenyl monosubstituted by halogen or phenyl substituted by methyl.

9. A method of treating or preventing arrhythmia or atrial fibrillation, comprising administering to a subject in need thereof an effective amount of at least one compound or a pharmaceutical composition comprising said at least one compound and one or more excipients, diluents or carriers wherein said compound has the formula:

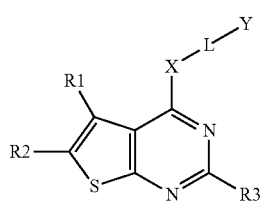

wherein

R1 is aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, C(O)NR9R10, NHC(O)R8, $SO_2NR9R10$, and hydroxyl; heteroaryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; cycloalkyl or alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$;

R2 is H; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; nitro; $CO_2R7$; CONR4R5 or halo;

R3 is H; NR4R5; NHC(O)R8; halo; trifluoromethyl; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; cyano or alkoxy;

R4 and R5 may be the same or different, and may be H; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, C(O)NR9R10, NHC(O)R8, $SO_2NR9R10$, and hydroxyl; heteroaryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; or cycloalkyl; or R4 and R5 may together form a saturated, unsaturated or partially saturated 4 to 7 member ring, wherein said ring may optionally comprise one or more further heteroatoms selected from N, O or S;

X is O, S or NR6;

R6 is H or alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$;

R7 is hydrogen, methyl or ethyl;

R8 is methyl or ethyl;

R9 and R10 are independently selected from the group consisting of hydrogen, unsubstituted alkyl, unsubstituted aryl, unsubstituted heteroaryl, unsubstituted cycloalkyl, aminoethyl, methylaminoethyl, hydroxyethyl, and alkoxyethyl; or R9 and R10 taken together form a saturated, unsaturated, or partially saturated 4 to 7 membered ring;

L is $(CH_2)_n$, where n is 1, 2 or 3; and

Y is aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, C(O)NR9R10, NHC(O)R8, $SO_2NR9R10$, and hydroxyl; heterocyclic group, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; alkenyl or cycloalkyl;

or a pharmaceutically acceptable salt thereof.

10. A process as claimed in claim 7, wherein R1 is aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, C(O)NR9R10, NHC(O)R8, $SO_2NR9R10$, and hydroxyl; or heteroaryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; R2 is H or alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; R3 is H; NR4R5; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; or alkoxy X is O or NR6, R6 is H, n is 1 or 2 and Y is cycloalkyl; or heteroaryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl.

11. A process as claimed in claim 7, wherein R1 is aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, C(O)NR9R10, NHC(O)R8, $SO_2NR9R10$, and hydroxyl; or heteroaryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; R2 is H or methyl, R3 is H; NR4R5; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; or alkoxy X is NR6, R6 is H, n is 1 and Y is heteroaryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl.

12. A process as claimed in claim 11, wherein Y is furanyl, thienyl or pyridyl.

13. A process as claimed in claim 11, wherein Y is optionally substituted furan-2-yl or optionally substituted pyridin-2-yl.

14. A method as claimed in claim 9, wherein R1 is aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, C(O)NR9R10, NHC(O)R8, $SO_2NR9R10$, and hydroxyl; or heteroaryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; R2 is H or alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$ R3 is H; NR4R5; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O) R8, and $SO_2NR9R10$; or alkoxy X is O or NR6, R6 is H, n is 1 or 2, and Y is cycloalkyl, or heteroaryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O) R8, $SO_2NR9R10$, and hydroxyl.

15. A method as claimed in claim 9, wherein R1 is aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, C(O)NR9R10, NHC(O)R8, $SO_2NR9R10$, and hydroxyl; or heteroaryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; R2 is H or methyl, R3 is H; NR4R5; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; or alkoxy X is NR6, R6 is H, n is 1 and Y is heteroaryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl.

16. A method as claimed in claim 15, wherein Y is furanyl, thienyl or pyridyl.

17. A method as claimed in claim 15, wherein Y is optionally substituted furan-2-yl or optionally substituted pyridin-2-yl.

18. A method of treating or preventing arrhythmia or atrial fibrillation, comprising administering to a subject in need thereof an effective amount of at least one compound or a pharmaceutical composition comprising said at least one compound and one or more excipients, diluents or carriers wherein said compound is:
2-{5-Phenyl-4-[(pyridin-2-ylmethyl)-amino]-thieno[2,3-d]pyrimidin-2-yl}-propane-1,3-diol;
2-{5-(4-Fluorophenyl)-4-[(pyridin-2-ylmethyl)-amino]-thieno[2,3-d]pyrimidin-2-ylamino}-ethanol;
Pyridin-2-ylmethyl-(5-p-tolyl-thieno[2,3-d]pyrimidin-4-yl)-amine;
2-{5-Phenyl-4-[(pyridin-2-ylmethyl)-amino]-thieno[2,3-d]pyrimidin-2-ylamino}-ethanol;
2-{5-Phenyl-4-[(pyridin-2-ylmethyl)amino]thieno[2,3-d]pyrimidin-2-yl}ethanol;
2-((2-Hydroxy-ethyl)-{5-phenyl-4-[(pyridin-2-ylmethyl)-amino]-thieno[2,3-d]pyrimidin-2-yl}-amino)-ethanol;
2-Methyl-N-(2-pyridyl)methyl-5-phenylthieno[2,3-d]pyrimidin-4-ylamine;
2-{4-[(Furan-2-ylmethyl)-amino]-5-phenyl-thieno[2,3-d]pyrimidin-2-yl}-ethanol;
[2-(2-Methoxy-ethoxy)-5-phenyl-thieno[2,3-d]pyrimidin-4-yl]-pyridin-2-ylmethylamine;
(2-Methoxy-5-phenyl-thieno[2,3-d]pyrimidin-4-yl)-pyridin-2-ylmethyl-amine;
5-(4-Fluorophenyl)-$N^2$-(2-methoxy-ethyl)-$N^4$-pyridin-2-ylmethyl-thieno[2,3-d]pyrimidine-2,4-diamine;
[5-(4-Dimethylamino-phenyl)-thieno[2,3-d]pyrimidin-4-yl]-pyridin-2-ylmethyl-amine;
5-(4-Fluorophenyl)-$N^2$,$N^2$-dimethyl-$N^4$-pyridin-2-ylmethyl-thieno[2,3-d]pyrimidine-2,4-diamine;
Pyridin-2-ylmethyl-[5-(4-trifluoromethyl-phenyl)-thieno[2,3-d]pyrimidin-4-yl]-amine;
[5-(1H-Indol-6-yl)-thieno[2,3-d]pyrimidin-4-yl]-pyridin-2-ylmethyl-amine;

(5-Benzo[1,3]dioxol-5-yl-thieno[2,3-d]pyrimidin-4-yl)-pyridin-2-ylmethyl-amine;

2-{5-Phenyl-4-[(pyridin-2-ylmethyl)-amino]-thieno[2,3-d]pyrimidin-2-ylamino}-propane-1,3-diol;

3-{5-Phenyl-4-[(pyridin-2-ylmethyl)-amino]-thieno[2,3-d]pyrimidin-2-ylamino}-propane-1,2-diol;

N-Methyl-2-{5-phenyl-4-[(pyridin-2-ylmethyl)amino]thieno[2,3-d]pyrimidin-2-yl}acetamide; or 6-Methyl-N-[(6-methylpyridin-2-yl)methyl]-5-phenylthieno[2,3-d]pyrimidin-4-amine;

and a pharmaceutically acceptable salt thereof.

19. An in vitro method of inhibiting Kv1.5 potassium channel current comprising contacting said potassium channel with a compound of claim 1.

20. A compound as claimed in claim 1, wherein

R1 is aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, C(O)NR9R10, NHC(O)R8, $SO_2NR9R10$, and hydroxyl; heteroaryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; or cycloalkyl;

R2 is H; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; nitro; or halo;

R3 is H; NR4R5; halo; trifluoromethyl; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; or alkoxy;

R4 and R5 may be the same or different, and may be H; alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$; aryl, which is unsubstituted or substituted at any position with one, two, three, or four substituents selected from the group consisting of cyano, halogen, nitro, trifluoromethyl, alkyl, alkylthio, alkoxy, NR9R10, $CO_2R7$, C(O)NR9R10, NHC(O)R8, $SO_2NR9R10$, and hydroxyl; heteroaryl, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; or cycloalkyl;

X is O, S or NR6;

R6 is H or alkyl, which is unsubstituted or substituted at any position with one or two substituents selected from the group consisting of halogen, cyano, nitro, NR9R10, alkoxy, hydroxyl, unsubstituted aryl, unsubstituted heteroaryl, $CO_2R7$, C(O)NR9R10, NHC(O)R8, and $SO_2NR9R10$;

L is $(CH_2)_n$, where n is 1, 2 or 3; and

Y is heterocyclic group, which is unsubstituted or substituted at any position with a substituent selected from the group consisting of cyano, nitro, halogen, alkyl, alkylthio, alkoxy, NR9R10, $CO_2R7$, C(O)NR9R10, NHC(O)R8, $SO_2NR9R10$, and hydroxyl; alkenyl or cycloalkyl.

* * * * *